United States Patent
Fujita et al.

(10) Patent No.: US 9,640,107 B2
(45) Date of Patent: May 2, 2017

(54) TRANSITION METAL COMPLEX AND ORGANIC LIGHT-EMITTING ELEMENT USING SAME, COLOR-CONVERTING LIGHT-EMITTING ELEMENT, LIGHT-CONVERTING LIGHT-EMITTING ELEMENT, ORGANIC LASER DIODE LIGHT-EMITTING ELEMENT, DYE LASER, DISPLAY DEVICE, ILLUMINATION DEVICE, AND ELECTRONIC EQUIPMENT

(75) Inventors: Yoshimasa Fujita, Osaka (JP); Masahito Ohe, Osaka (JP); Tetsuji Itoh, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 689 days.

(21) Appl. No.: 14/117,972

(22) PCT Filed: May 15, 2012

(86) PCT No.: PCT/JP2012/062386
§ 371 (c)(1),
(2), (4) Date: Jan. 17, 2014

(87) PCT Pub. No.: WO2012/157634
PCT Pub. Date: Nov. 22, 2012

(65) Prior Publication Data
US 2014/0152637 A1    Jun. 5, 2014

(30) Foreign Application Priority Data
May 19, 2011    (JP) ................... 2011-112436

(51) Int. Cl.
*H01L 51/00* (2006.01)
*G09G 3/3208* (2016.01)
(Continued)

(52) U.S. Cl.
CPC ......... *G09G 3/3208* (2013.01); *C07F 15/002* (2013.01); *C07F 15/0033* (2013.01);
(Continued)

(58) Field of Classification Search
None
See application file for complete search history.

(56) References Cited

U.S. PATENT DOCUMENTS

2005/0258433 A1  11/2005  Djurovich et al.
2006/0258043 A1  11/2006  Bold et al.
(Continued)

FOREIGN PATENT DOCUMENTS

CN  103261210 A   8/2013
JP   4351702 B2   10/2009
(Continued)

OTHER PUBLICATIONS

Chang et al., "Highly Efficient Blue-Emitting Iridium(III) Carbene Complexes and Phosphorescent OLEDs", Angewandte Chem. Int. Ed., vol. 47, 2008, pp. 4542-4545.
(Continued)

*Primary Examiner* — Nathan T Leong
(74) *Attorney, Agent, or Firm* — Morrison & Foerster LLP

(57) ABSTRACT

Disclosed is a transition metal complex represented by the following formula (1):
(Continued)

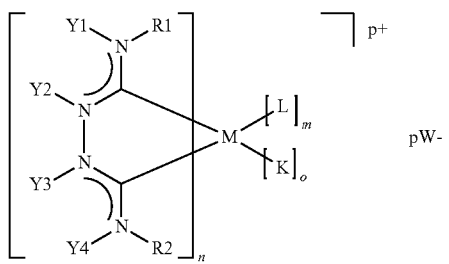

(wherein: M represents a transition metal element; K represents an uncharged monodentate or bidentate ligand; L represents a monodentate or bidentate mono-anionic or dianionic ligand; m and o represent an integer from 0 to 5; n represents an integer from 1 to 3; p represents an integer from 0 to 4; W— represents a counterion; and Y1 to Y4, R1, and R2 each independently represent a hydrogen atom, an alkyl group, a cycloalkyl group, a heterocycloalkyl group, an aryl group, an aralkyl group, a heteroaryl group, an alkenyl group, an alkynyl group, or an alkoxy group).

24 Claims, 10 Drawing Sheets

(51) Int. Cl.
| | | |
|---|---|---|
| | *C07F 15/00* | (2006.01) |
| | *C09K 11/06* | (2006.01) |
| | *H05B 33/14* | (2006.01) |
| | *H01S 3/02* | (2006.01) |
| | *H01S 5/36* | (2006.01) |
| | *H05B 33/08* | (2006.01) |

(52) U.S. Cl.
CPC .......... *C07F 15/0086* (2013.01); *C09K 11/06* (2013.01); *H01L 51/0085* (2013.01); *H01S 3/022* (2013.01); *H01S 5/36* (2013.01); *H05B 33/08* (2013.01); *H05B 33/14* (2013.01); *C09K 2211/1029* (2013.01); *C09K 2211/1044* (2013.01); *C09K 2211/1059* (2013.01); *C09K 2211/1074* (2013.01); *C09K 2211/185* (2013.01); *H01L 51/0037* (2013.01); *H01L 51/0072* (2013.01); *H01L 51/0087* (2013.01); *H01L 51/0088* (2013.01); *H01L 2251/308* (2013.01)

(56) References Cited

U.S. PATENT DOCUMENTS

2009/0326237 A1 12/2009 Strassner et al.
2013/0284977 A1 10/2013 Kunz et al.

FOREIGN PATENT DOCUMENTS

| JP | 2009-542026 A | | 11/2009 |
| JP | WO2010064621 | * | 6/2010 |
| WO | WO-2005/113704 A2 | | 12/2005 |

OTHER PUBLICATIONS

Costanzo et al., "Photochemical and Thermal Behaviour of Isocyanide Complexes", Journal of Organometallic Chemistry, vol. 289, 1985, pp. 81-90.
Doonan et al., "Carbene Complexes Resulting from the Addition of Various Amines to Isocyanide Complexes of Iron (II) and Ruthenium(II)", Inorganic Chemistry, vol. 13, No. 4, 1974, pp. 921-927.
Poyatos et al., "A Weak Donor, Planar Chelating Bitriazole N-Heterocyclic Carbene Ligand for Ruthenium(II), Palladium(II), and Rhodium", Organometallics, vol. 27, 2008, pp. 2128-2136.
Sajoto et al., "Blue and Near-UV Phosphorescence from Iridium Complexes with Cyclometalated Pyrazolyl or N-Heterocyclic Carbene Ligands", Inorganic Chemistry, vol. 44, No. 22, 2005, pp. 7992-8003.
Sanz et al., "'(n6-Arene)Ru(bis-NHC)' Complexes for the Reduction of CO2 to Formate with Hydrogen and by Transfer Hydrogenation with iPrOH", Dalton Transactions, vol. 39, 2010, pp. 6339-6343.
Song et al., "Phosphorescent IridiunnACHTUNGTRENUNG(III) Complexes with Nonconjugated Cyclometalated Ligands", Chemistry A European Journal, vol. 14, 2008, pp. 5423-5434.
Tokito et al., "Organic Electroluminescence Display", Ohmsha, Aug. 2004, 182 pages (3 pages of partial translation and 179 pages of official copy).
Yersin, Hartmut, "Highly Efficient OLEDs with Phosphorescent Materials", Wiley-VCH, 2008, 452 pages.
You et al., "Highly Phosphorescent Iridium Complexes with Chromophoric 2-(2-Hydroxyphenyl)oxazole-Based Ancillary Ligands: Interligand Energy-Harvesting Phosphorescence", Inorganic Chemistry, vol. 47, No. 5, 2008, pp. 1476-1487.
Gazzola et al., "Alkyne hydroarylation with palladium(II) complexes bearing chelating N-heterocyclic ligands: effect of non-coordinated nitrogens on catalyst efficiency", New Journal of Chemistry, Jan. 2010, pp. 482-486.
Balch et al., "Platinum and palladium Complexes Formed by Chelative Addition of Amines to Isocyanides"., Journal of the American Chemical Society, Jun. 1974, pp. 4114-4121.

* cited by examiner

TRANSITION METAL COMPLEX AND ORGANIC LIGHT-EMITTING ELEMENT USING SAME, COLOR-CONVERTING LIGHT-EMITTING ELEMENT, LIGHT-CONVERTING LIGHT-EMITTING ELEMENT, ORGANIC LASER DIODE LIGHT-EMITTING ELEMENT, DYE LASER, DISPLAY DEVICE, ILLUMINATION DEVICE, AND ELECTRONIC EQUIPMENT

CROSS REFERENCE TO RELATED APPLICATIONS

This is a U.S. National Phase patent application of PCT/JP2012/062386 filed May 15, 2012, which claims priority to Japanese Patent Application NO. JP 2011-112436 filed May 19, 2011, each of which is hereby incorporated by reference in the present disclosure in its entirety.

TECHNICAL FIELD

The present invention relates to a transition metal complex and an organic light-emitting element using the same, a color-converting light-emitting element, a light-converting light-emitting element, an organic laser diode light-emitting element, a dye laser, a display device, an illumination device, and electronic equipment.

Priority is claimed on Japanese Patent Application No. 2011-112436, filed May 19, 2011, the content of which is incorporated herein by reference.

BACKGROUND ART

A highly efficient luminescent material has been developed for reducing the power consumption of an organic EL (electroluminescence) element. A phosphorescent luminescent material using the emission from the triplet excited state can achieve a high luminous efficiency compared to a fluorescent luminescent material using only the fluorescent emission from the singlet excited state. Therefore, a phosphorescent luminescent material has been developed.

Currently, a phosphorescent material capable of achieving an internal quantum efficiency of approximately 100% at a maximum is used for green pixels and red pixels of an organic EL element. However, a fluorescent material having an internal quantum efficiency of approximately 25% at a maximum is used for blue pixels. The reason is that blue light emission requires a higher energy than that of red light or green light emission; and when it is attempted to obtain high-energy emission from phosphorescent emission at the triplet excited level, portions in a molecular structure which are unstable under high energy are likely to deteriorate.

As a blue phosphorescent material, in order to achieve a high-energy triplet excited state, an iridium (Ir) complex in which an electron-attracting group such as fluorine is introduced into a ligand as a substituent is known (for example, refer to NPLs 1 to 5). However, in a blue phosphorescent material into which an electron-attracting group is introduced, the luminous efficiency is relatively high, whereas the light resistance is low and the lifetime is short.

In addition, it is reported that short-wavelength emission is possible in a complex in which a carbene ligand is used without introducing an electron-attracting group thereinto (refer to NPL 6 and PTL 1).

CITATION LIST

Patent Literature

PTL 1: Japanese Patent No. 4351702

Non Patent Literature

NPL 1: Angewandte Chemie International Edition, 2008, 47, 4542-4545

NPL 2: Chemistry-A European Journal, 2008, 14, 5423-5434

NPL 3: Inorganic Chemistry, Volume 47, No. 5, 2008, 1476-1487

NPL 4: "Organic EL Display", Ohmsha, TOKITO Shizuo, ADACHI Chihaya, and MURATA Hideyuki, August 2004, pp. 109 to 111

NPL 5: "Highly Efficient OLEDs with Phosphorescent Materials", Edited by Hartmut Yersin, Germany, VILEY-VCH, December, 2007, pp. 363 to 390

NPL 6: Inorganic Chemistry, 44, 2005, 7992

SUMMARY OF INVENTION

Technical Problem

Luminescent materials disclosed in NPL 6 and PTL 1 emit blue phosphorescence without introducing an electron-attracting group, which deteriorates light resistance, thereinto. However, the luminous efficiency is low.

Therefore, the development of a luminescent material, which emits blue light with a high luminous efficiency without introducing an electron-attracting group thereinto, is desired. In addition, in order to obtain high-color-purity blue light, a luminescent material having a high T1 level (triplet excited level) is required.

Further, in order to obtain a device capable of achieving a high luminous efficiency and a long lifetime, it is important to prevent excitation energy of a luminescent material from being transferred to a host material and a material in contact with a light-emitting layer.

Accordingly, a host material having a higher T1 level (triplet excited level) than that of a luminescent material is required, and several kinds of carbazole compounds and silicon compounds are used as such a host material. However, the development of a novel host material is desired.

Solution to Problem

According to some aspects of the invention, there are provided: a transition metal complex having a high T1 level that is applicable to a luminescent material, a host material, an exciton blocking material, and the like; an organic light-emitting element using the same; a color-converting light-emitting element; a light-converting light-emitting element; an organic laser diode light-emitting element; a dye laser; a display device; an illumination device; and electronic equipment.

The present inventors have completed the above-described aspects of the invention. That is, the aspects of the invention adopt the following configurations.

According to an aspect of the invention, there is provided a dicarbene transition metal complex represented by the following formula (1).

[Chem. 1]

(1)

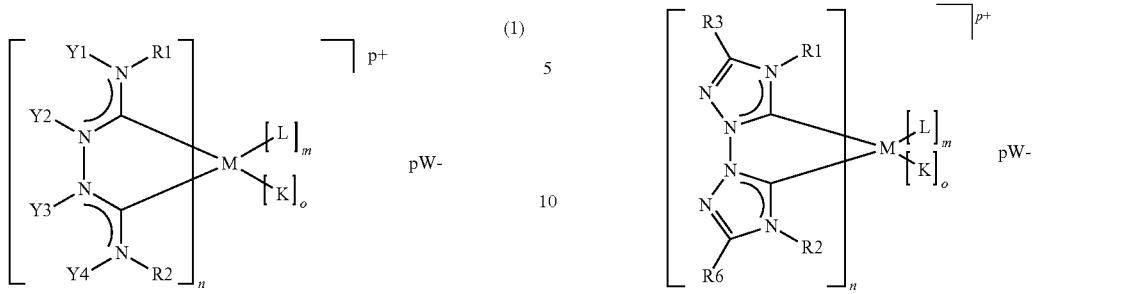

(In the formula (1), M represents a transition metal element selected from the group consisting of Group 8 to Group 12 transition metal elements in the periodic table, where the transition metal element represented by M is in any oxidation state; K represents an uncharged monodentate or bidentate ligand; L represents a monodentate or bidentate monoanionic or dianionic ligand; m represents an integer from 0 to 5; o represents an integer from 0 to 5; n represents an integer from 1 to 3; p represents the number of charges in the complex which is represented by an integer from 0 to 4; W— represents a monoanionic counterion; m, o, n, and p are dependent on the oxidation state and coordination number of the transition metal element represented by M or on the charge on ligands and the charge on the entire complex; Y1, Y2, Y3, and Y4 each independently represent a hydrogen atom, an alkyl group, a cycloalkyl group, a heterocycloalkyl group, an aryl group, a heteroaryl group, an aralkyl group, an alkenyl group, an alkynyl group, or an alkoxy group, where each group is optionally substituted or unsubstituted; regarding Y1 and Y2, Y2 and Y3, and Y3 and Y4, independently of one another, parts thereof are optionally bonded and integrated to form a saturated or unsaturated ring structure having at least two atoms between nitrogen atoms, where one or more atoms of the ring structure are optionally substituted with an alkyl group or an aryl group (a substituent thereof is optionally further substituted or unsubstituted) and the ring structure optionally forms one or more further ring structures; and R1 and R2 each independently represent a hydrogen atom, an alkyl group, a cycloalkyl group, a heterocycloalkyl group, an aryl group, an aralkyl group, a heteroaryl group, an alkenyl group, an alkynyl group, or an alkoxy group, where each group is optionally substituted or unsubstituted).

The transition metal complex according to the aspect of the invention may be represented by any one of the following formulae (2) to (5).

[Chem. 2]

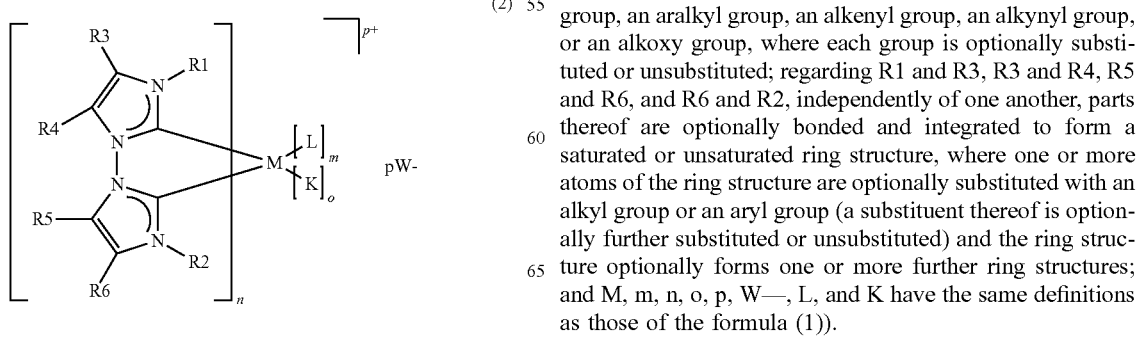

(In the formulae (2) to (5), R1 to R6 each independently represent a hydrogen atom, an alkyl group, a cycloalkyl group, a heterocycloalkyl group, an aryl group, a heteroaryl group, an aralkyl group, an alkenyl group, an alkynyl group, or an alkoxy group, where each group is optionally substituted or unsubstituted; regarding R1 and R3, R3 and R4, R5 and R6, and R6 and R2, independently of one another, parts thereof are optionally bonded and integrated to form a saturated or unsaturated ring structure, where one or more atoms of the ring structure are optionally substituted with an alkyl group or an aryl group (a substituent thereof is optionally further substituted or unsubstituted) and the ring structure optionally forms one or more further ring structures; and M, m, n, o, p, W—, L, and K have the same definitions as those of the formula (1)).

The transition metal complex according to the aspect may be represented by the following formula (6) or (7).

[Chem. 3]

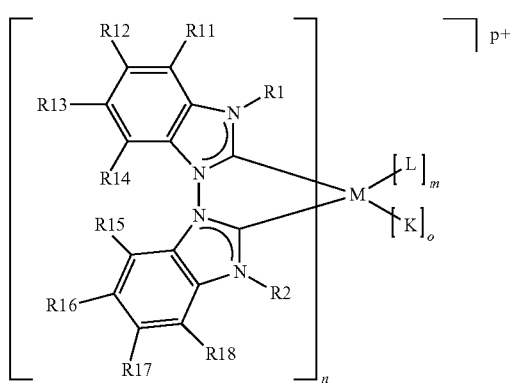

(6)

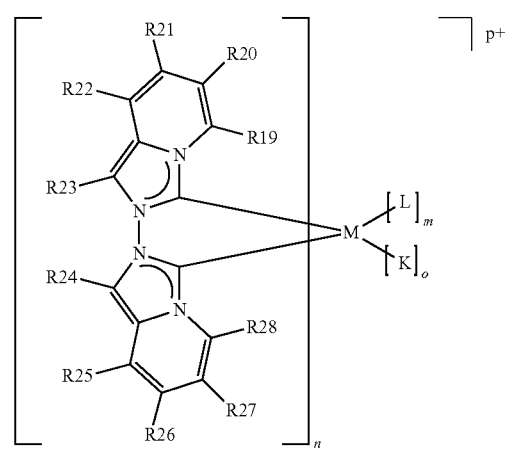

(7)

(In the formulae (6) and (7), R1, R2, M, m, n, o, p, W—, L, and K have the same definitions as those of the formula (1); R11 to R28 each independently represent a hydrogen atom, an alkyl group, a cycloalkyl group, a heterocycloalkyl group, an aryl group, a heteroaryl group, an aralkyl group, an alkenyl group, an alkynyl group, or an alkoxy group, where each group is optionally substituted or unsubstituted; regarding R1 and R11 to R14, and R2 and R15 to R18, R19 to R23, and R24 to R28, independently of one another, parts of adjacent two thereof are optionally bonded and integrated to form a saturated or unsaturated ring structure, where one or more atoms of the ring structure are optionally substituted with an alkyl group or an aryl group (a substituent thereof is optionally further substituted or unsubstituted) and the ring structure optionally forms one or more further ring structures).

In the transition metal complex according to the aspect, R1 to R6 in any one of the formulae (2) to (5) may each independently represent a hydrogen atom, a methyl group, or a phenyl group.

In the transition metal complex according to the aspect, R1, R2, and R11 to R18 in the formula (6) or R19 to R28 in the formula (7) each independently represent a hydrogen atom, a methyl group, or a phenyl group.

In the transition metal complex according to the aspect, the M may represent iridium, osmium, or platinum.

In the transition metal complex according to the aspect, the W— may represent Cl⁻, Br⁻, I⁻, PF$_6$⁻, BF$_4$⁻OAc (Ac represents COCH$_3$), SbF$_6$⁻, AsF$_6$⁻, NCO⁻, ClO$_4$⁻, or CN⁻.

In the transition metal complex according to the aspect, the L may represent Br⁻, I⁻, OAc⁻ (Ac represents COCH$_3$), or NCS⁻.

In the transition metal complex according to the aspect, the L may represent a ligand having a structure represented by any one of the following formula (12) to (16).

[Chem. 4]

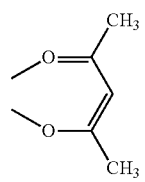

(12)

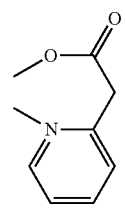

(13)

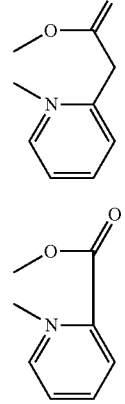

(14)

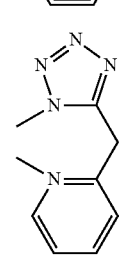

(15)

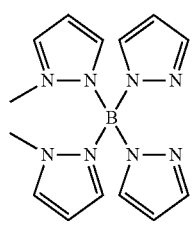

(16)

In the transition metal complex according to the aspect, the K may represent a phosphine, a phosphonate, and a derivative thereof; an arsenate and a derivative thereof; a phosphite; CO; a pyridine; or a nitrile.

According to another aspect of the invention, there is provided an organic light-emitting element including: at least one organic layer that includes a light-emitting layer; and a pair of electrodes between which the organic layer is interposed, in which at least a part of the organic layer contains the above-described transition metal complex.

In the organic light-emitting element according to the aspect, the transition metal complex may be used as a luminescent material.

In the organic light-emitting element according to the aspect, the transition metal complex may be used as a host material.

In the organic light-emitting element according to the aspect, the transition metal complex may be used as an exciton blocking material.

According to still another aspect of the invention, there is provided a color-converting light-emitting element including: the above-described organic light-emitting element; and a phosphor layer that is disposed on a light-emitting side of the organic light-emitting element, absorbs light emitted from the organic light-emitting element, and emits light having a different color from that of the absorbed light.

According to still another aspect of the invention, there is provided a color-converting light-emitting element including: a light-emitting element; and a phosphor layer that is disposed on a light-emitting side of the light-emitting element, absorbs light emitted from the light-emitting element, and emits light having a different color from that of the absorbed light, in which the phosphor layer contains the above-described transition metal complex.

According to still another aspect of the invention, there is provided a light-converting light-emitting element including: at least one organic layer that includes a light-emitting layer; a layer for multiplying a current; and a pair of electrodes between which the organic layer and the layer for multiplying a current are interposed, in which the light-emitting layer contains the above-described transition metal complex.

According to still another aspect of the invention, there is provided an organic laser diode light-emitting element including: a continuous-wave excitation light source; and a resonator structure that is irradiated with light emitted from the continuous-wave excitation light source, in which the resonator structure includes at least one organic layer that includes a laser-active layer, and a pair of electrodes between which the organic layer is interposed, and the laser-active layer includes a host material doped with the above-described transition metal complex.

According to still another aspect of the invention, there is provided a dye laser including: a laser medium that contains the above-described transition metal complex; and an excitation light source with which laser oscillation is achieved by stimulated emission of phosphorescent light from the organic light-emitting element material contained in the laser medium.

According to still another aspect of the invention, there is provided a display device including: an image signal output portion that outputs an image signal; a driver that applies a current or a voltage based on the signal output from the image signal output portion; and a light-emitting portion that emits light based on the current or the voltage applied from the driver, in which the light-emitting portion is the above-described organic light-emitting element.

According to still another aspect of the invention, there is provided a display device including: an image signal output portion that outputs an image signal; a driver that applies a current or a voltage based on the signal output from the image signal output portion; and a light-emitting portion that emits light based on the current or the voltage applied from the driver, in which the light-emitting portion is the above-described color-converting light-emitting element.

In the display device according to the aspect, an anode and a cathode of the light-emitting portion may be arranged in a matrix shape.

In the display device according to the aspect, the light-emitting portion may be driven by a thin film transistor.

According to still another aspect of the invention, there is provided an illumination device including: a driver that applies a current or a voltage; and a light-emitting portion that emits light based on the current or the voltage applied from the driver, in which the light-emitting portion is the above-described organic light-emitting element.

According to still another aspect of the invention, there is provided an illumination device including: a driver that applies a current or a voltage; and a light-emitting portion that emits light based on the current or the voltage applied from the driver, in which the light-emitting portion is the above-described color-converting light-emitting element.

According to still another aspect of the invention, there is provided electronic equipment including the above-described display device.

Advantageous Effects of Invention

According to the aspects of the invention, it is possible to provide: a transition metal complex having a high T1 level that is applicable to a luminescent material, a host material, an exciton blocking material, and the like; an organic light-emitting element using the same; a color-converting light-emitting element; a light-converting light-emitting element; an organic laser diode light-emitting element; a dye laser; a display device; an illumination device; and electronic equipment.

DESCRIPTION OF EMBODIMENTS

Figure 1:
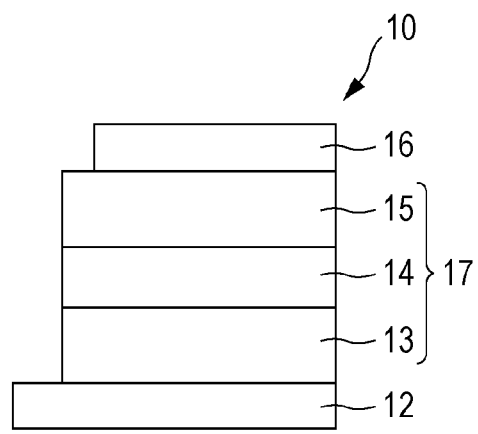
FIG. 1 is a diagram schematically illustrating a first embodiment of an organic light-emitting element according to the invention.

Hereinafter, an organic light-emitting element material and an organic light-emitting element using the same, a color-converting light-emitting element, a light-converting light-emitting element, an organic laser diode light-emitting element, a dye laser, a display device, and an illumination device, and electronic equipment according to aspects of the invention will be described. The following embodiments are merely specific examples for easy understanding of the concepts of the invention. Unless specified otherwise, the aspects of the invention are not limited to the embodiments. In addition, for the purpose of easy understanding of characteristics of the aspects of the invention, in the drawings used for the following description, major parts may be illustrated in an enlarged manner for convenience of illustration. A dimension ratio or the like of each component may be different from the actual one.

<Transition Metal Complex>

A transition metal complex according to the invention has a high T1 level and is desirably used as a luminescent material, a host material, a charge transport material, and an exciton blocking material of an organic EL (electroluminescent) element, preferably, as a luminescent material, a host material, and an exciton blocking material.

The transition metal complex according to the invention is a dicarbene transition metal complex represented by the following formula (1).

[Chem. 5]

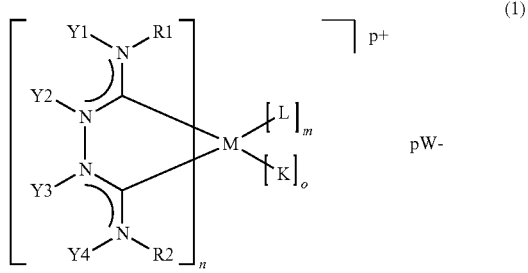

(1)

In the formula (1), M represents a transition metal element selected from the group consisting of Group 8 to Group 12 transition metal elements in the periodic table, where the transition metal element represented by M is able to be in any oxidation state; K represents an uncharged monodentate or bidentate ligand; L represents a monodentate or bidentate monoanionic or dianionic ligand; m represents an integer from 0 to 5; o represents an integer from 0 to 5; n represents an integer from 1 to 3; p represents the number of charges in the complex which is represented by an integer from 0 to 4; W— represents a monoanionic counterion; m, o, n, and p are dependent on the oxidation state and coordination number of the transition metal element represented by M or on the charge on ligands and the charge on the entire complex; Y1, Y2, Y3, and Y4 each independently represent a hydrogen atom, an alkyl group, a cycloalkyl group, a heterocycloalkyl group, an aryl group, a heteroaryl group, an aralkyl group, an alkenyl group, an alkynyl group, or an alkoxy group, where each group is optionally substituted or unsubstituted; regarding Y1 and Y2, Y2 and Y3, and Y3 and Y4, independently of one another, parts thereof are optionally bonded and integrated to form a saturated or unsaturated ring structure having at least two atoms between nitrogen atoms, where one or more atoms of the ring structure are optionally substituted with an alkyl group or an aryl group (a substituent thereof is optionally further substituted or unsubstituted) and the ring structure optionally forms one or more further ring structures; and R1 and R2 each independently represent a hydrogen atom, an alkyl group, a cycloalkyl group, a heterocycloalkyl group, an aryl group, an aralkyl group, a heteroaryl group, an alkenyl group, an alkynyl group, or an alkoxy group, where each group is optionally substituted or unsubstituted.

In the formula (1), M represents a transition metal element selected from the group consisting of Group 8 to Group 12 transition metal elements in the periodic table, where the transition metal element represented by M is able to be in any oxidation state. The oxidation state of the transition metal element is not particularly limited. Specific examples of the transition metal element represented by M include Ir, Pt, Pd, Rh, Re, Ru, Os, Ti, Bi, In, Sn, Sb, Te, Au, and Ag. Among these, Ir, Os, and Pt are preferable from the viewpoint of increasing a PL quantum yield due to a heavy atom effect described below.

It is generally known that, when a transition metal complex is expected as a highly efficient phosphorescent luminescent material, MLCT (Metal-to-Ligand Charge Transfer) is used as an emission mechanism. At this time, a heavy atom effect of a central metal works effectively on a ligand, and intersystem crossing (transition from the singlet excited state to the triplet excited state, S→T: approximately 100%) occurs rapidly. Then, similarly, due to a heavy atom effect, the transition rate constant ($k_r$) from $T_1$ to $S_0$ is increased. As a result, the PL quantum yield ($\phi_{PL}=k_r/(k_{nr}+k_r)$; wherein $k_{nr}$ represents the rate constant of being thermally deactivated from $T_1$ to $S_0$) is increased. The increase in PL quantum yield leads to an increase in the luminous efficiency of an organic electronic device.

In Ir, Os, or Pt, the atomic radius is relatively short due to lanthanide contraction, whereas the atomic weight is great. Therefore, the above-described heavy atom effect can be effectively exhibited. Accordingly, when the transition metal complex according to the aspect of the invention is used as a luminescent material, by using Ir, Os, or Pt as a central metal thereof, the PL quantum yield increases due to the heavy atom effect, and a high luminous efficiency can be obtained.

In the formula (1), m represents an integer from 0 to 5, o represents an integer from 0 to 5, and n represents an integer from 1 to 3. p represents the number of charges in the complex which is represented by an integer from 0 to 4. m, o, n, and p are dependent on the oxidation state and coordination number of a transition metal complex to be used or on the charge on ligands and the charge on the entire complex.

K represents an uncharged monodentate or bidentate ligand, and specifically preferably represents a phosphine, a phosphonate, and a derivative thereof; an arsenate and a derivative thereof; a phosphite; CO; a pyridine; or a nitrile.

In addition, as K, a group represented by the following formula (K-1) is preferable.

L represents a monodentate or bidentate monoanionic or dianionic ligand. Specific examples of L include halogen and pseudohalogen. As the halogen, $Br^-$ or $I^-$ is preferable. As the pseudohalogen, $OAc^-$ (Ac represents $COCH_3$) or $NCS^-$ is preferable.

In addition, as L, groups represented by the following formulae (L-1) to (L-5) are also preferable.

W— represents a monoanionic counterion, and specific examples thereof include halogen and pseudohalogen. As the halogen, $Cl^-$, $Br^-$, or $I^-$ is preferable, and as the pseudohalogen, $PF_6^-$, $BF_4^-OAc$ (Ac represents $COCH_3$), $SbF_6^-$, $AsF_6^-$, $NCO^-$, $ClO_4^-$, or $CN^-$ is preferable.

In the formula (1), R1 and R2 each independently represent a hydrogen atom, an alkyl group, a cycloalkyl group, a heterocycloalkyl group, an aryl group, an aralkyl group, a heteroaryl group, an alkenyl group, an alkynyl group, or an alkoxy group, where each group is optionally substituted or unsubstituted.

Examples of the alkyl group represented by R1 and R2 include an alkyl group having 1 to 8 carbon atoms, and specific examples thereof include a methyl group, an ethyl group, an n-propyl group, an isopropyl group, an n-butyl group, a tert-butyl group, an n-pentyl group, an n-hexyl group, an n-heptyl group, and an n-octyl group.

Examples of the cycloalkyl group represented by R1 and R2 include a cycloalkyl group having 3 to 8 carbon atoms, and specific examples thereof include a cyclopropyl group, cyclobutyl group, a cyclopentyl group, a cyclohexyl group, a cycloheptyl group, and a cyclooctyl group.

Examples of the heterocycloalkyl group represented by R1 and R2 include cycloalkyl groups in which one or more carbon atoms forming a cyclic structure are substituted with a nitrogen atom, an oxygen atom, a sulfur atom, or the like. Specific examples of the heterocycloalkyl group include an azepanyl group, a diazepanyl group, an aziridinyl group, an azetidinyl group, a pyrrolidinyl group, an imidazolidinyl group, a piperidyl group, a pyrazolidinyl group, a piperazinyl group, an azocanyl group, a thiomorpholinyl group, a thiazolidinyl group, an isothiazolidinyl group, an oxazolidinyl group, a morpholinyl group, a tetrahydrothiopyranyl group, an oxathiolanyl group, an oxiranyl group, an oxetanyl group, a dioxolanyl group, a tetrahydrofuranyl group, a tetrahydropyranyl group, a 1,4-dioxanyl group, a quinuclidinyl group, a 7-azabicyclo[2.2.1]heptyl group, a 3-azabicyclo[3.2.2]nonanyl group, a trithiadiazaindenyl group, a dioxoloimidazolidinyl group, and a 2,6-dioxabicyclo[3.2.2]oct-7-yl group.

Specific examples of the aryl group represented by R1 and R2 include a phenyl group, a terphenyl group, a naphthyl group, a tolyl group, a fluorophenyl group, a xylyl group, a biphenylyl group, an anthryl group, and a phenanthryl group.

Specific examples of the aralkyl group represented by R1 and R2 include a benzyl group, and a phenethyl group.

Examples of the heteroaryl group represented by R1 and R2 include aryl groups in which one or more carbon atoms forming a cyclic structure are substituted with a nitrogen atom, an oxygen atom, a sulfur atom, or the like. Specific examples of the heteroaryl group include a pyrrolyl group, a furyl group, a thienyl group, an oxazolyl group, an isoxazolyl group, an imidazolyl group, a triazolyl group, an isothiazolyl group, a pyrazolyl group, a triazolyl group, a tetrazolyl group, a 1,3,5-oxadiazolyl group, a 1,2,4-oxadiazolyl group, a 1,2,4-thiadiazolyl group, a pyridyl group, a pyranyl group, a pyrazinyl group, a pyrimidinyl group, a pyridazinyl group, a 1,2,4-triazinyl group, a 1,2,3-triazinyl group, and a 1,3,5-triazinyl group.

Specific examples of the alkenyl group represented by R1 and R2 include an ethenyl group, a 1-propenyl group, a 2-propenyl group, a 2-methyl-1-propenyl group, a 2-methyl-2-propenyl group, a 1-butenyl group, a 2-butenyl group, a 3-butenyl group, a 2-methyl-1-butenyl group, a 3-methyl-2-butenyl group, a 1-pentenyl group, a 2-pentenyl group, a 3-pentenyl group, a 4-pentenyl group, a 4-methyl-3-pentenyl group, a 1-hexenyl group, a 2-hexenyl group, a 3-hexenyl group, a 4-hexenyl group, a 5-hexenyl group, a 1-heptenyl group, and a 1-octenyl group.

Specific examples of the alkynyl group represented by R1 and R2 include an ethynyl group, a 1-propynyl group, a 2-propynyl group, a 1-butynyl group, a 2-butynyl group, a 3-butynyl group, a 1-pentynyl group, a 2-pentynyl group, a 3-pentynyl group, a 4-pentynyl group, a 1-hexynyl group, a 2-hexynyl group, a 3-hexynyl group, a 4-hexynyl group, a 5-hexynyl group, a 1-heptynyl group, and a 1-octynyl group.

Specific examples of the alkoxy group represented by R1 and R2 include a methoxy group, an ethoxy group, a propoxy group, a butoxy group, an octyloxy group, and a decyloxy group.

Among these, as the group represented by the R1 and R2, a hydrogen atom, an alkyl group, or an aryl group is preferable; a hydrogen atom, a methyl group, an ethyl group, an n-propyl group, an isopropyl group, an n-butyl group, a tert-butyl group, an n-pentyl group, an n-hexyl group, an n-heptyl group, an n-octyl group, a cyclohexyl group, a phenyl group, or a naphthyl group is more preferable; a hydrogen atom, a methyl group, a propyl group, or a phenyl group is still more preferable; a hydrogen atom, a methyl group, or a phenyl group is particularly preferable.

In the formula (1), Y1, Y2, Y3, and Y4 each independently represent a hydrogen atom, an alkyl group, a cycloalkyl group, a heterocycloalkyl group, an aryl group, a heteroaryl group, an aralkyl group, an alkenyl group, an alkynyl group, or an alkoxy group, where each group is optionally substituted or unsubstituted. Regarding Y1 and Y2, Y2 and Y3, and Y3 and Y4, independently of one another, parts thereof are optionally bonded and integrated to form a saturated or unsaturated ring structure having at least two atoms between nitrogen atoms. In this case, one or more atoms of the ring structure are optionally substituted with an alkyl group or an aryl group (a substituent thereof is optionally further substituted or unsubstituted) and the ring structure optionally forms one or more further ring structures.

Examples of the alkyl group, the cycloalkyl group, the heterocycloalkyl group, the aryl group, the heteroaryl group, the aralkyl group, the alkenyl group, the alkynyl group, and the alkoxy group which are represented by the Y1, Y2, Y3, and Y4 are the same as the above-described examples of those represented by R1 and R2.

As Y1, Y2, Y3, and Y4, a hydrogen atom, an alkyl group, an aryl group, or an alkoxy group is preferable; and a hydrogen atom, a methyl group, an ethyl group, an n-propyl group, an isopropyl group, an n-butyl group, a tert-butyl group, an n-pentyl group, an n-hexyl group, an n-heptyl group, an n-octyl group, a cyclohexyl group, a phenyl group, a naphthyl group, a methoxy group, an ethoxy group, or a propoxy group is more preferable.

When parts of any of Y1 and Y2, Y2 and Y3, and Y3 and Y4 are integrated to form a ring structure, specific examples of the alkyl group or the aryl group as the substituent which is optionally included in the ring structure include a methyl group, an ethyl group, an n-propyl group, an isopropyl group, an n-butyl group, a tert-butyl group, an n-pentyl group, an n-hexyl group, an n-heptyl group, an n-octyl group, a cyclohexyl group, a phenyl group, and a naphthyl group. Among these, a methyl group, a propyl group, or a phenyl group is preferable; and a methyl group or a phenyl group is more preferable.

It is preferable that the transition metal complex represented by the formula (1) have a structure represented by any one of the following formulae (2) to (5).

[Chem. 6]

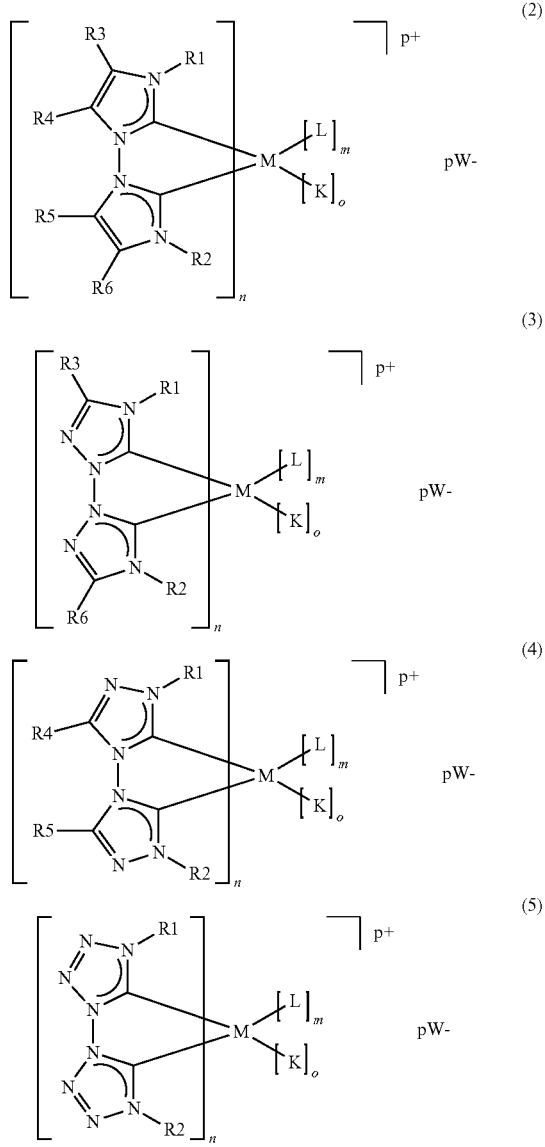

In the formulae (2) to (5), R1 to R6 each independently represent a hydrogen atom, an alkyl group, a cycloalkyl group, a heterocycloalkyl group, an aryl group, a heteroaryl group, an aralkyl group, an alkenyl group, an alkynyl group, or an alkoxy group, where each group is optionally substituted or unsubstituted; regarding R1 and R3, R3 and R4, R5 and R6, and R6 and R2, independently of one another, parts thereof are optionally bonded and integrated to form a saturated or unsaturated ring structure, where one or more atoms of the ring structure are optionally substituted with an alkyl group or an aryl group (a substituent thereof is optionally further substituted or unsubstituted) and the ring structure optionally forms one or more further ring structures; and M, m, n, o, p, W—, L, and K have the same definitions as those of the formula (1).

Specific examples of the alkyl group, the cycloalkyl group, the heterocycloalkyl group, the aryl group, the heteroaryl group, the aralkyl group, the alkenyl group, the alkynyl group, and the alkoxy group represented by R1 to R6 are the same as the above-described examples of those represented by R1 and R2 in the formula (1).

As the group represented by R1 to R6, a hydrogen atom, an alkyl group, an aryl group, or an alkoxy group is preferable, and specific examples thereof include a hydrogen atom, a methyl group, an ethyl group, an n-propyl group, an isopropyl group, an n-butyl group, a tert-butyl group, an n-pentyl group, an n-hexyl group, an n-heptyl group, an n-octyl group, a cyclohexyl group, a phenyl group, a naphthyl group, a methoxy group, an ethoxy group, and a propoxy group. Among these, a hydrogen atom, a methyl group, a propyl group, or a phenyl group is preferable; and a hydrogen atom, a methyl group, or a phenyl group is more preferable.

When parts of any of R1 and R3, R3 and R4, R5 and R6, and R6 and R2 are bonded to form a ring structure, examples of the alkyl group or the aryl group as the substituent which is optionally included in the ring structure are the same as the above-described examples of the substituent which is optionally included in the ring structure in the formula (1).

In addition, it is also preferable that the transition metal complex represented by the formula (1) have a structure represented by the following formula (6) or (7).

[Chem. 7]

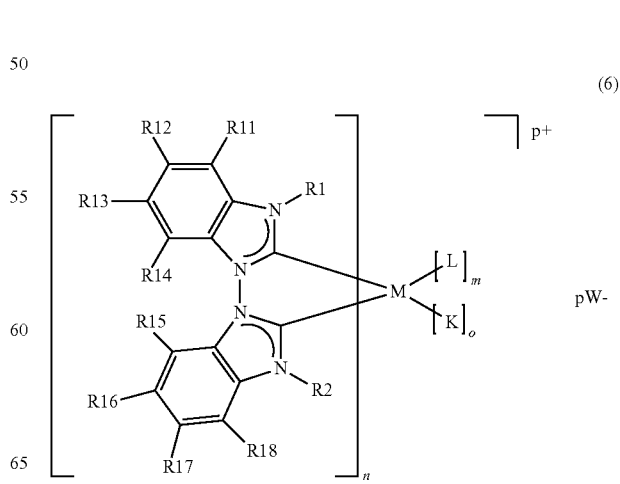

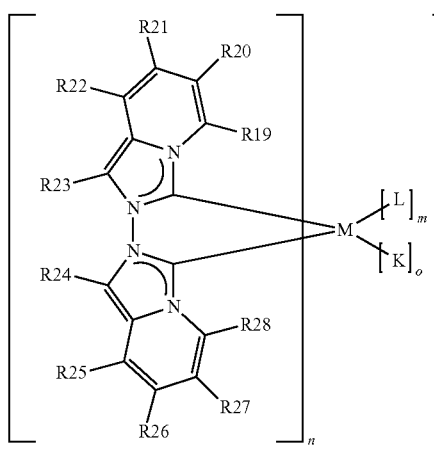

(7)

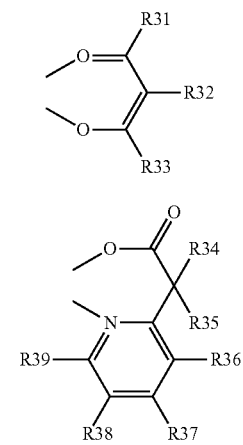

(L-1)

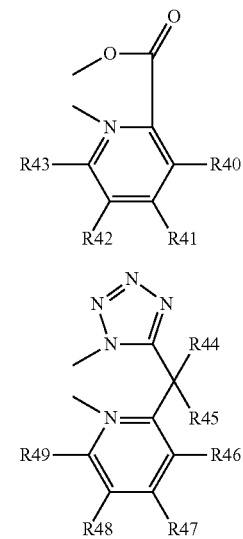

(L-2)

(L-3)

(L-4)

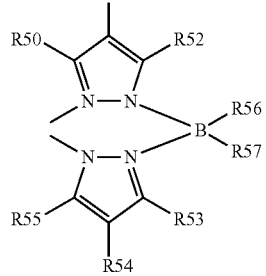

(L-5)

In the formulae (6) and (7), R1, R2, M, m, n, o, p, W—, L, and K have the same definitions as those of the formula (1); R11 to R28 each independently represent a hydrogen atom, an alkyl group, a cycloalkyl group, a heterocycloalkyl group, an aryl group, a heteroaryl group, an aralkyl group, an alkenyl group, an alkynyl group, or an alkoxy group, where each group is optionally substituted or unsubstituted; regarding R1 and R11 to R14, and R2 and R15 to R18, R19 to R23, and R24 to R28, independently of one another, parts of adjacent two thereof are optionally bonded and integrated to form a saturated or unsaturated ring structure, where one or more atoms of the ring structure are optionally substituted with an alkyl group or an aryl group (a substituent thereof is optionally further substituted or unsubstituted) and the ring structure optionally forms one or more further ring structures.

Specific examples of the alkyl group, the cycloalkyl group, the heterocycloalkyl group, the aryl group, the heteroaryl group, the aralkyl group, the alkenyl group, the alkynyl group, and the alkoxy group represented by R11 to R28 are the same as the above-described examples of those represented by R1 and R2 in the formula (1).

As the group represented by R1, R2, and R11 to R28, a hydrogen atom, an alkyl group, or an aryl group is preferable, and specific examples thereof include a hydrogen atom, a methyl group, an ethyl group, an n-propyl group, an isopropyl group, an n-butyl group, a tert-butyl group, an n-pentyl group, an n-hexyl group, an n-heptyl group, an n-octyl group, a cyclohexyl group, a phenyl group, and a naphthyl group. Among these, a hydrogen atom, a methyl group, a propyl group, or a phenyl group is preferable; and a hydrogen atom, a methyl group, or a phenyl group is more preferable.

When adjacent parts of any of R1 and R11 to R14, and R2 and R15 to R18, R19 to R23, and R24 to R28 are bonded to form a ring structure, examples of the alkyl group or the aryl group as the substituent which is optionally included in the ring structure are the same as the above-described examples of the substituent which is optionally included in the ring structure in the formula (1).

In the formulae (1) to (7), Br⁻ or I⁻ is preferable as L, and OAc (Ac represents COCH$_3$), or NCS is preferable as pseudohalogen. In addition, groups represented by the following formulae (L-1) to (L-5) are also preferable.

In the formulae (L-1) to (L-5), R31 to R57 each independently represent a hydrogen atom, an alkyl group, a cycloalkyl group, a heterocycloalkyl group, an aryl group, a heteroaryl group, an aralkyl group, an alkenyl group, an alkynyl group, or an alkoxy group, where each group is optionally substituted or unsubstituted. Regarding R31 to R33, R34 to R39, R40 to R43, R44 to R49, R50 to R52, R53 to R55, and R56 and R57, independently of one another, parts of adjacent two thereof are optionally bonded and integrated to form a saturated or unsaturated ring structure. In this case, one or more atoms of the ring structure are optionally substituted with an alkyl group or an aryl group (a substituent thereof is optionally further substituted or unsubstituted) and the ring structure optionally forms one or more further ring structures.

Specific examples of the alkyl group, the cycloalkyl group, the heterocycloalkyl group, the aryl group, the heteroaryl group, the aralkyl group, the alkenyl group, the alkynyl group, and the alkoxy group represented by R31 to R57 are the same as the above-described examples of those represented by R1 and R2 in the formula (1).

As the group represented by R31 to R57, a hydrogen atom, an alkyl group, or an aryl group is preferable, and specific examples thereof include a hydrogen atom, a methyl group, an ethyl group, an n-propyl group, an isopropyl group, an n-butyl group, a tert-butyl group, an n-pentyl group, an n-hexyl group, an n-heptyl group, an n-octyl group, a cyclohexyl group, a phenyl group, and a naphthyl group. Among these, a hydrogen atom, a methyl group, a propyl group, or a phenyl group is preferable; a hydrogen atom, a methyl group, or a phenyl group is more preferable; and groups represented by the following formulae (12) to (16) are more preferable.

When parts of adjacent two of R31 to R57 are bonded to form a ring structure, examples of the alkyl group or the aryl group as the substituent which is optionally included in the ring structure are the same as the above-described examples of the substituent which is optionally included in the ring structure in the formula (1).

[Chem. 9]

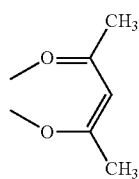

(12)

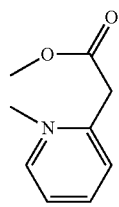

(13)

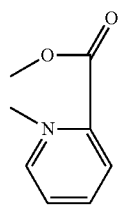

(14)

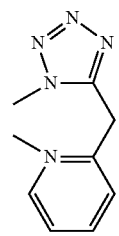

(15)

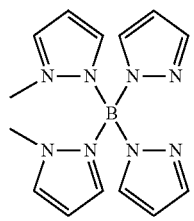

(16)

In the formulae (1) to (7), as K, a phosphine, a phosphonate, and a derivative thereof; an arsenate and a derivative thereof; a phosphite; CO; a pyridine; or a nitrile is preferable, and a group represented by the following formula (K-1) is also preferable.

[Chem. 10]

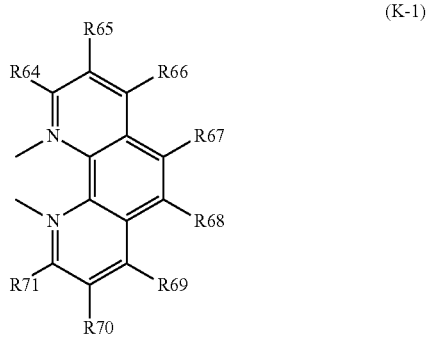

(K-1)

In the formula (K-1), R64 to R71 each independently represent a hydrogen atom, an alkyl group, a cycloalkyl group, a heterocycloalkyl group, an aryl group, a heteroaryl group, an aralkyl group, an alkenyl group, an alkynyl group, or an alkoxy group, where each group is optionally substituted or unsubstituted. Regarding R64 and R71, independently of one another, parts of adjacent two thereof are optionally bonded and integrated to form a saturated or unsaturated ring structure. In this case, one or more atoms of the ring structure are optionally substituted with an alkyl group or an aryl group (a substituent thereof is optionally further substituted or unsubstituted) and the ring structure optionally forms one or more further ring structures.

Specific examples of the alkyl group, the cycloalkyl group, the heterocycloalkyl group, the aryl group, the heteroaryl group, the aralkyl group, the alkenyl group, the alkynyl group, and the alkoxy group represented by R64 to R71 are the same as the above-described examples of those represented by R1 and R2 in the formula (1).

As the group represented by R64 to R71, a hydrogen atom, an alkyl group, or an aryl group is preferable, and specific examples thereof include a hydrogen atom, a methyl group, an ethyl group, an n-propyl group, an isopropyl group, an n-butyl group, a tert-butyl group, an n-pentyl group, an n-hexyl group, an n-heptyl group, an n-octyl group, a cyclohexyl group, a phenyl group, and a naphthyl group. Among these, a hydrogen atom, a methyl group, or a phenyl group is preferable; and 5-methyl-1,10-phenanthroline represented by the following formula (17) is more preferable.

In addition, when parts of adjacent two of R64 to R71 are bonded to form a ring structure, examples of the alkyl group or the aryl group as the substituent which is optionally included in the ring structure are the same as the above-described examples of the substituent which is optionally included in the ring structure in the formula (1).

[Chem. 11]

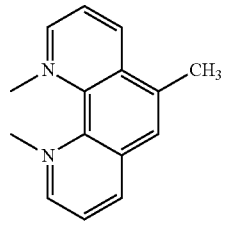

(17)

Hereinafter, specific preferable examples of the transition metal complex according to the embodiment will be shown, but the embodiment is not limited to these examples. In the following examples, geometric isomers are not particularly distinguished, and the transition metal complex according the embodiment contains all the geometric isomers. In the following examples, "OAc$^-$" represents an acetyl oxyanion.

[Chem. 12]

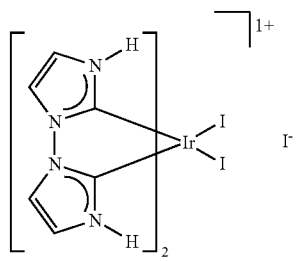

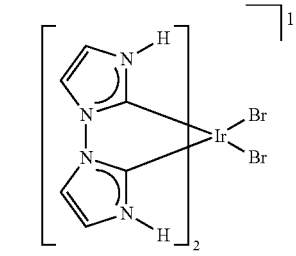

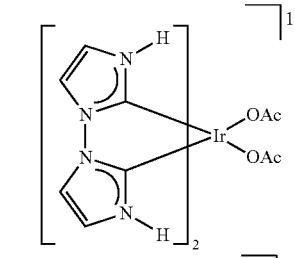

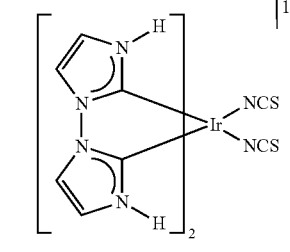

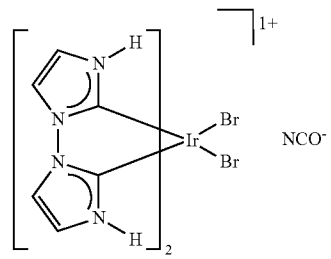

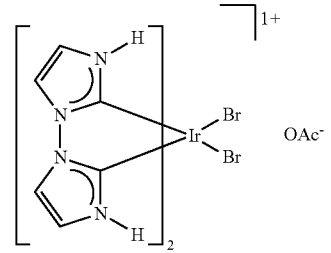

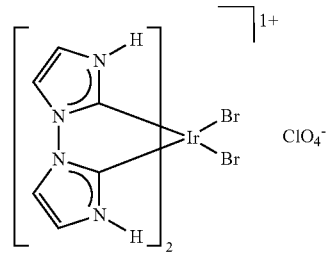

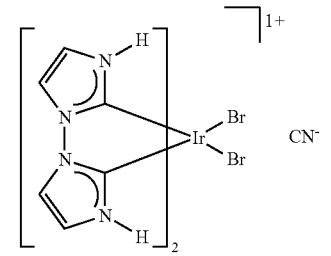

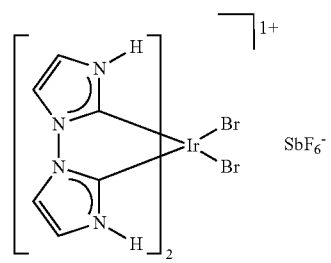

[Chem. 13]

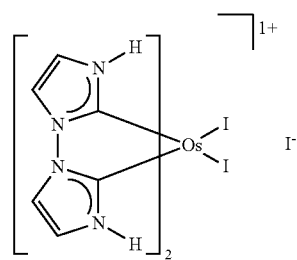

-continued
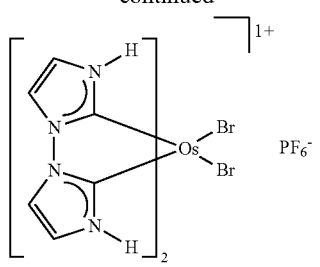 PF6−
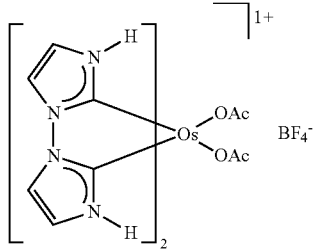 BF4−
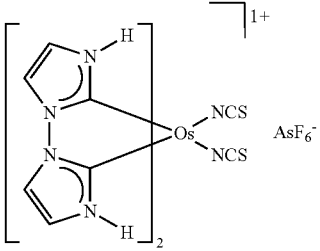 AsF6−
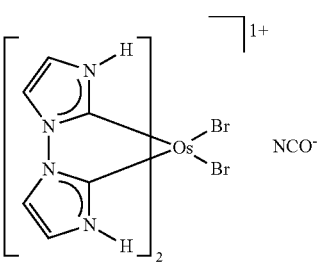 NCO−
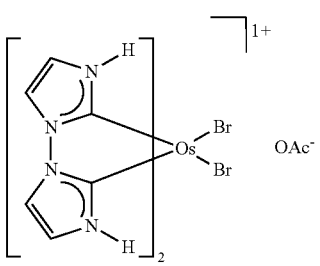 OAc−
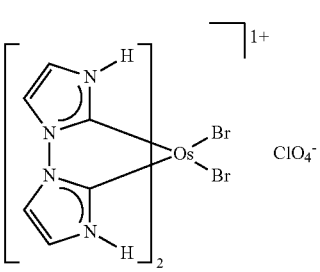 ClO4−
-continued
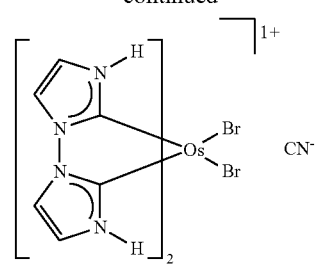 CN−
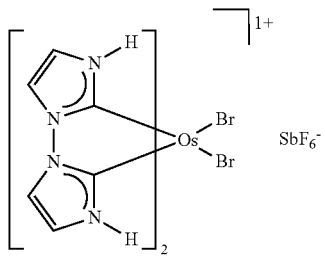 SbF6−
[Chem. 14]
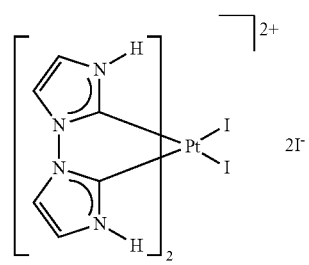 2I−
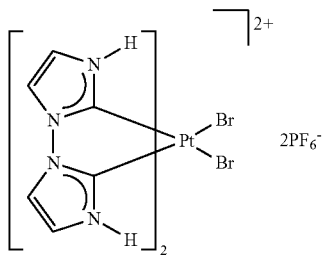 2PF6−
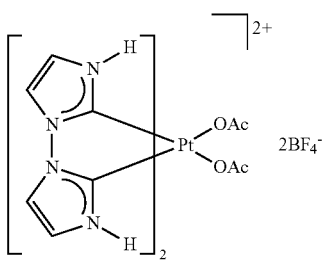 2BF4−
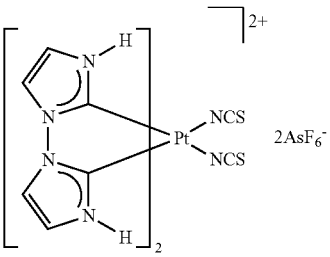 2AsF6−

23
-continued
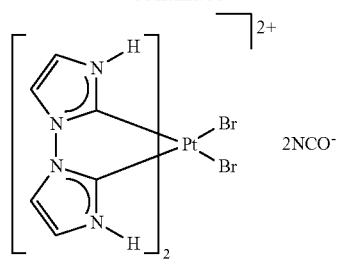 2NCO⁻
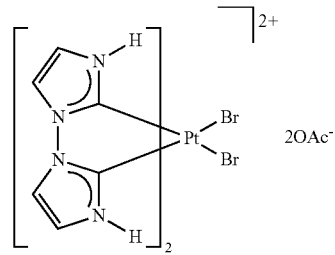 2OAc⁻
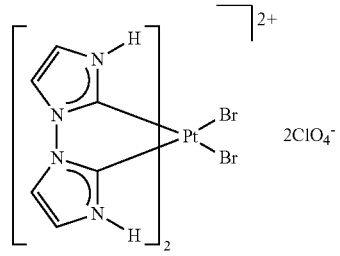 2ClO₄⁻
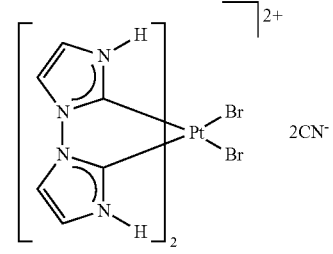 2CN⁻
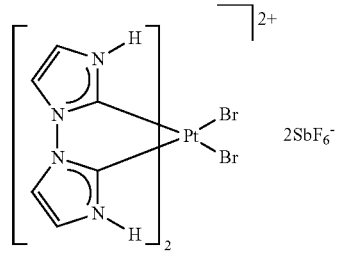 2SbF₆⁻
[Chem. 15]
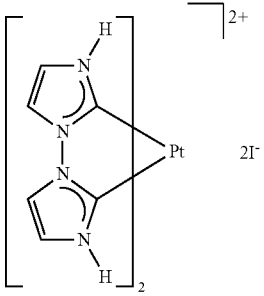 2I⁻
24
-continued
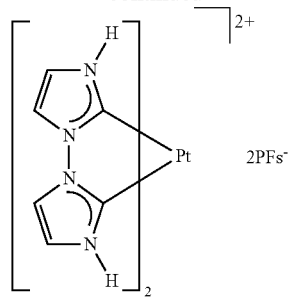 2PF₆⁻
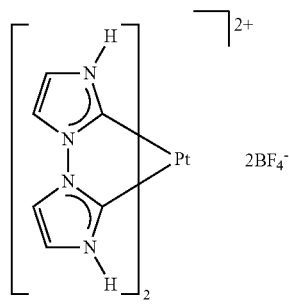 2BF₄⁻
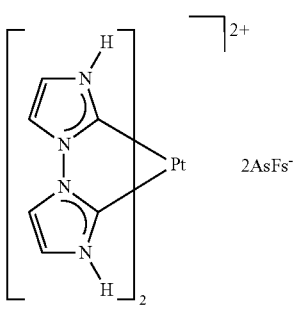 2AsF₆⁻
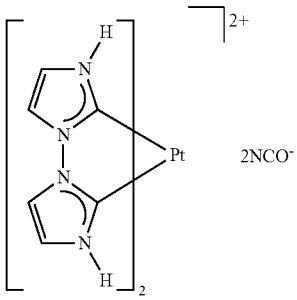 2NCO⁻
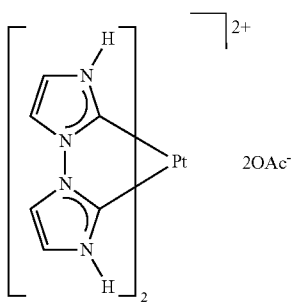 2OAc⁻

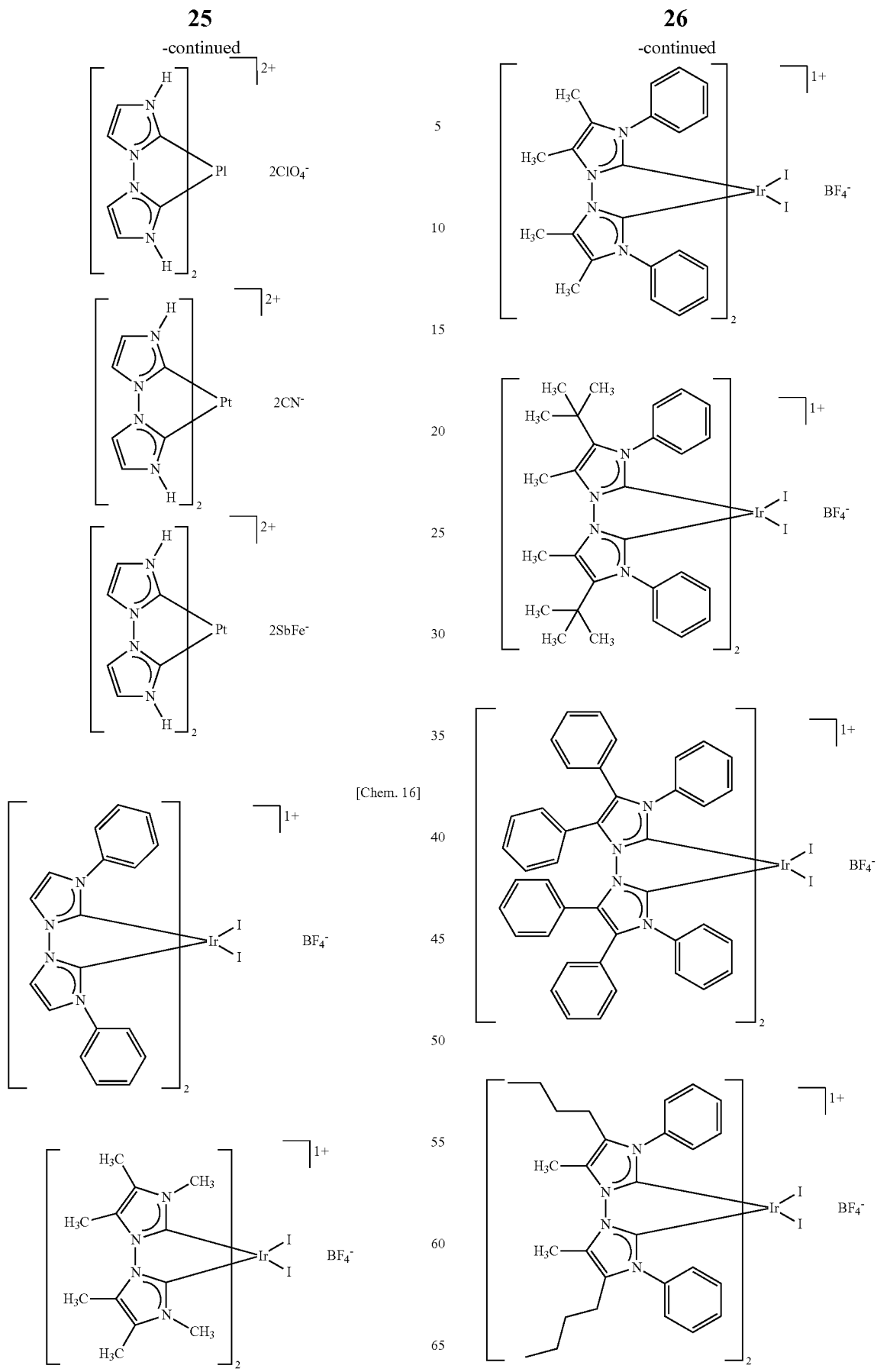

[Chem. 17]
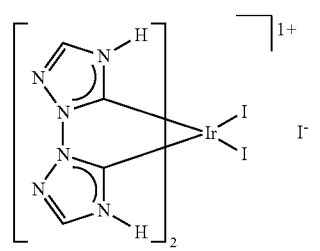# 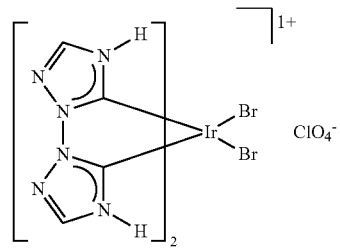
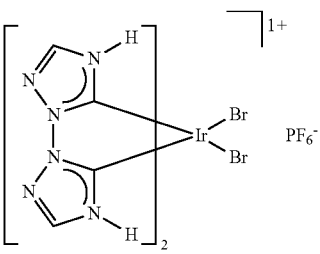# 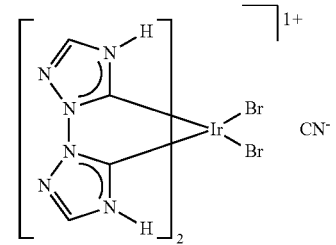
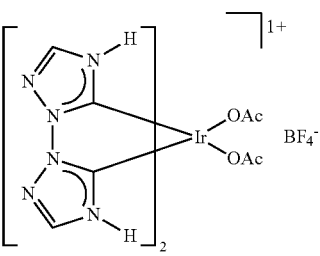# 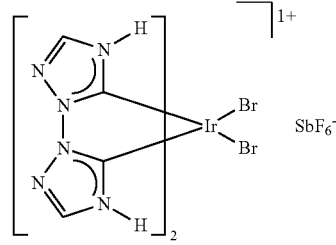
[Chem. 18]
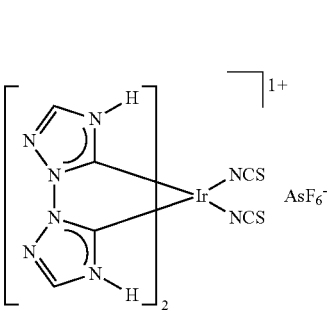# 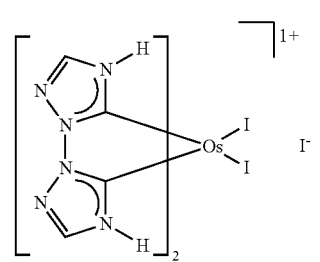
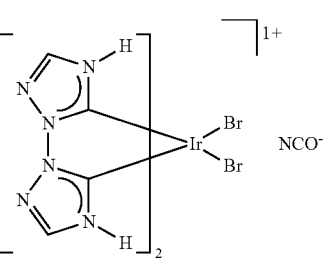# 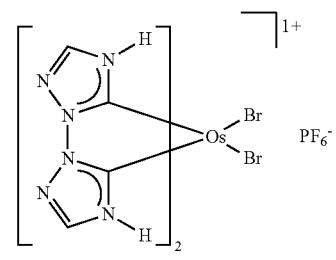
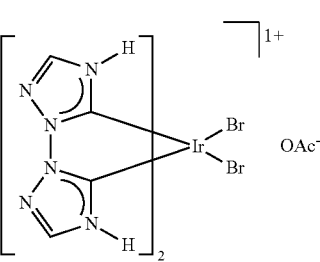

29
-continued
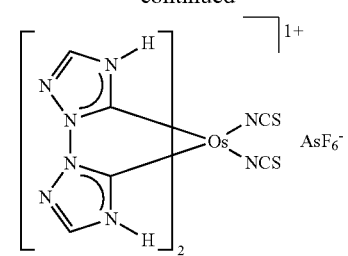 AsF6-
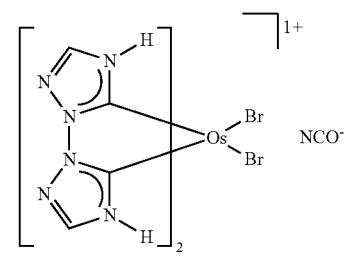 NCO-
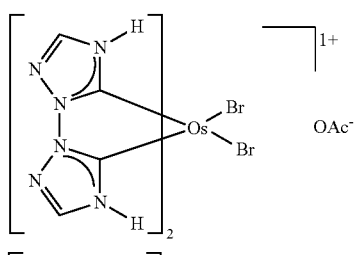 OAc-
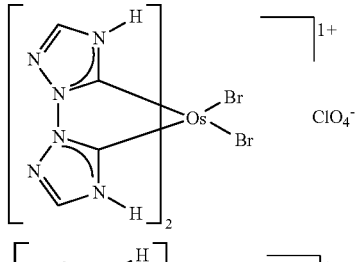 ClO4-
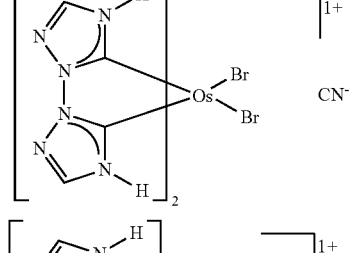 CN-
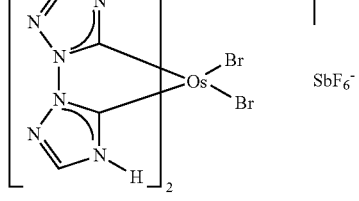 SbF6-
[Chem. 19]
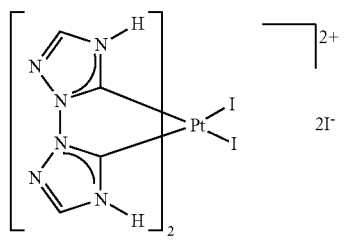 2I-
30
-continued
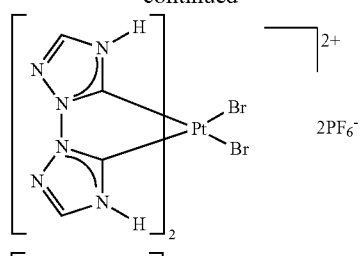 2PF6-
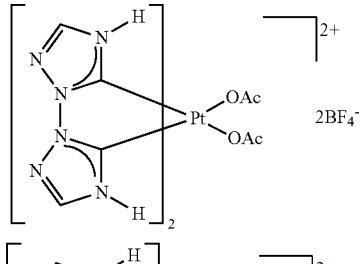 2BF4-
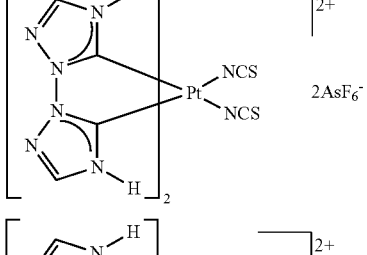 2AsF6-
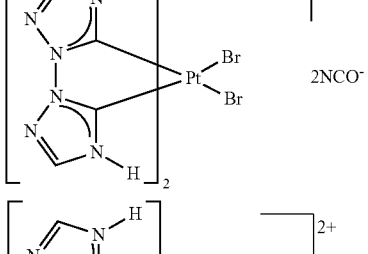 2NCO-
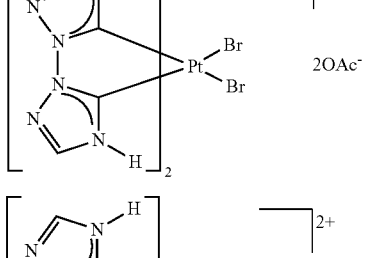 2OAc-
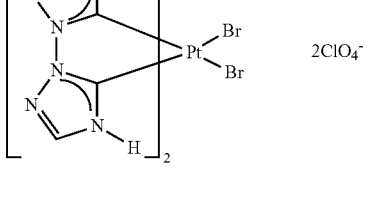 2ClO4-
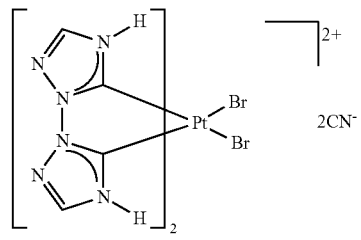 2CN- -continued
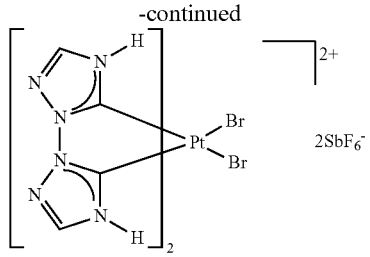 2SbF$_6^-$
[Chem. 20]
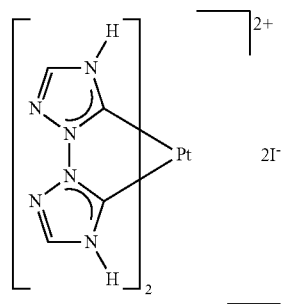 2I$^-$
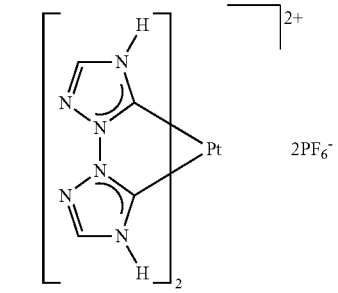 2PF$_6^-$
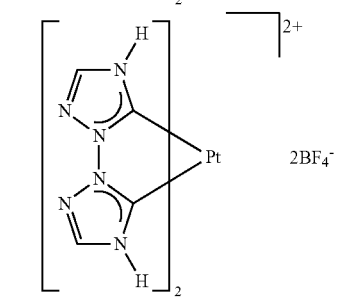 2BF$_4^-$
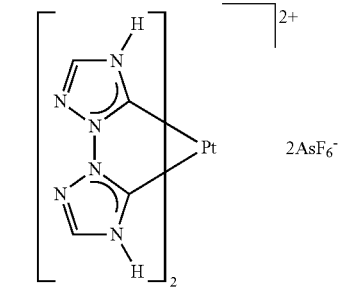 2AsF$_6^-$
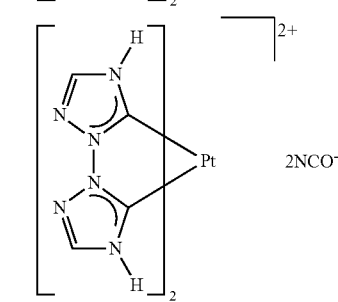 2NCO$^-$
-continued
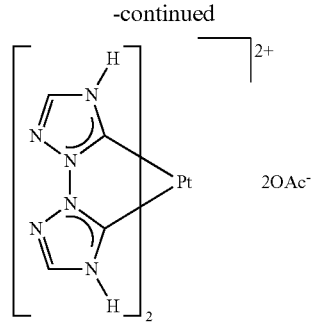 2OAc$^-$
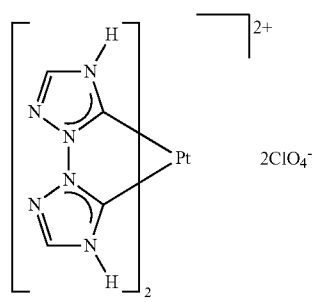 2ClO$_4^-$
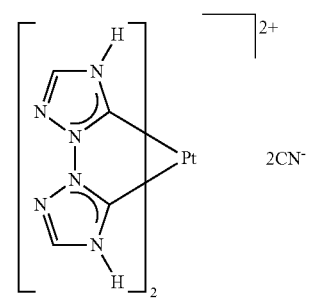 2CN$^-$
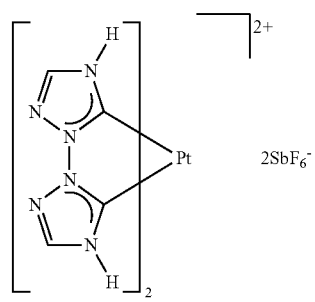 2SbF$_6^-$
[Chem. 21]
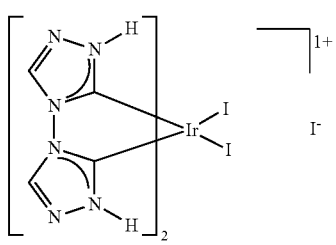 I$^-$
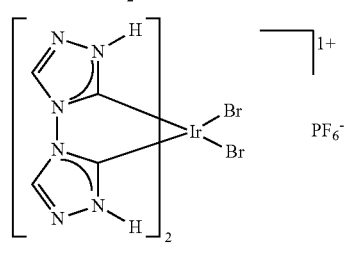 PF$_6^-$ -continued
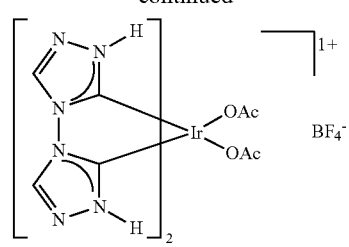 BF₄⁻
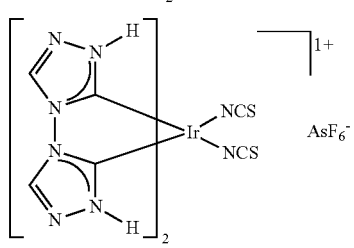 AsF₆⁻
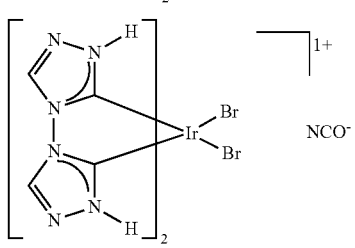 NCO⁻
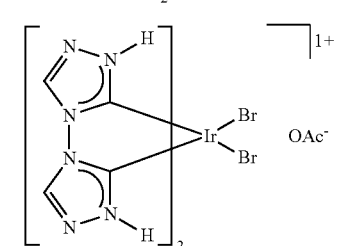 OAc⁻
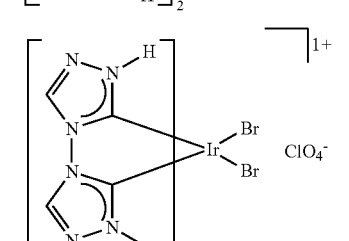 ClO₄⁻
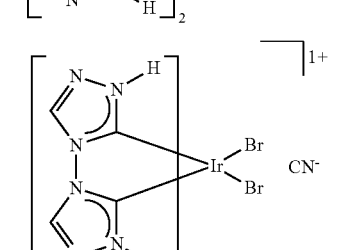 CN⁻
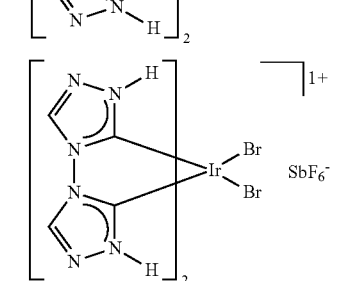 SbF₆⁻
-continued
[Chem. 22]
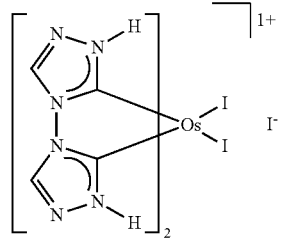 I⁻
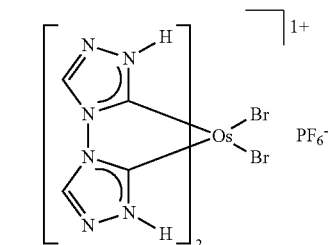 PF₆⁻
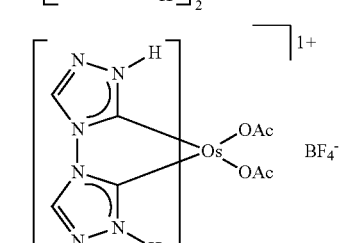 BF₄⁻
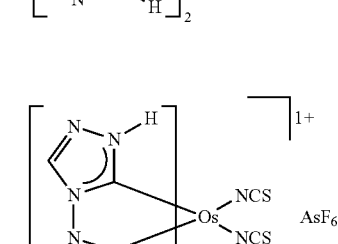 AsF₆⁻
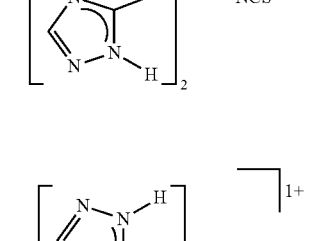 NCO⁻
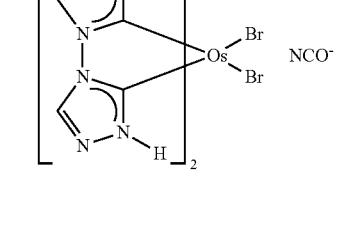 OAc⁻

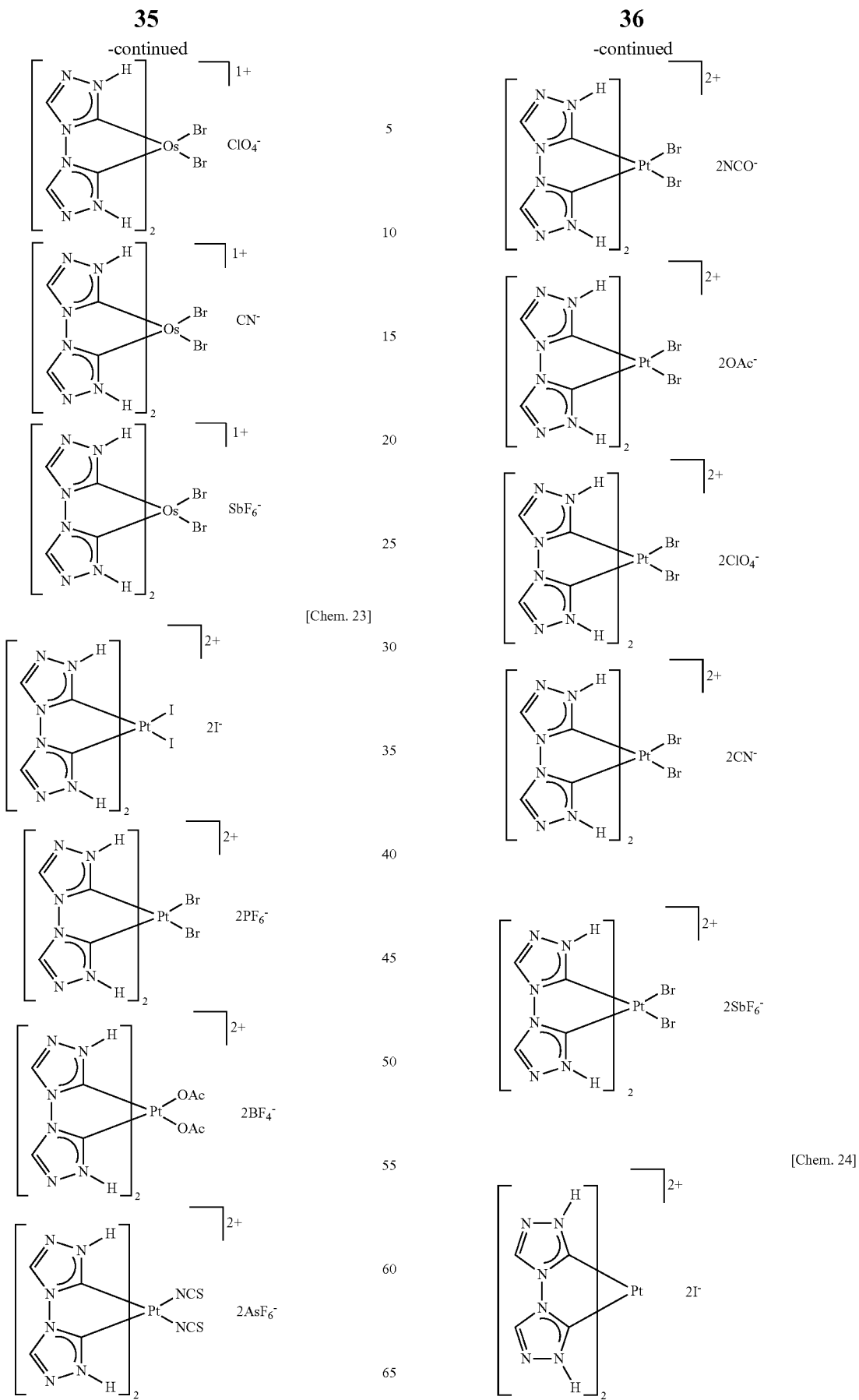

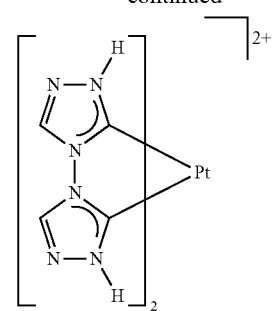 2PF6-
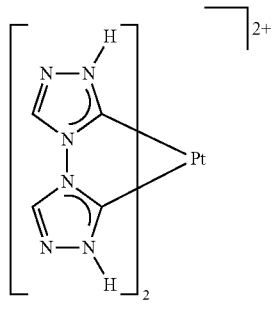 2BF4-
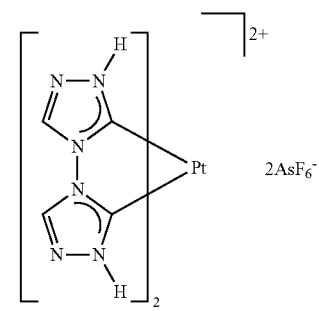 2AsF6-
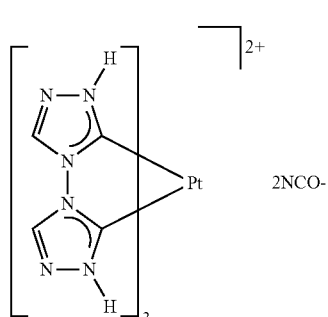 2NCO-
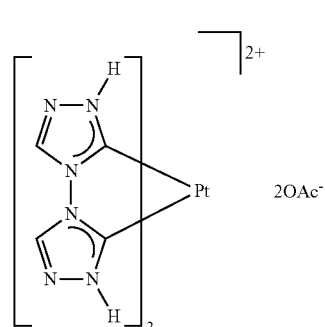 2OAc-
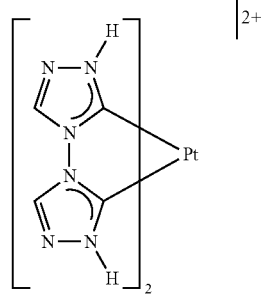 2ClO4-
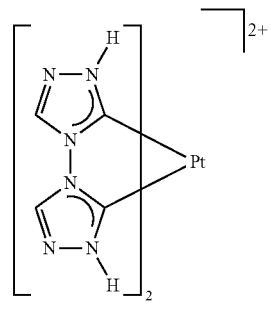 2CN-
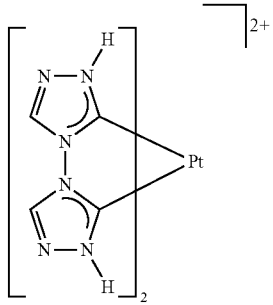 2SbF6-
[Chem. 25]
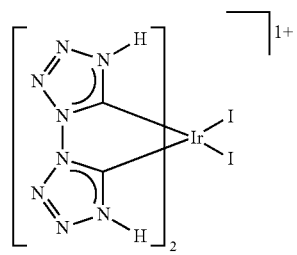 I-
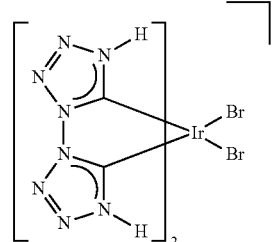 PF6-
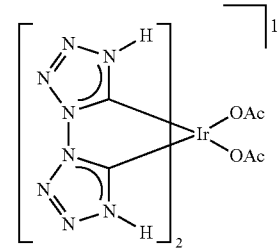 BF4-

[Chem. 26]
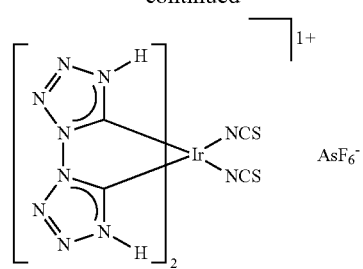 AsF$_6^-$
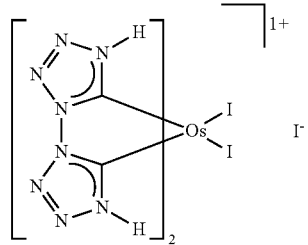 I$^-$
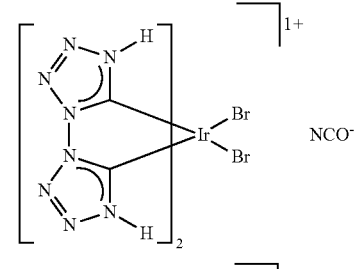 NCO$^-$
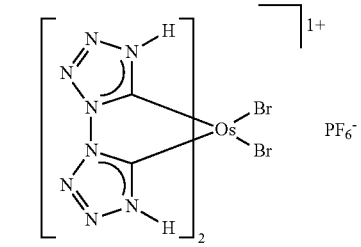 PF$_6^-$
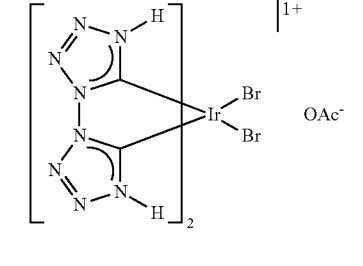 OAc$^-$
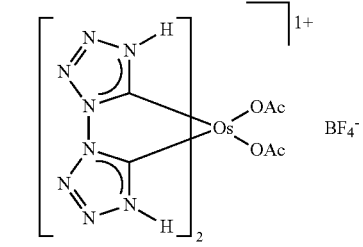 BF$_4^-$
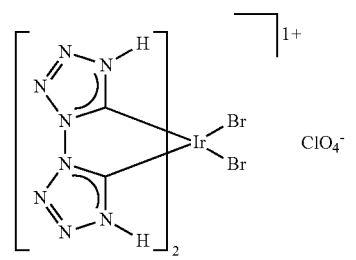 ClO$_4^-$
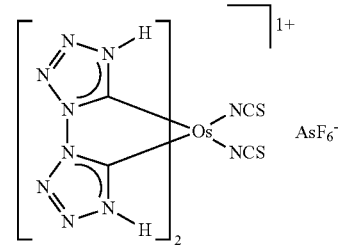 AsF$_6^-$
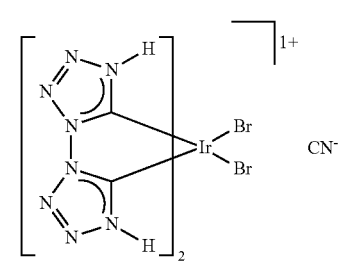 CN$^-$
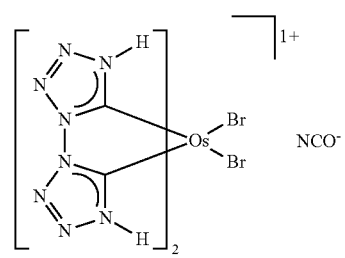 NCO$^-$
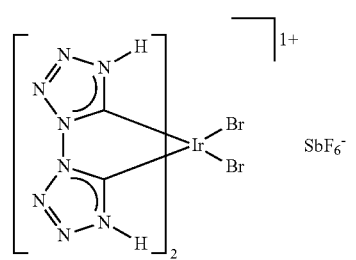 SbF$_6^-$
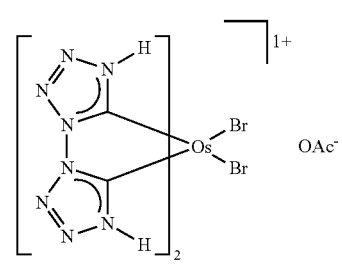 OAc$^-$

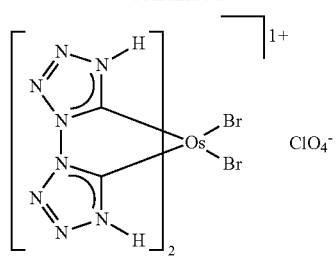 ClO4-
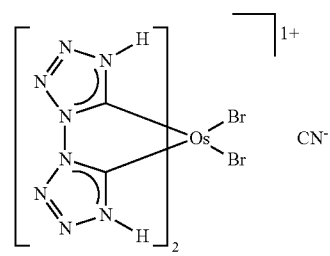 CN-
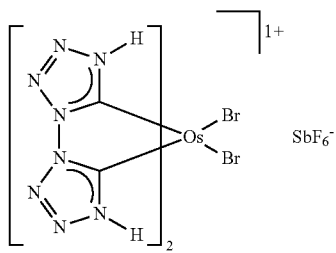 SbF6-
[Chem. 27]
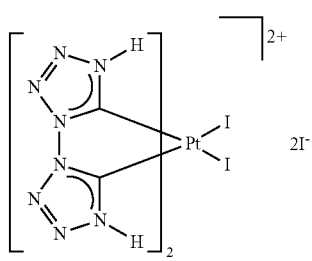 2I-
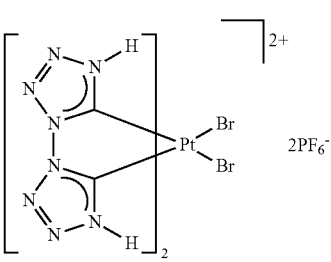 2PF6-
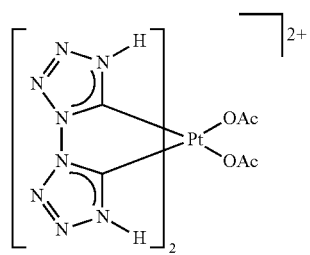 2BF4-
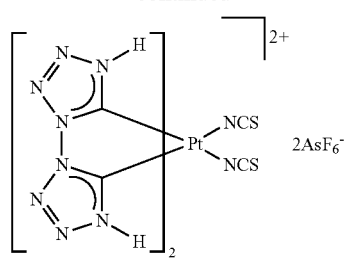 2AsF6-
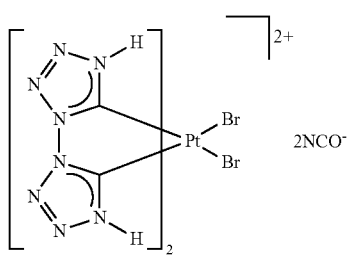 2NCO-
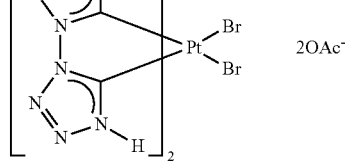 2OAc-
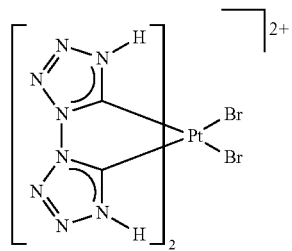 2ClO4-
2CN-
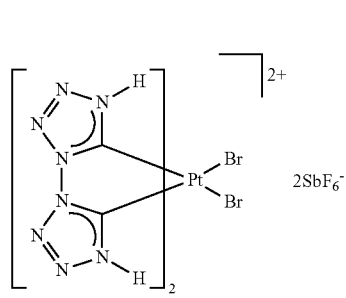 2SbF6-

[Chem. 28]
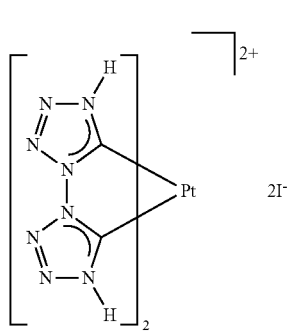 2I⁻
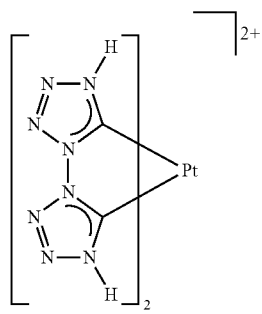 2PF₆⁻
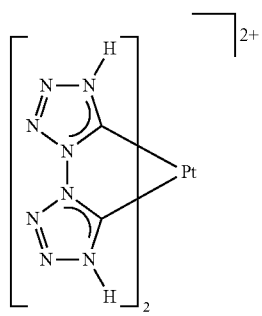 2BF₄⁻
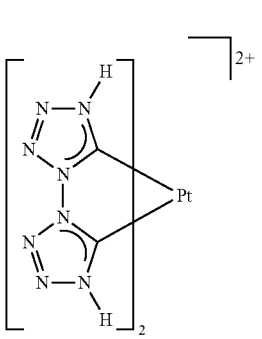 2AsF₆⁻
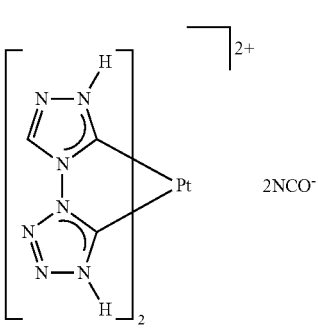 2NCO⁻
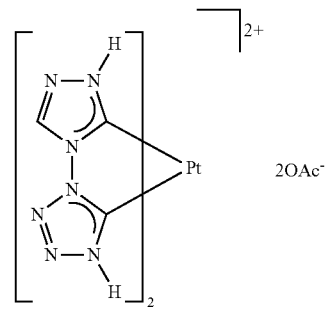 2OAc⁻
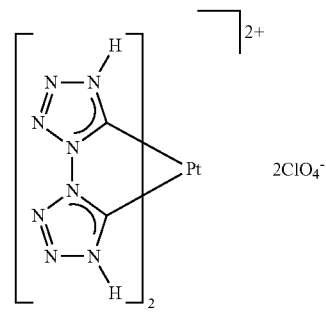 2ClO₄⁻
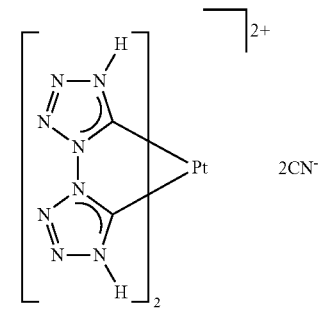 2CN⁻
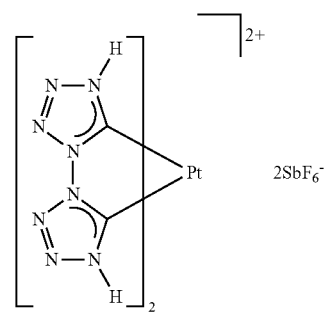 2SbF₆⁻
[Chem. 29]
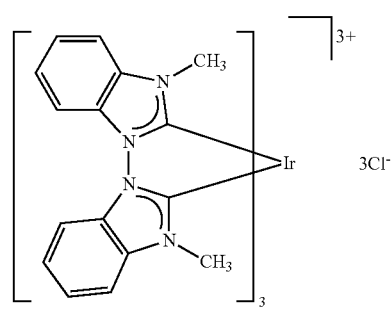 3Cl⁻

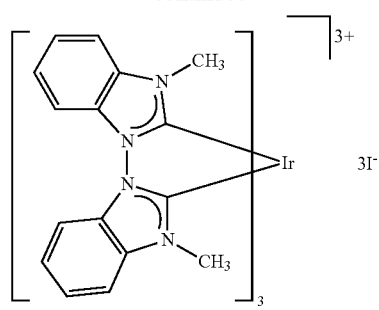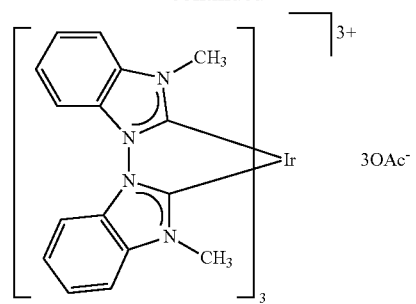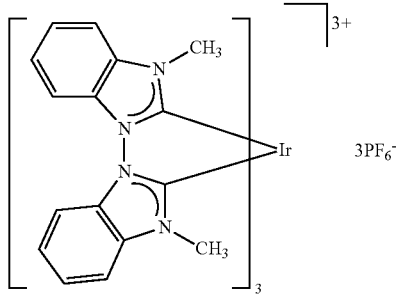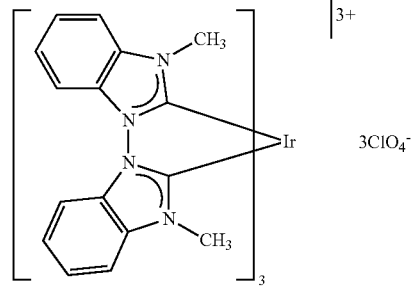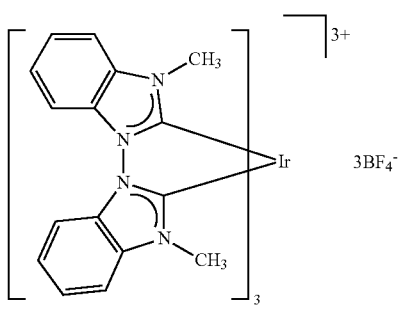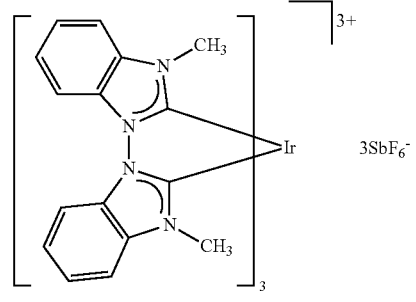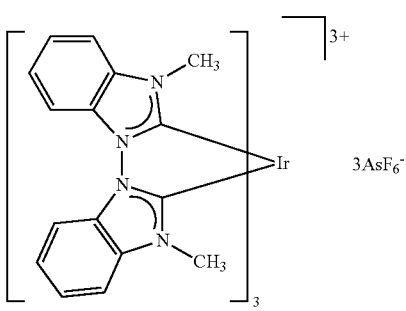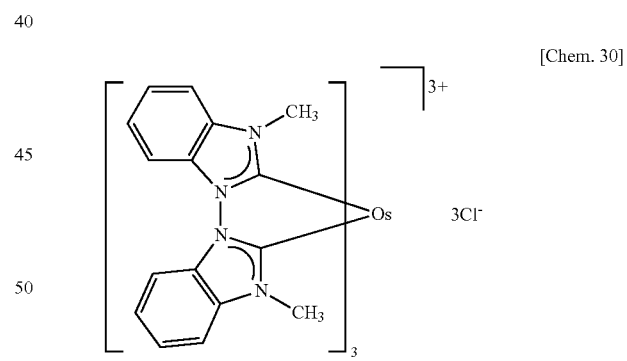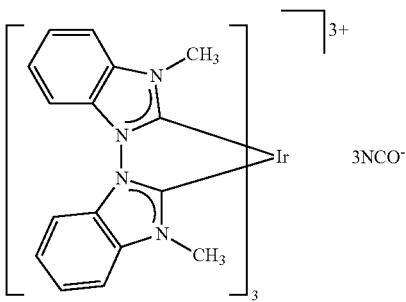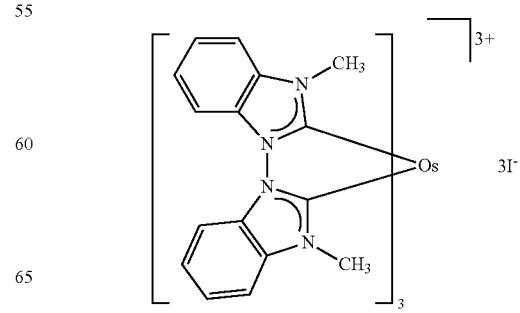

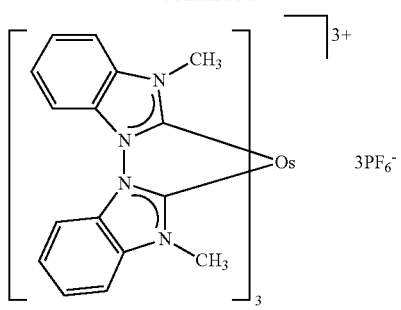
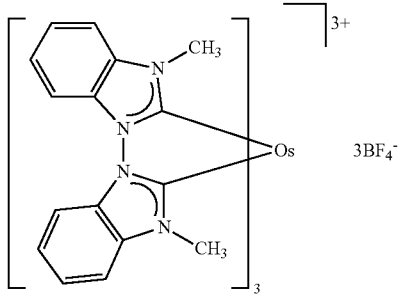
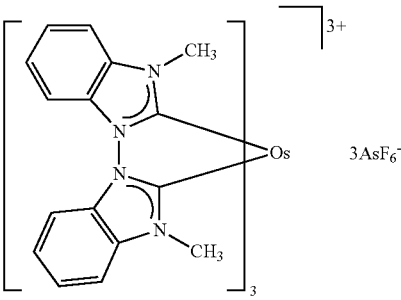
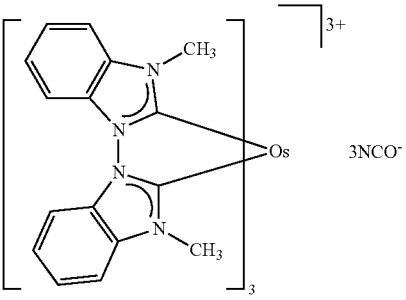
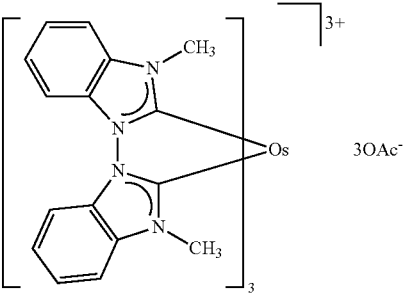
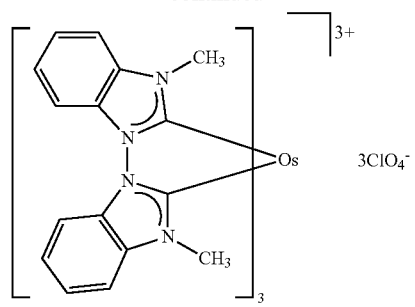
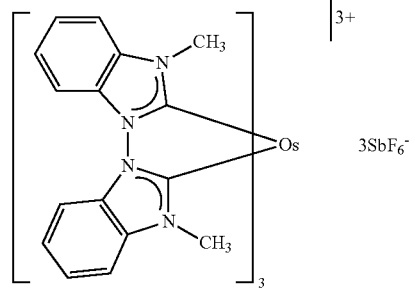
[Chem. 31]
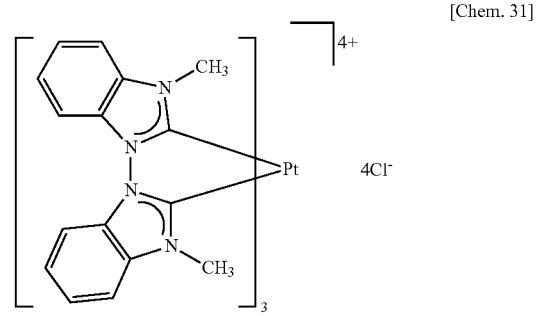
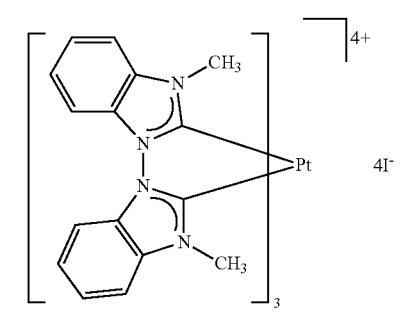
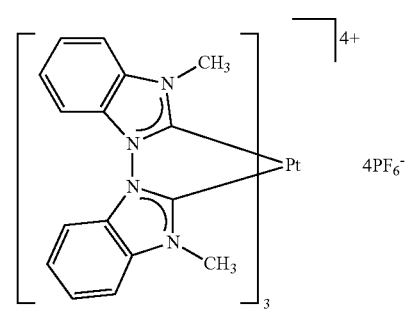

-continued
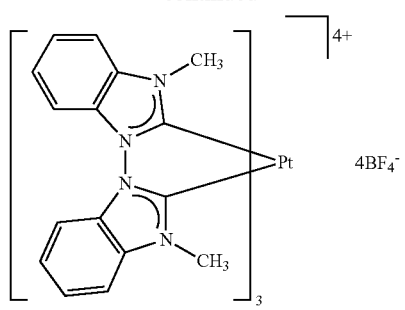 4BF$_4^-$
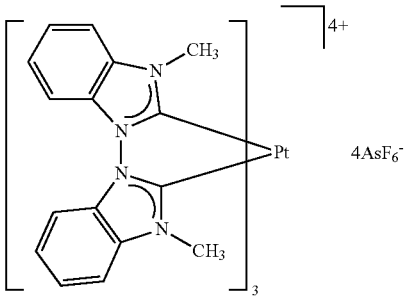 4AsF$_6^-$
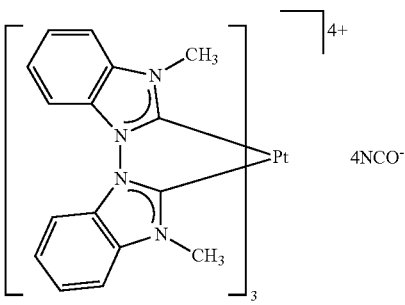 4NCO$^-$
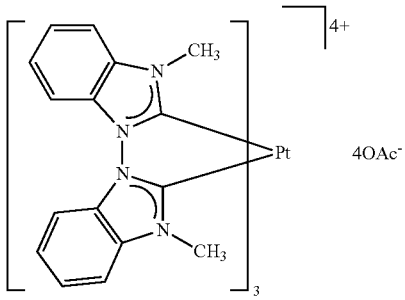 4OAc$^-$
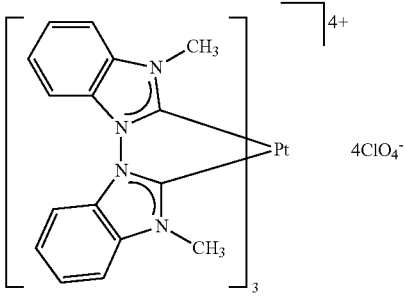 4ClO$_4^-$
-continued
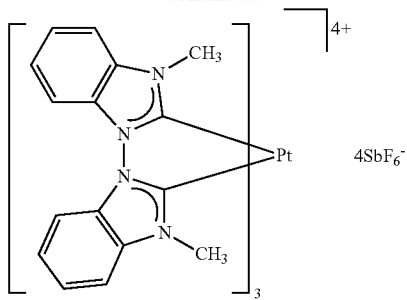 4SbF$_6^-$
[Chem. 32]
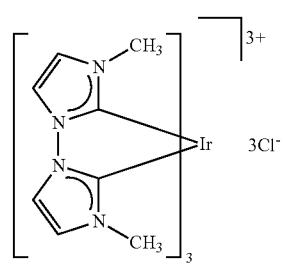 3Cl$^-$
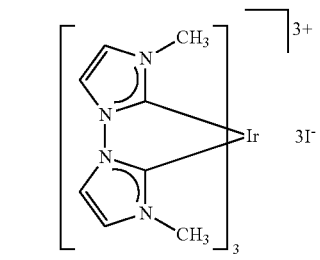 3I$^-$
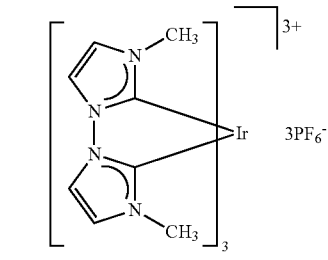 3PF$_6^-$
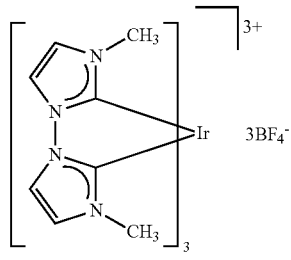 3BF$_4^-$
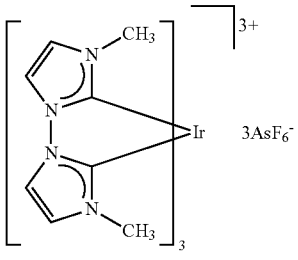 3AsF$_6^-$

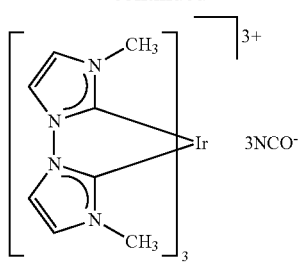 3NCO⁻
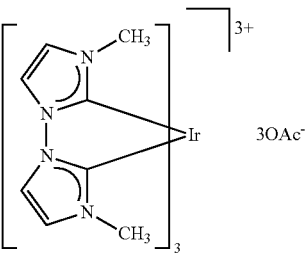 3OAc⁻
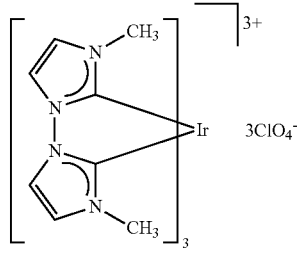 3ClO₄⁻
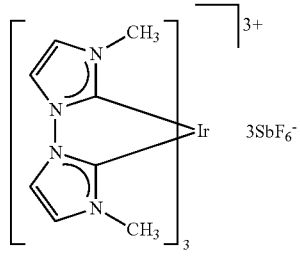 3SbF₆⁻
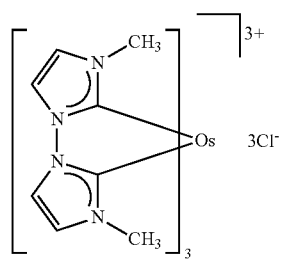 3Cl⁻
[Chem. 33]
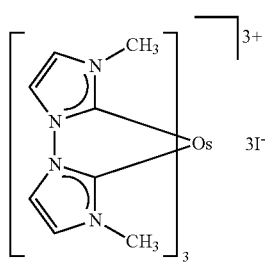 3I⁻
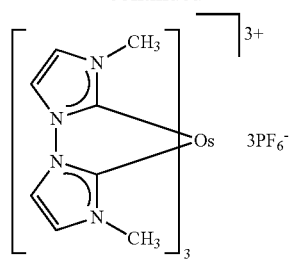 3PF₆⁻
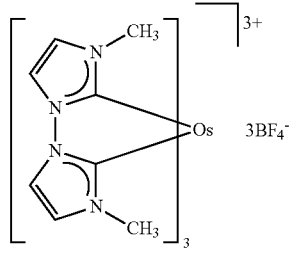 3BF₄⁻
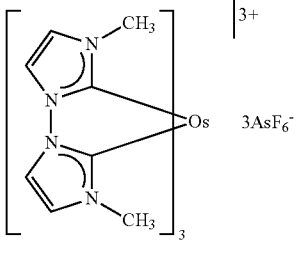 3AsF₆⁻
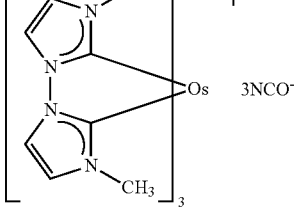 3NCO⁻
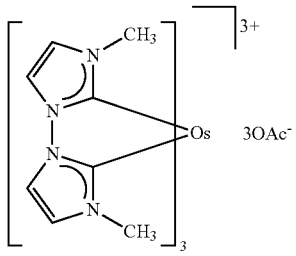 3OAc⁻
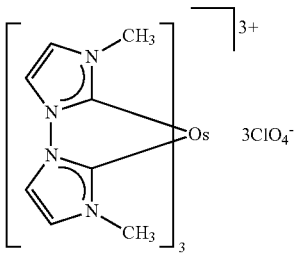 3ClO₄⁻

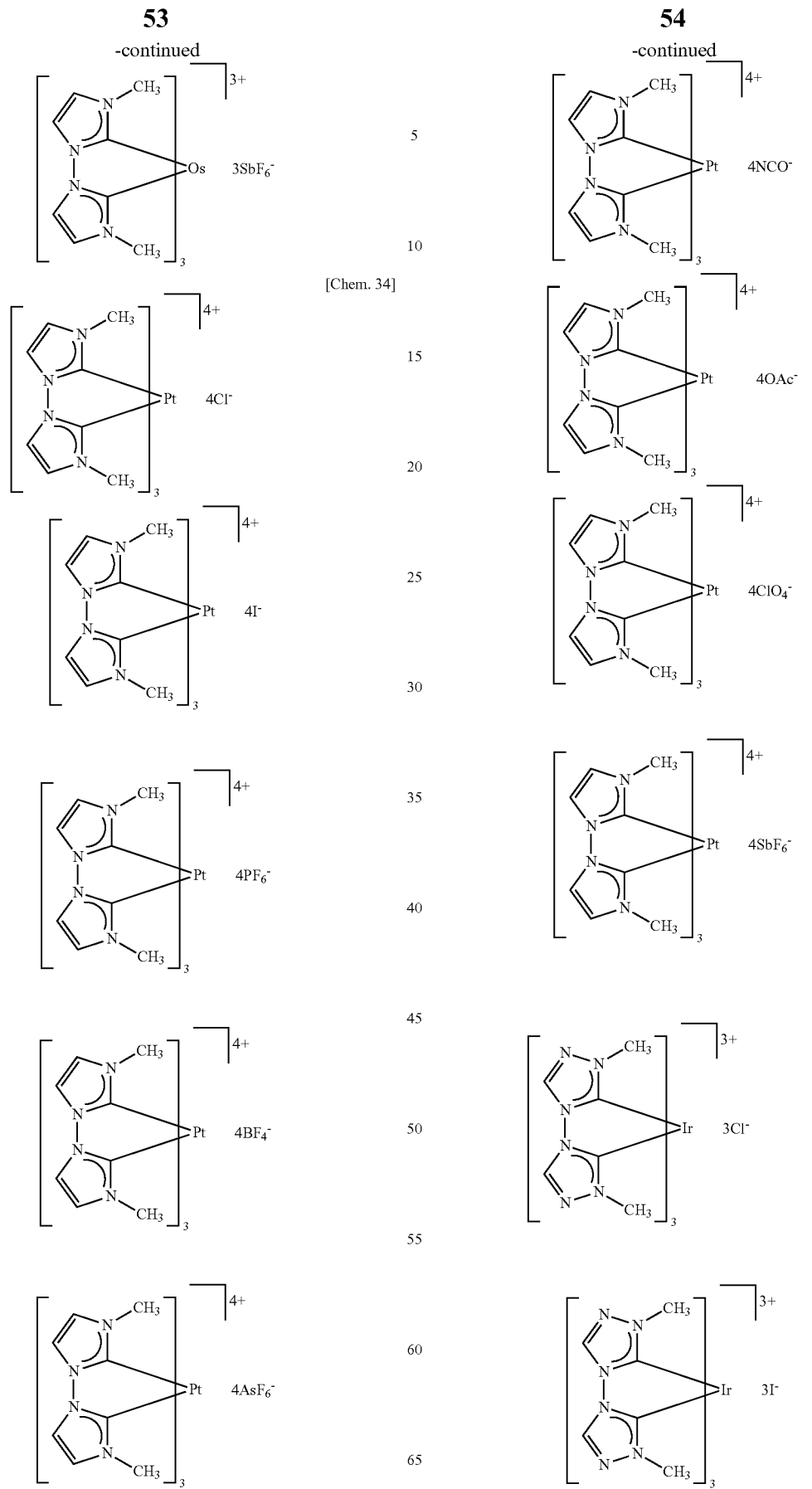

55
-continued
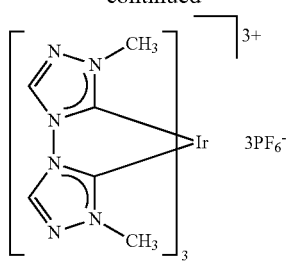 3PF6−
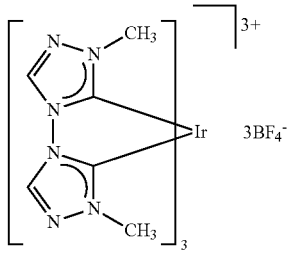 3BF4−
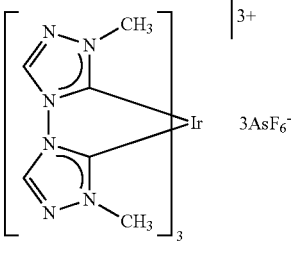 3AsF6−
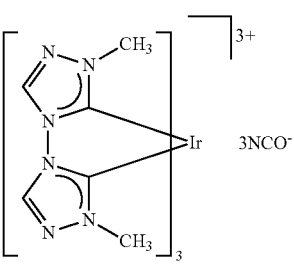 3NCO−
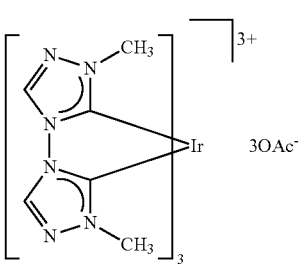 3OAc−
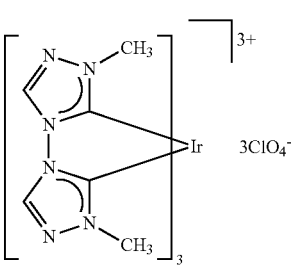 3ClO4−
56
-continued
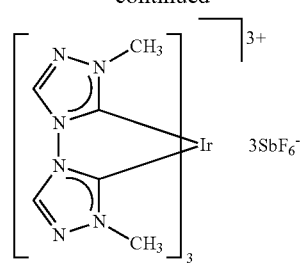 3SbF6−
[Chem. 36]
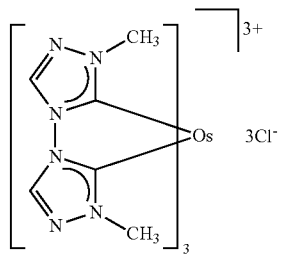 3Cl−
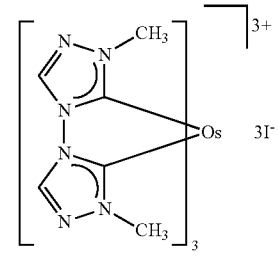 3I−
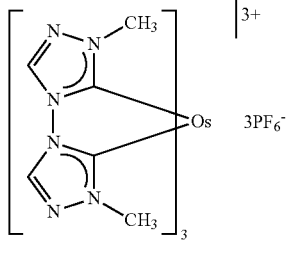 3PF6−
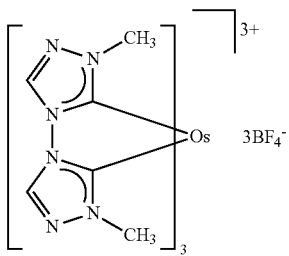 3BF4−
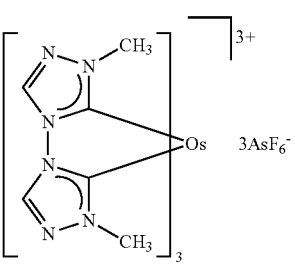 3AsF6−

57
-continued
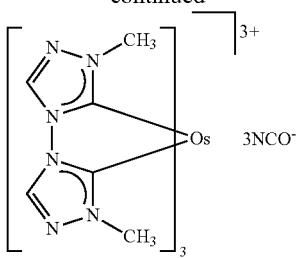 3NCO⁻
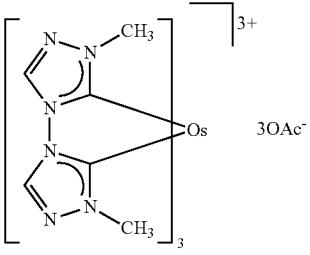 3OAc⁻
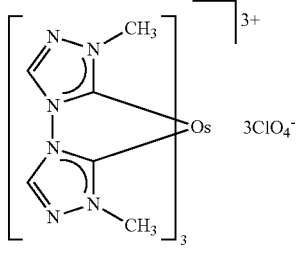 3ClO₄⁻
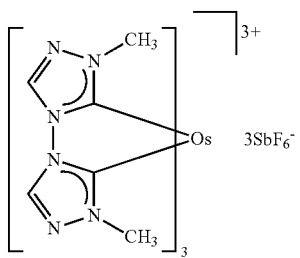 3SbF₆⁻
[Chem. 37]
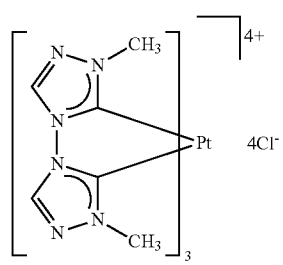 4Cl⁻
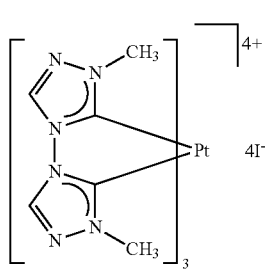 4I⁻
58
-continued
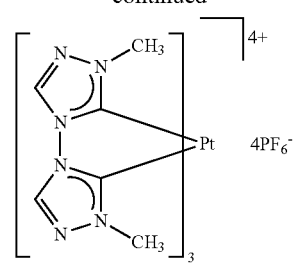 4PF₆⁻
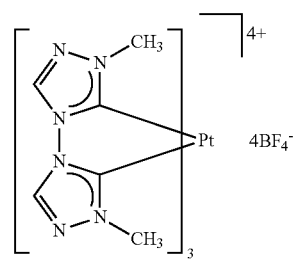 4BF₄⁻
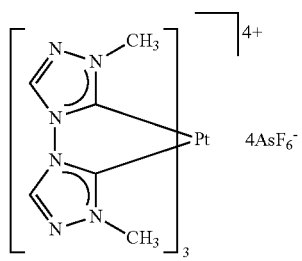 4AsF₆⁻
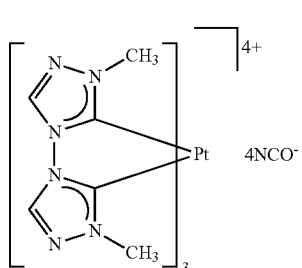 4NCO⁻
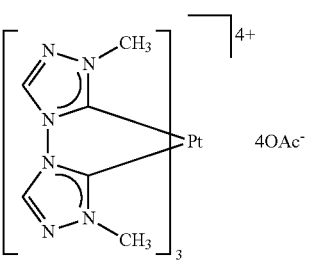 4OAc⁻
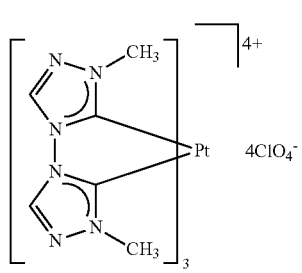 4ClO₄⁻

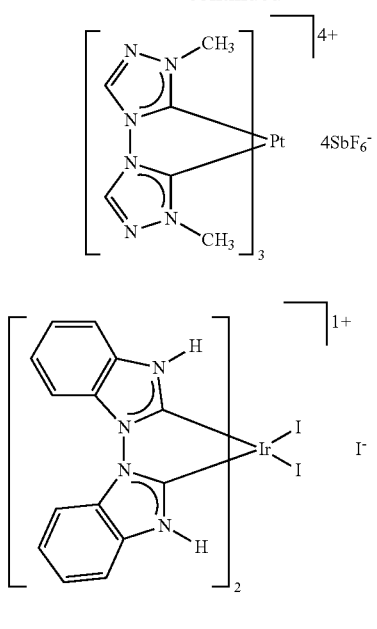
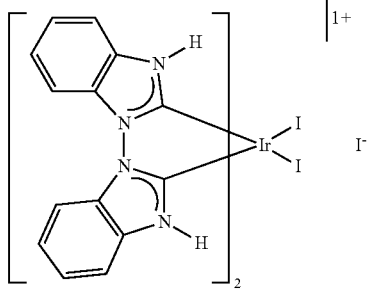
[Chem. 38]
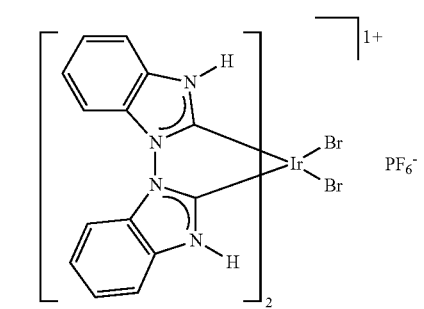
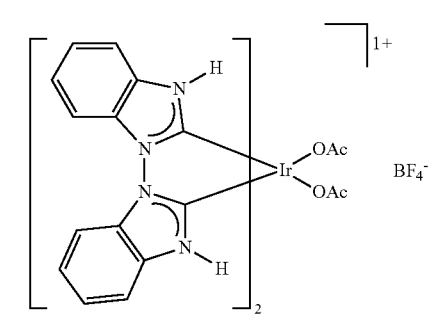
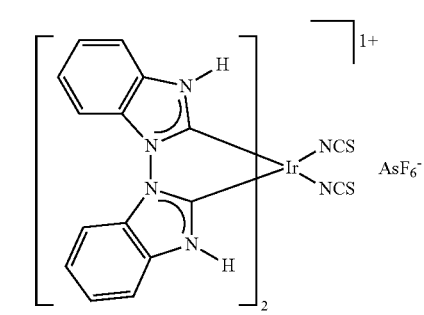
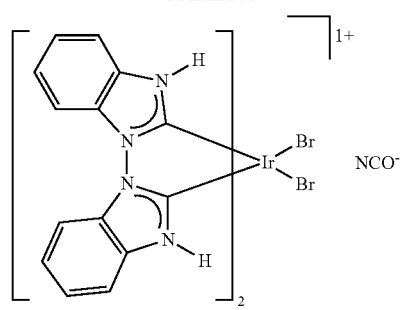
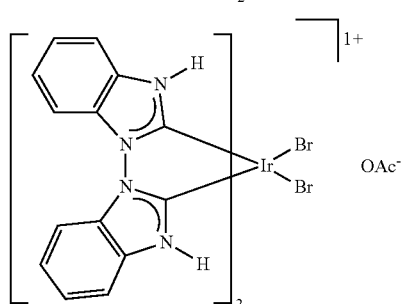
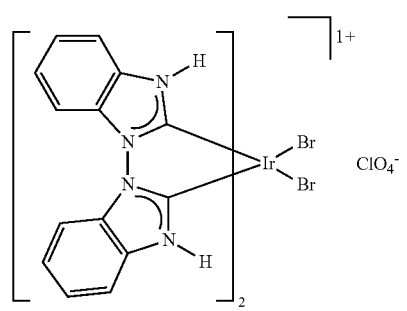
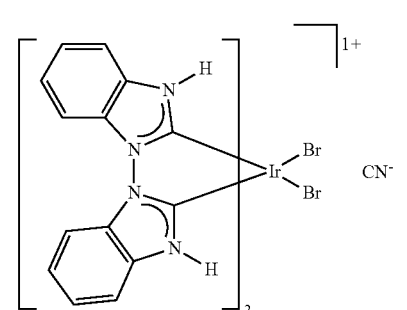
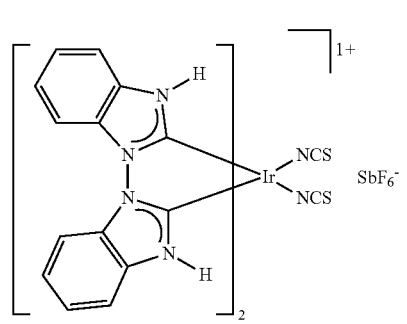

-continued
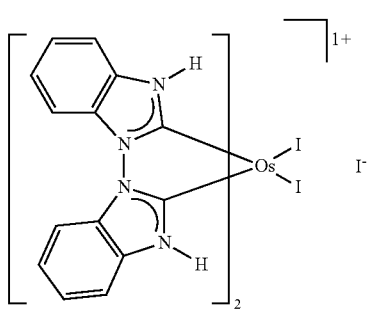 I⁻
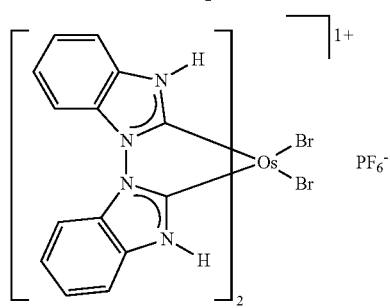 PF₆⁻
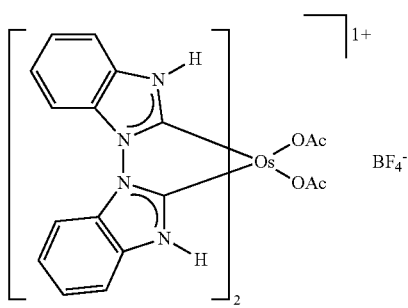 BF₄⁻
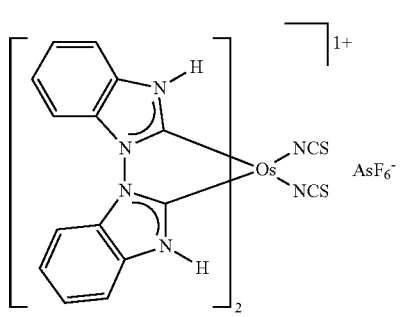 AsF₆⁻
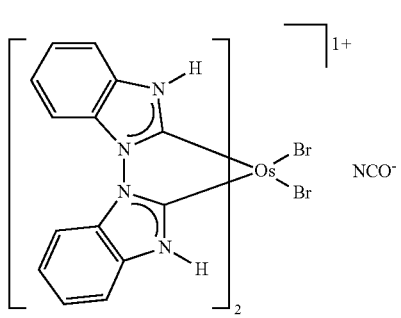 NCO⁻
-continued
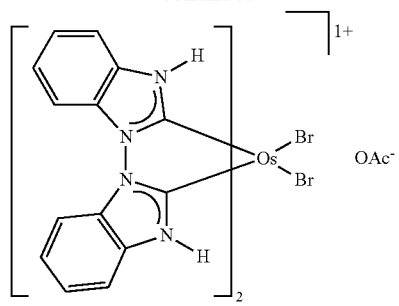 OAc⁻
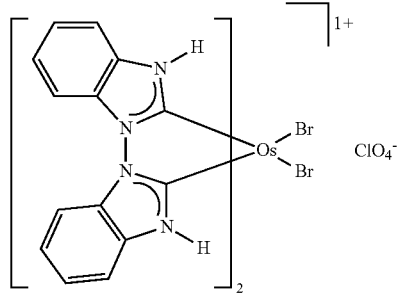 ClO₄⁻
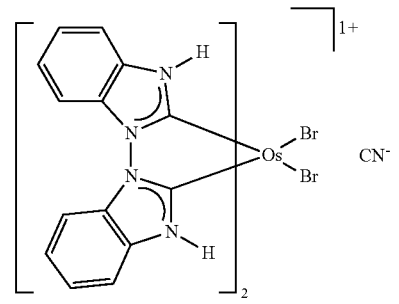 CN⁻
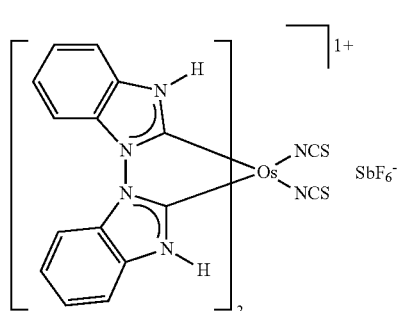 SbF₆⁻
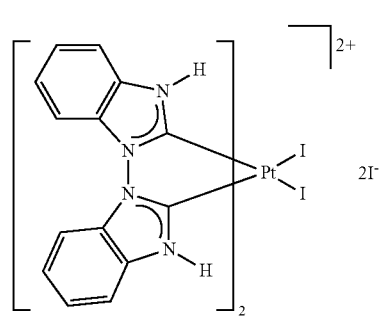 2I⁻

63
-continued
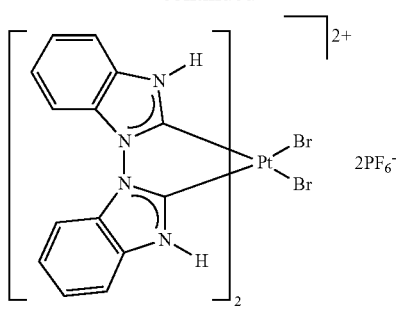
2PF$_6^-$
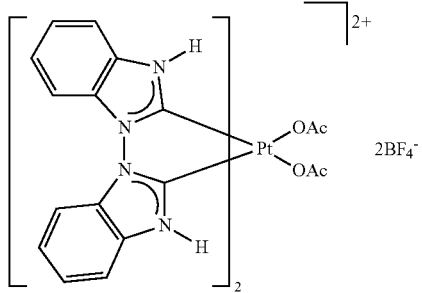
2BF$_4^-$
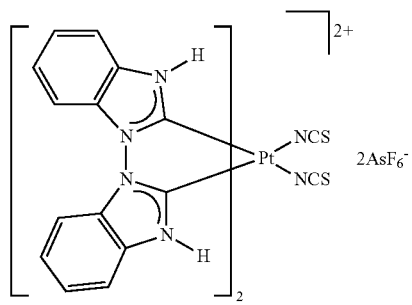
2AsF$_6^-$
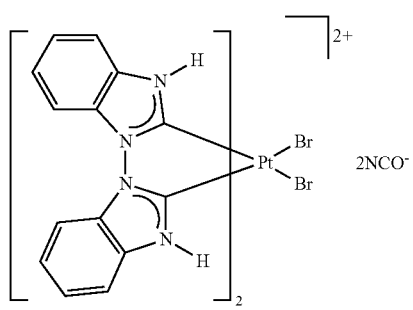
2NCO$^-$
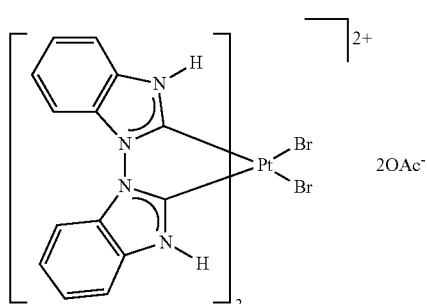
2OAc$^-$
64
-continued
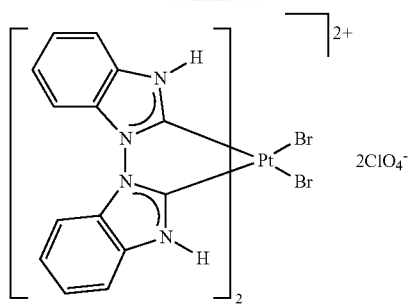
2ClO$_4^-$
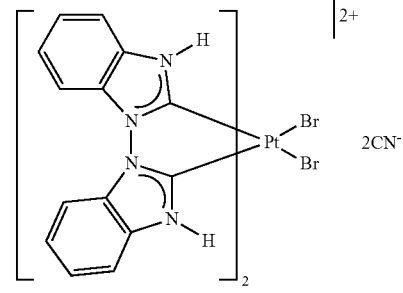
2CN$^-$
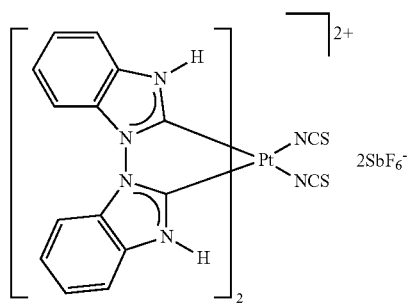
2SbF$_6^-$
[Chem. 41]
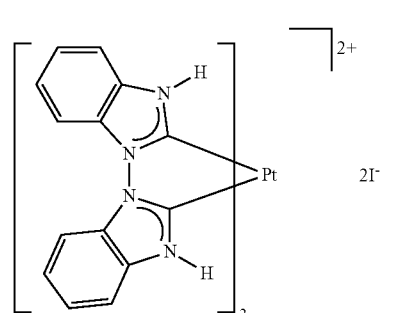
2I$^-$
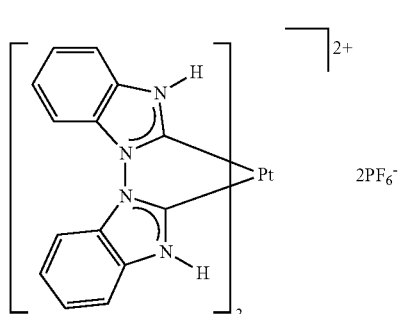
2PF$_6^-$

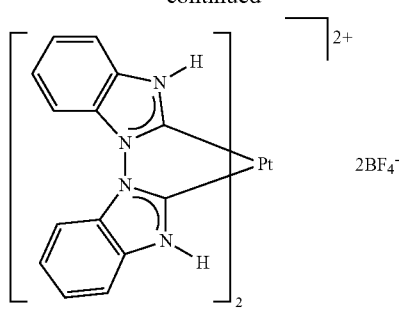 2BF$_4^-$
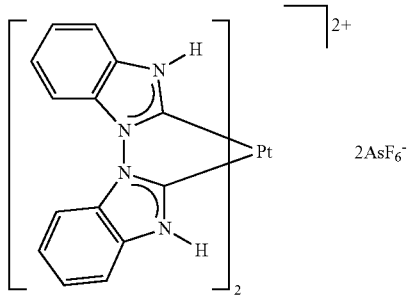 2AsF$_6^-$
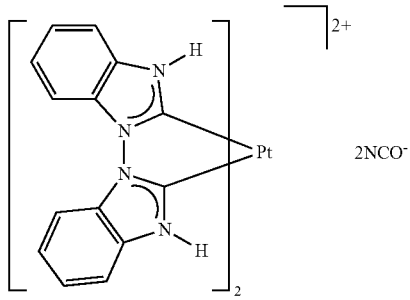 2NCO$^-$
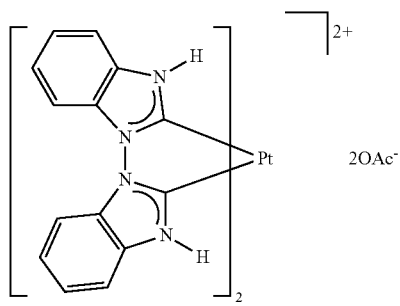 2OAc$^-$
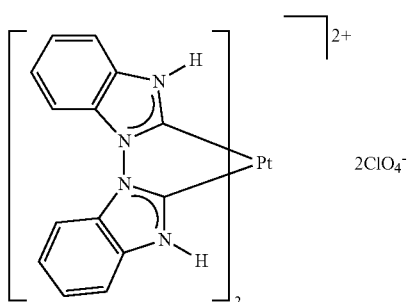 2ClO$_4^-$
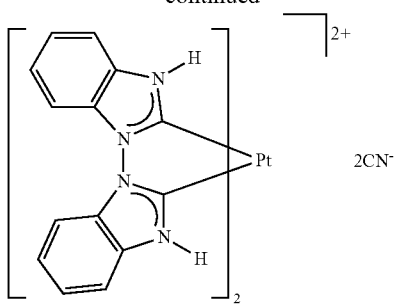 2CN$^-$
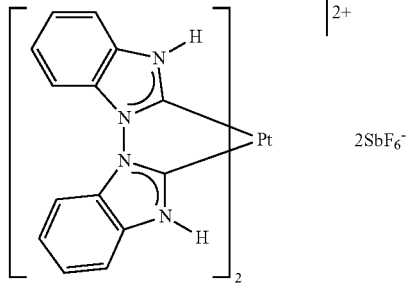 2SbF$_6^-$
[Chem. 42]
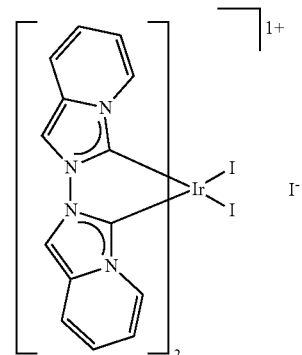 I$^-$
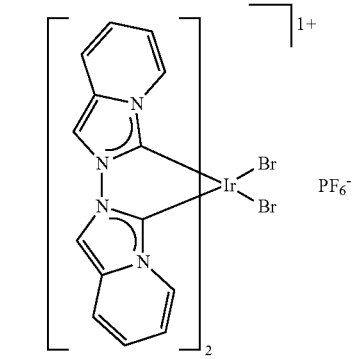 PF$_6^-$
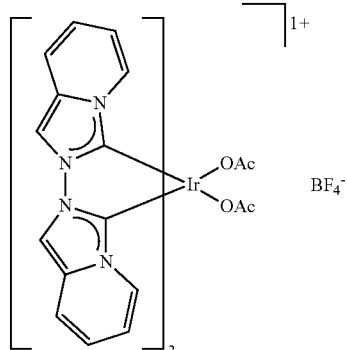 BF$_4^-$

67
-continued
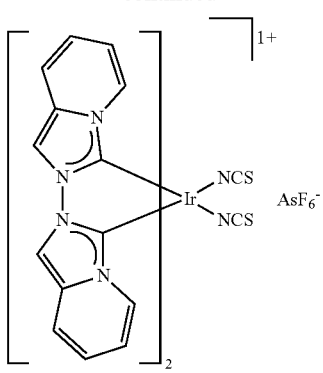 AsF₆⁻
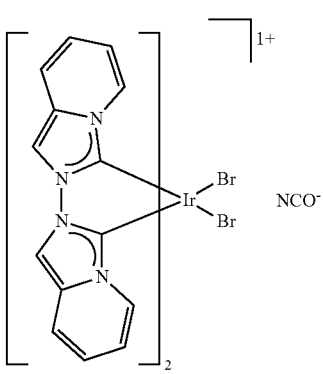 NCO⁻
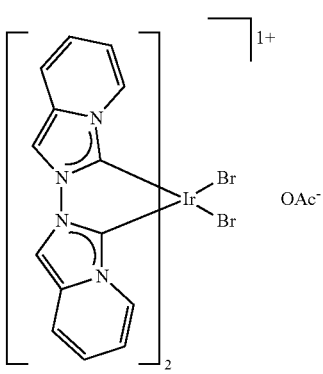 OAc⁻
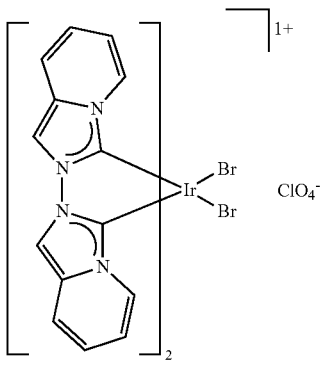 ClO₄⁻
68
-continued
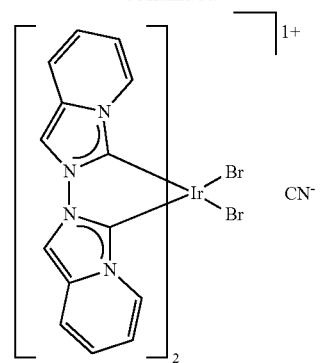 CN⁻
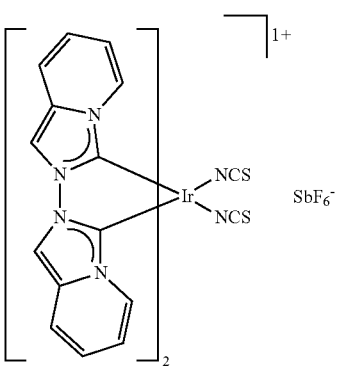 SbF₆⁻
[Chem. 43]
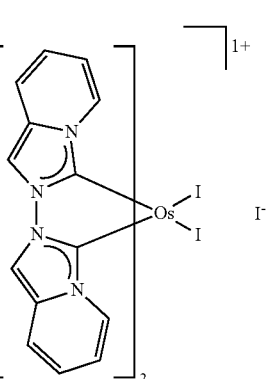 I⁻
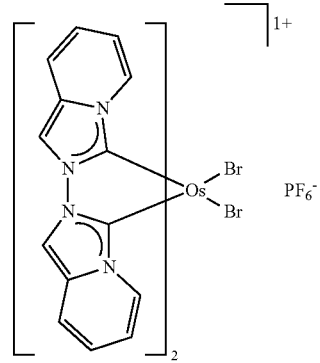 PF₆⁻

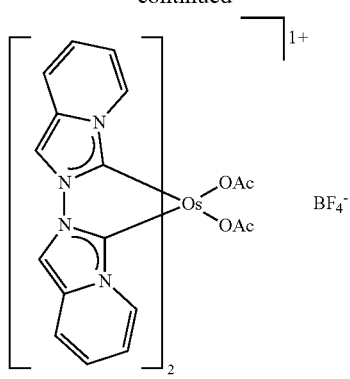
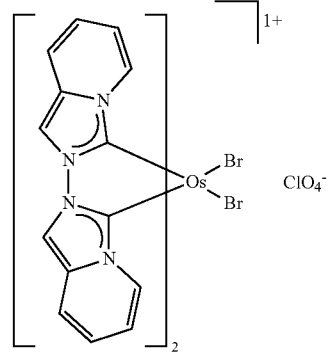
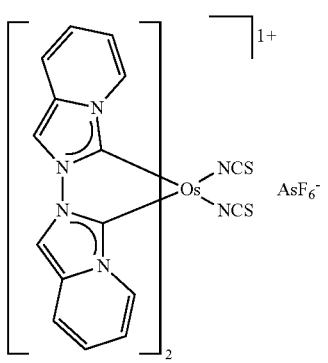
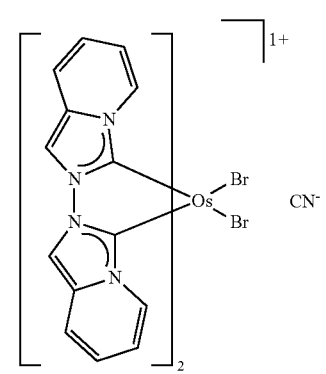
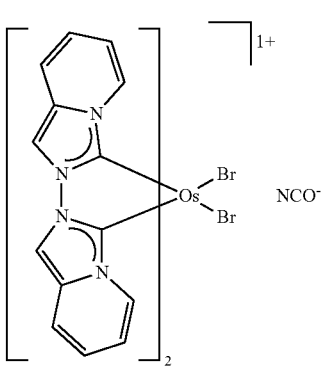
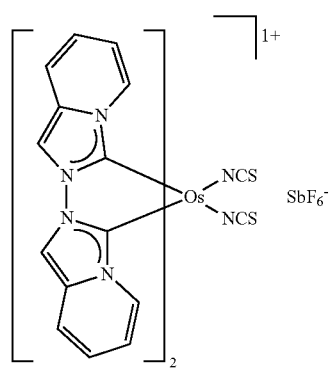
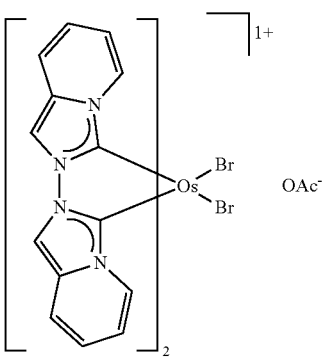
[Chem. 44]
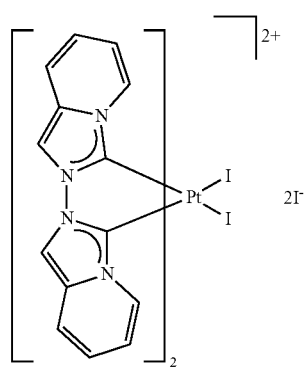

71
-continued
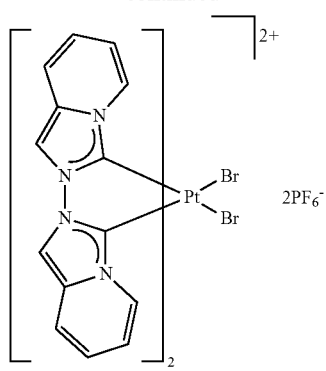 2PF6−
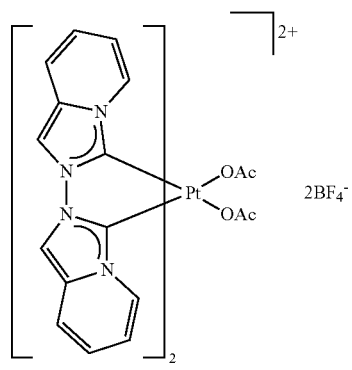 2BF4−
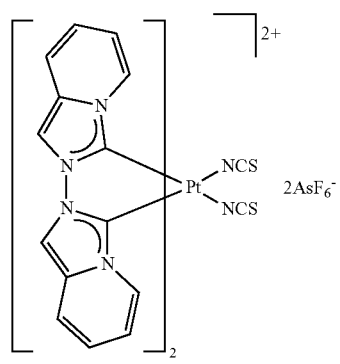 2AsF6−
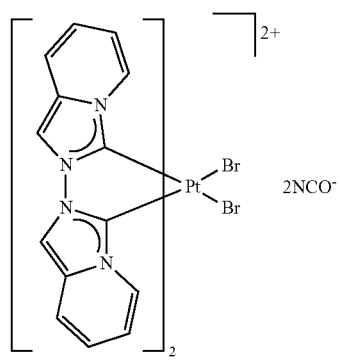 2NCO−
72
-continued
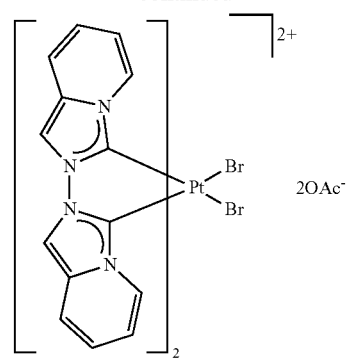 2OAc−
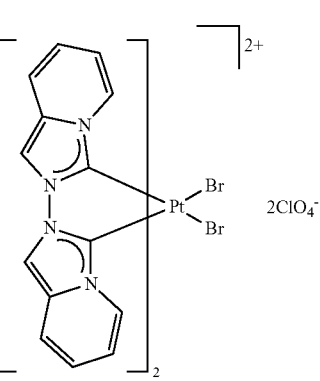 2ClO4−
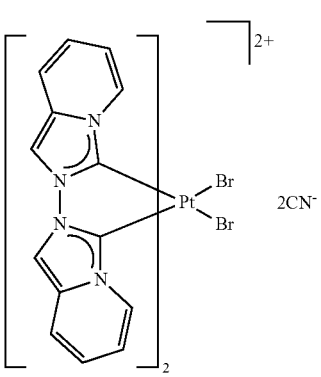 2CN−
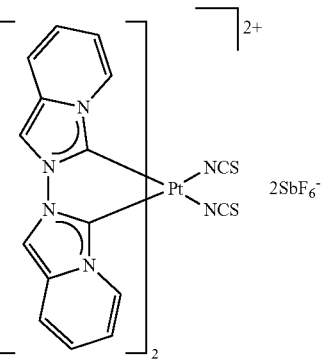 2SbF6−

73
-continued
74
-continued
[Chem. 45]
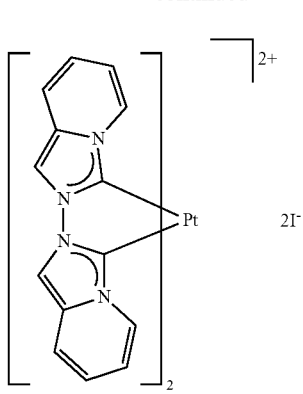 2I⁻
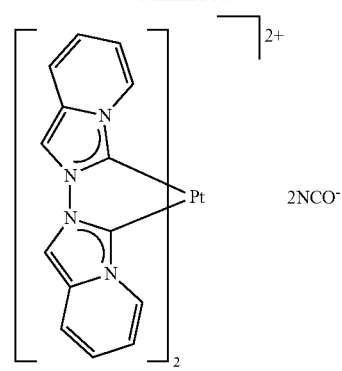 2NCO⁻
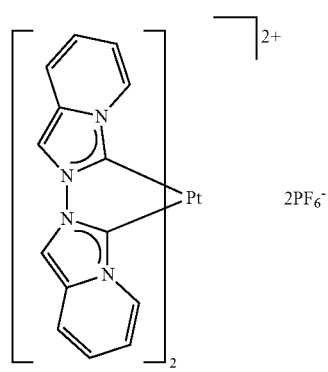 2PF₆⁻
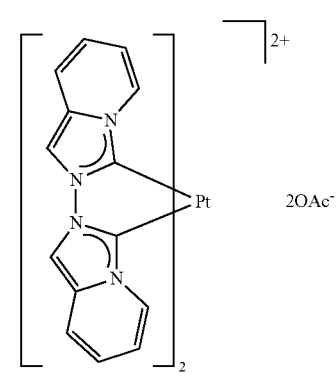 2OAc⁻
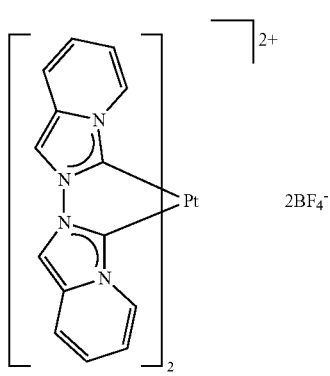 2BF₄⁻
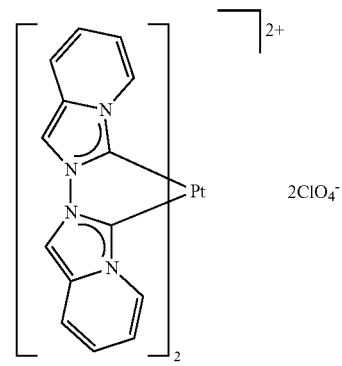 2ClO₄⁻
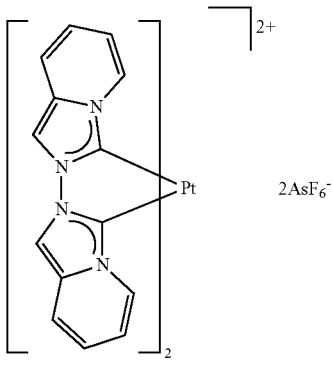 2AsF₆⁻
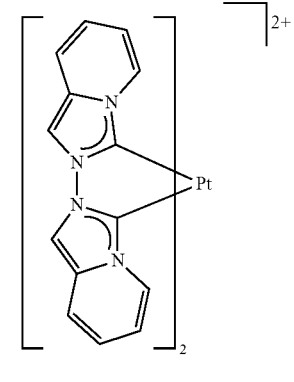 2CN⁻

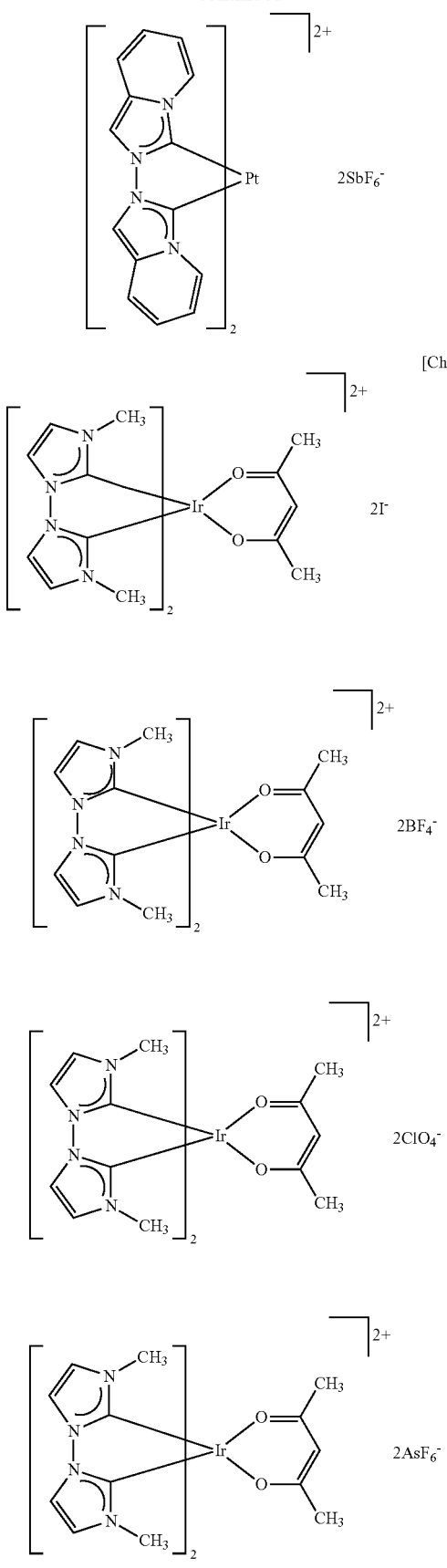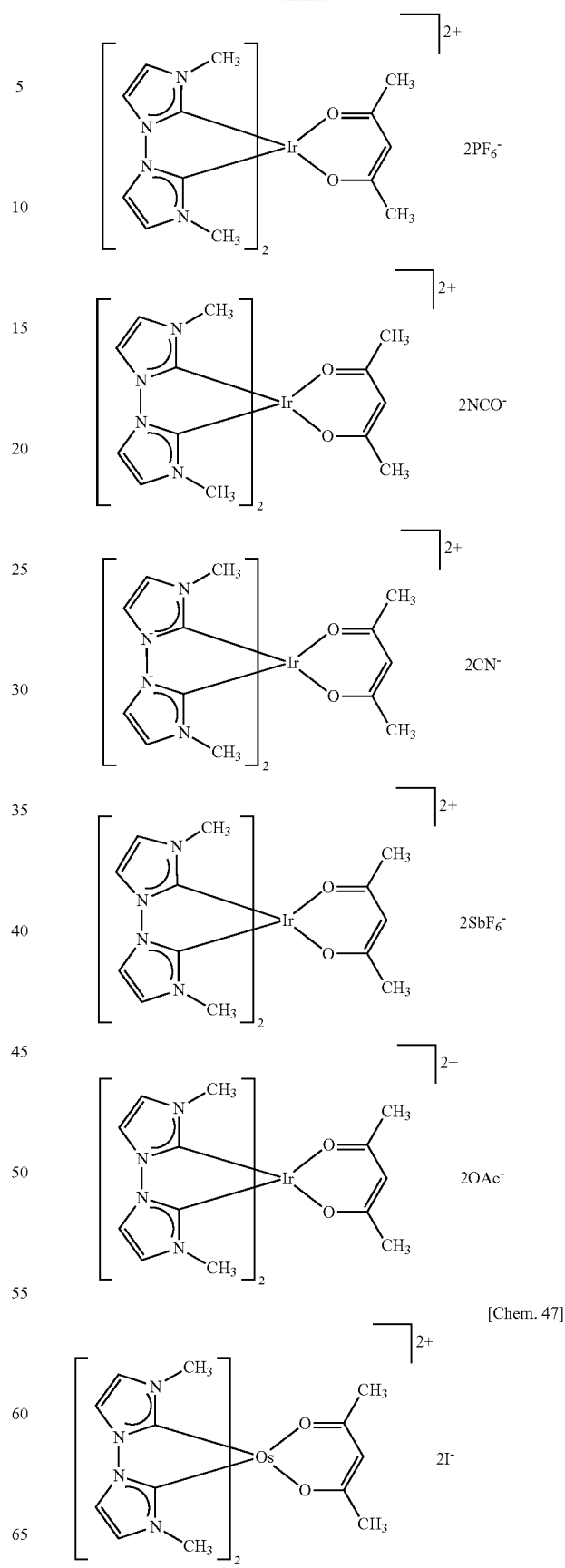

77
-continued
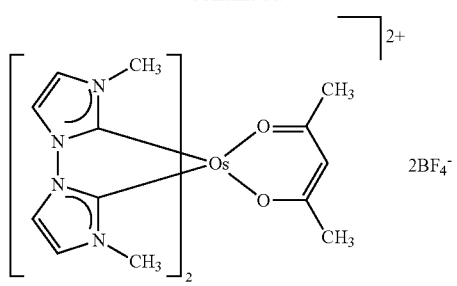
2BF$_4^-$
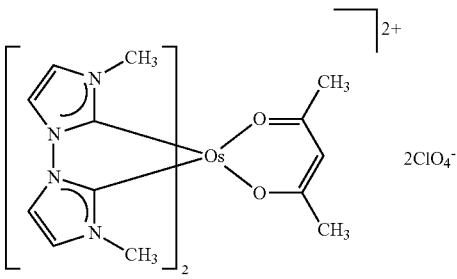
2ClO$_4^-$
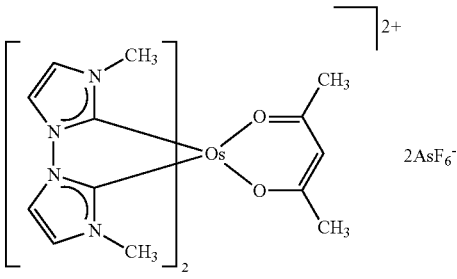
2AsF$_6^-$
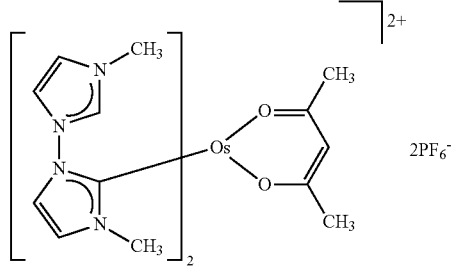
2PF$_6^-$
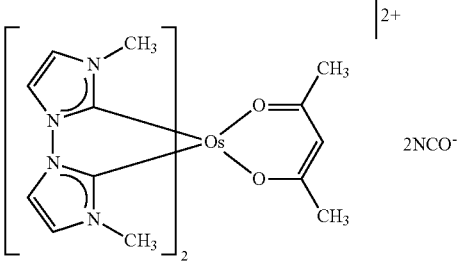
2NCO$^-$
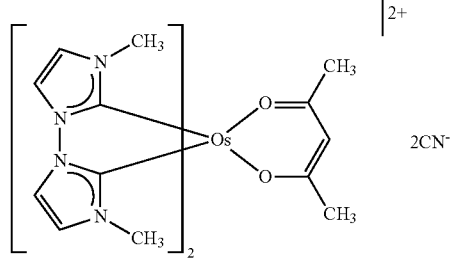
2CN$^-$
78
-continued
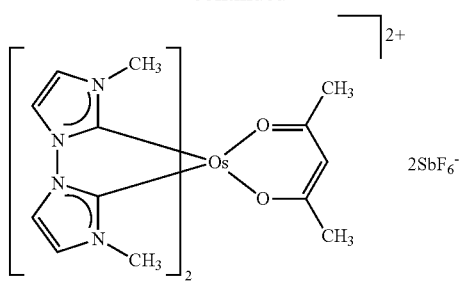
2SbF$_6^-$
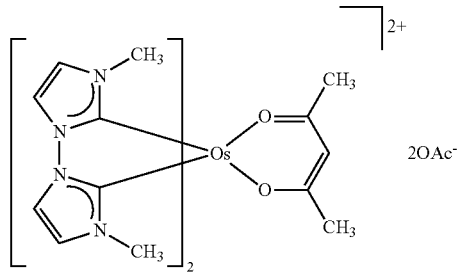
2OAc$^-$
[Chem. 48]
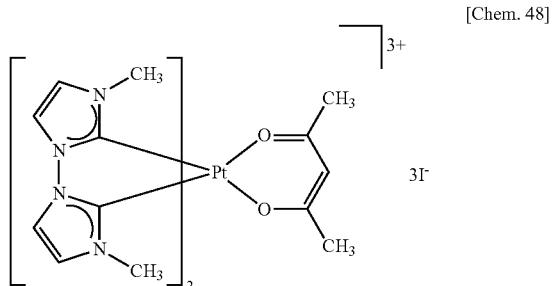
3I$^-$
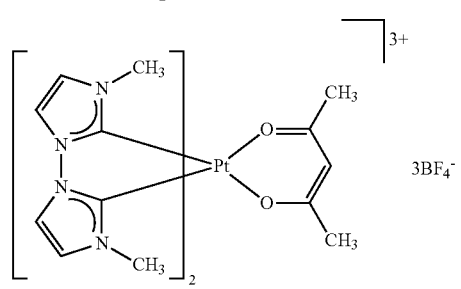
3BF$_4^-$
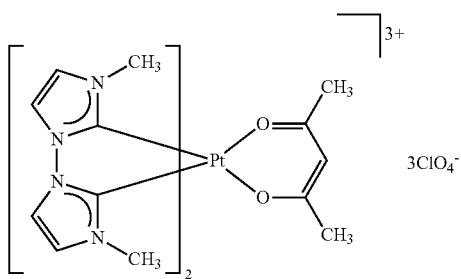
3ClO$_4^-$
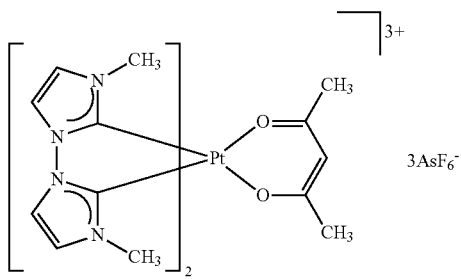
3AsF$_6^-$ -continued
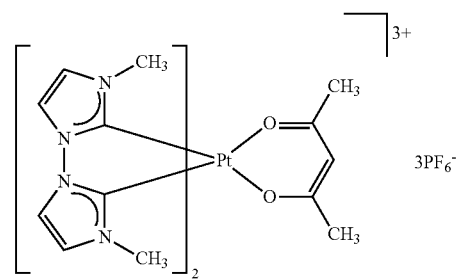 3PF6−
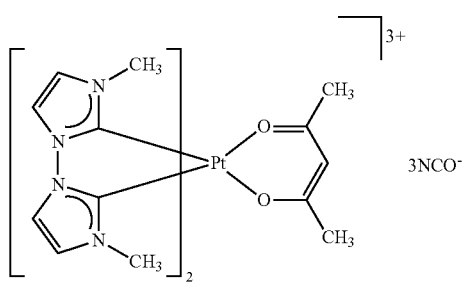 3NCO−
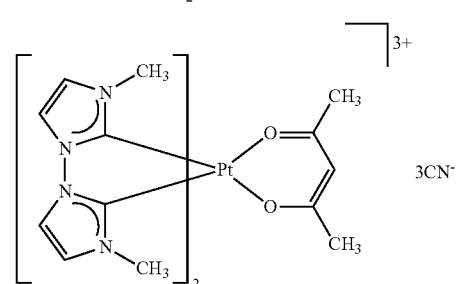 3CN−
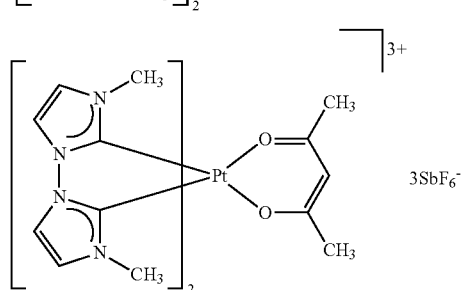 3SbF6−
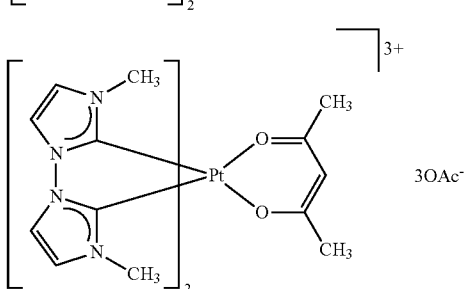 3OAc−
[Chem. 49]
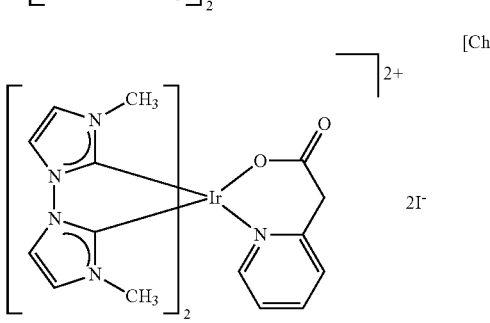 2I−
-continued
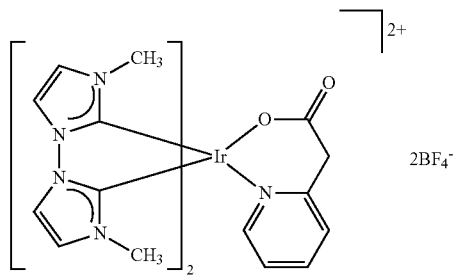 2BF4−
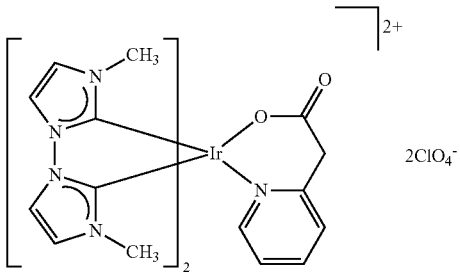 2ClO4−
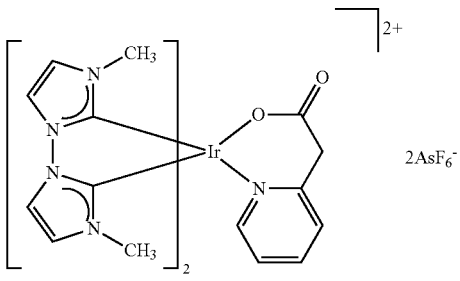 2AsF6−
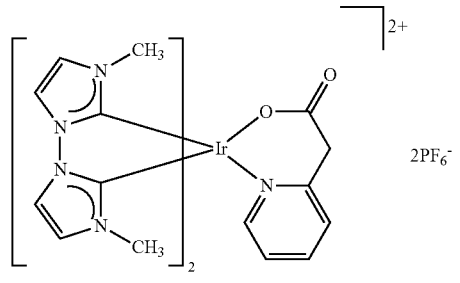 2PF6−
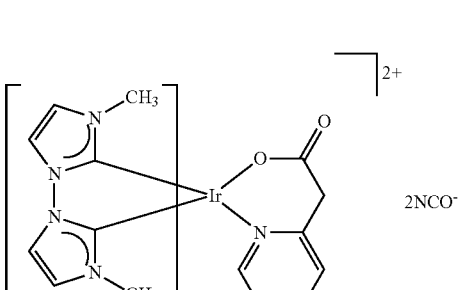 2NCO−
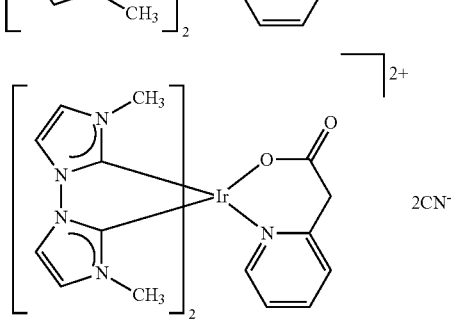 2CN−

81
-continued
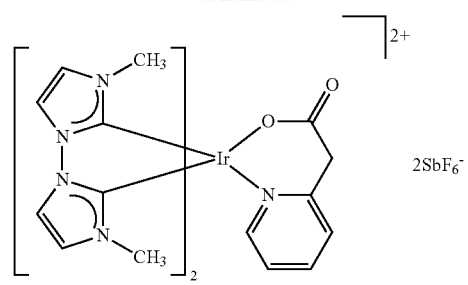 2SbF$_6^-$
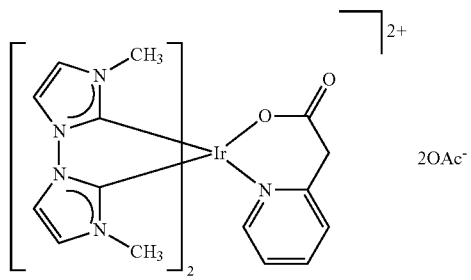 2OAc$^-$
[Chem. 50]
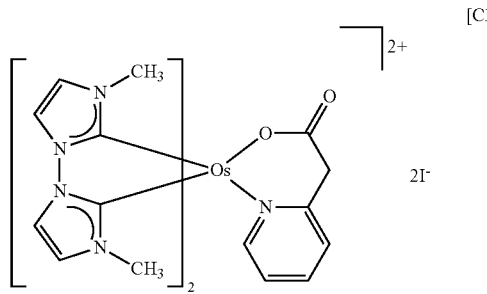 2I$^-$
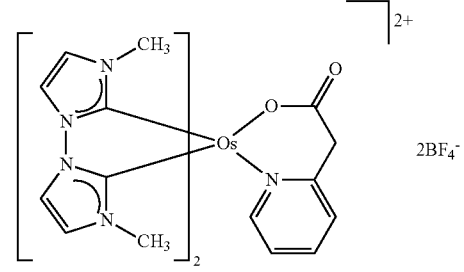 2BF$_4^-$
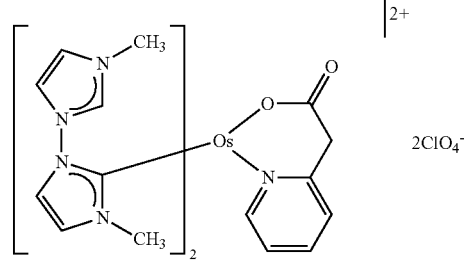 2ClO$_4^-$
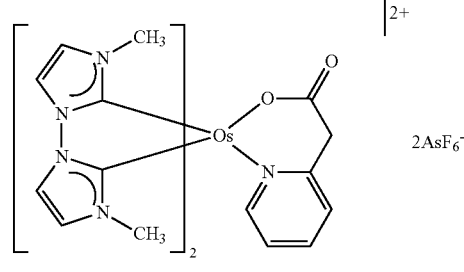 2AsF$_6^-$
82
-continued
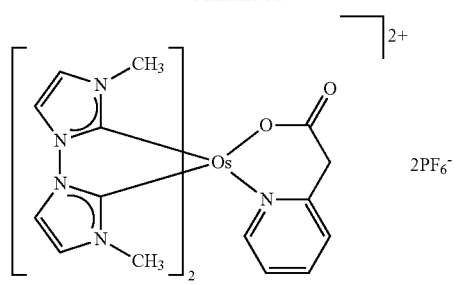 2PF$_6^-$
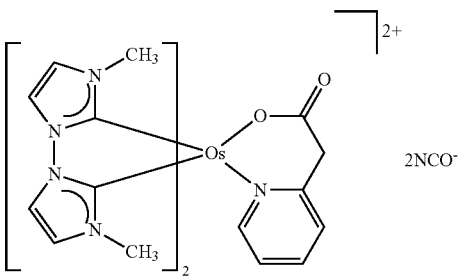 2NCO$^-$
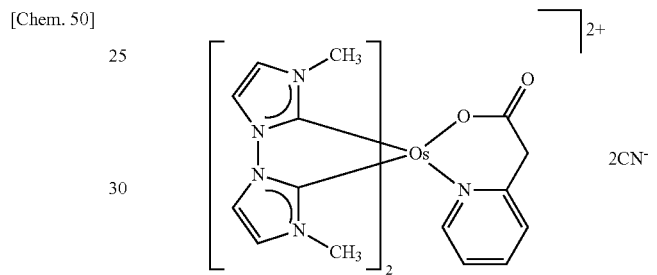 2CN$^-$
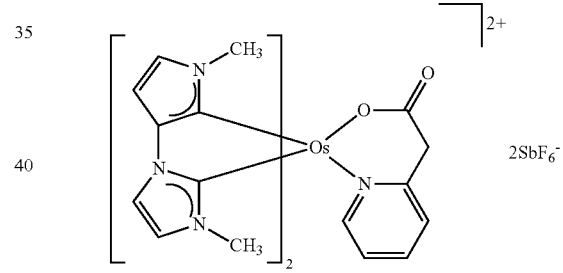 2SbF$_6^-$
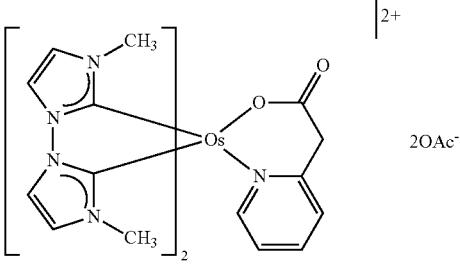 2OAc$^-$
[Chem. 51]
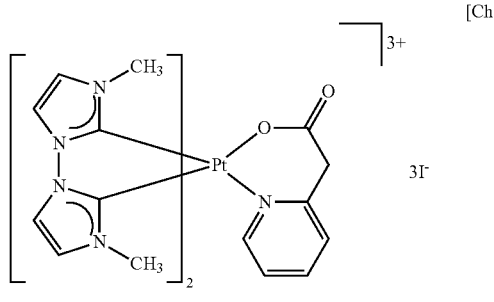 3I$^-$

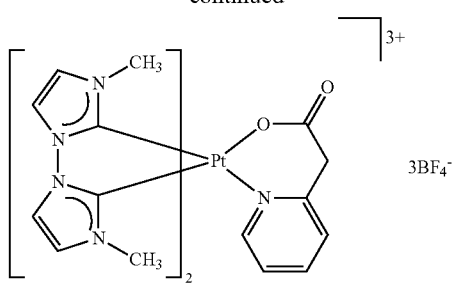
3BF$_4^-$
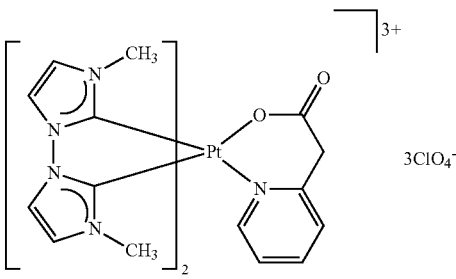
3ClO$_4^-$
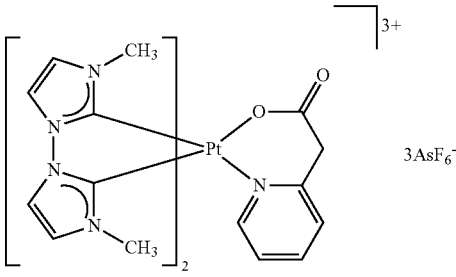
3AsF$_6^-$
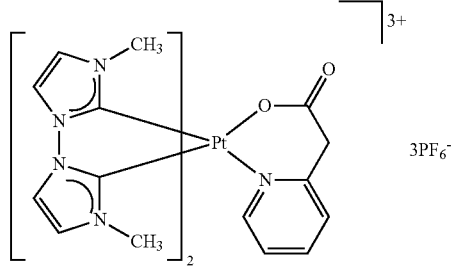
3PF$_6^-$
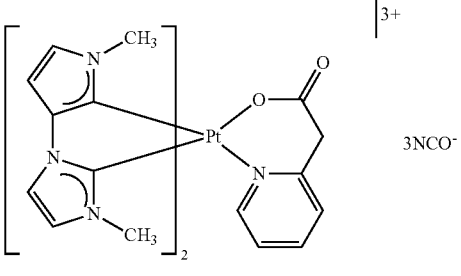
3NCO$^-$
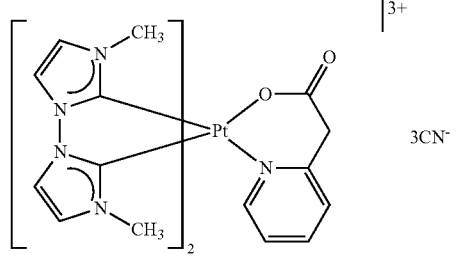
3CN$^-$
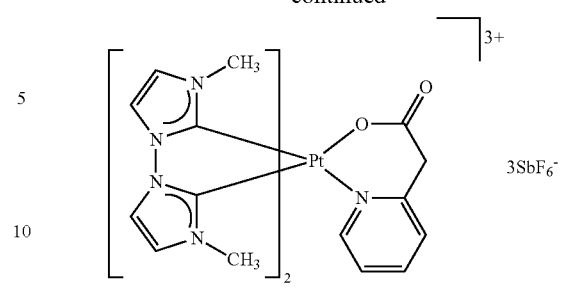
3SbF$_6^-$
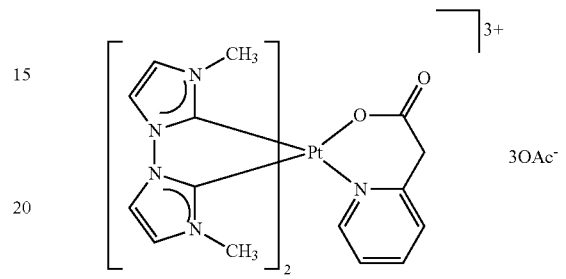
3OAc$^-$
[Chem. 52]
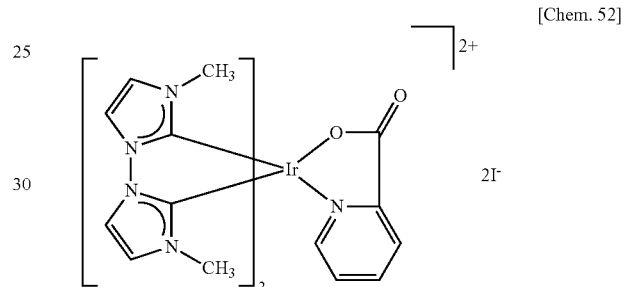
2I$^-$
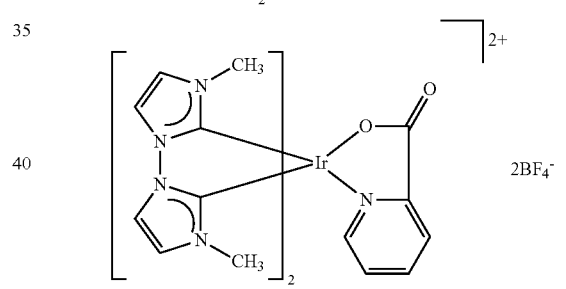
2BF$_4^-$
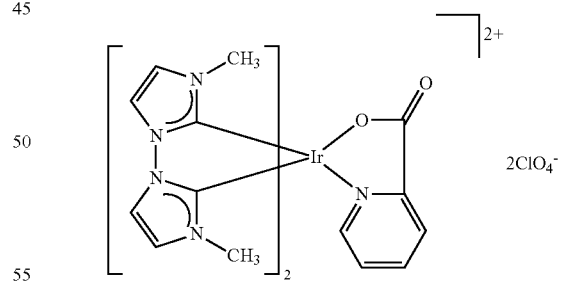
2ClO$_4^-$
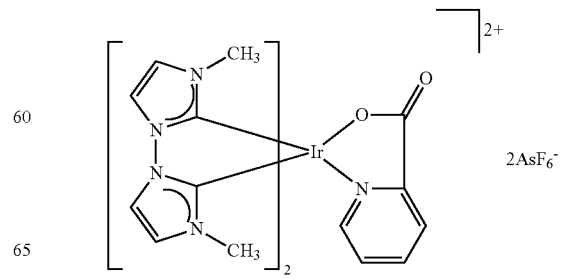
2AsF$_6^-$ 85
-continued
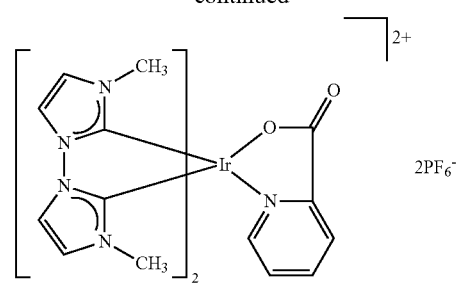
2PF$_6^-$
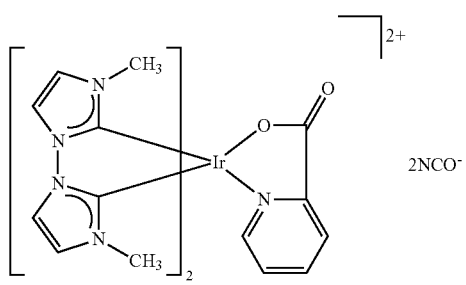
2NCO$^-$
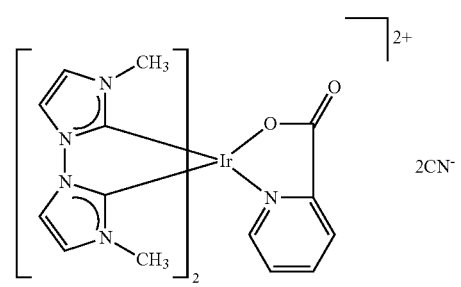
2CN$^-$
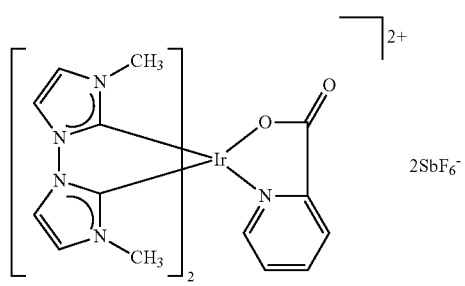
2SbF$_6^-$
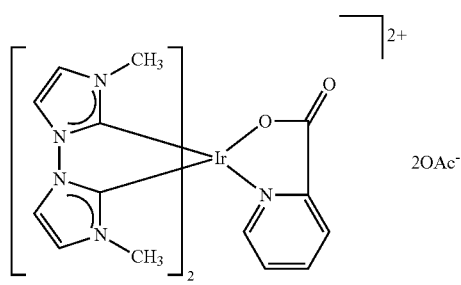
2OAc$^-$
[Chem. 53]
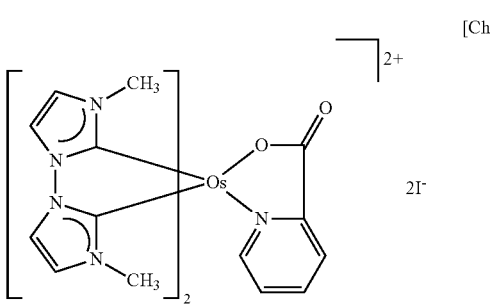
2I$^-$
86
-continued
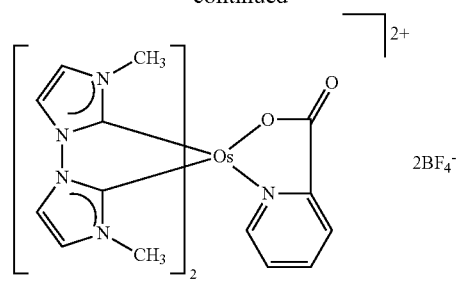
2BF$_4^-$
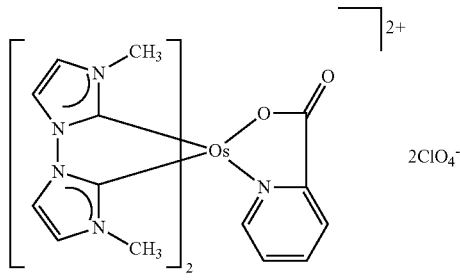
2ClO$_4^-$
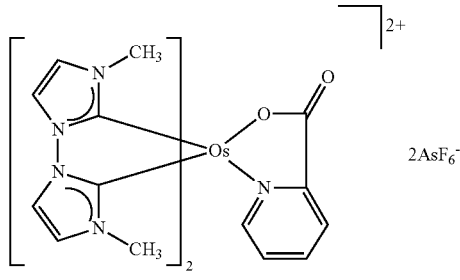
2AsF$_6^-$
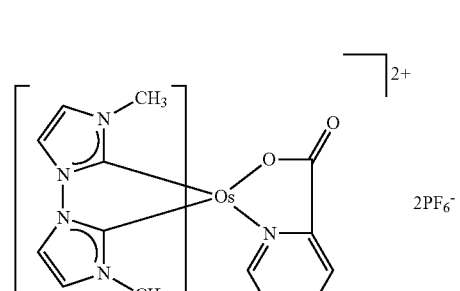
2PF$_6^-$
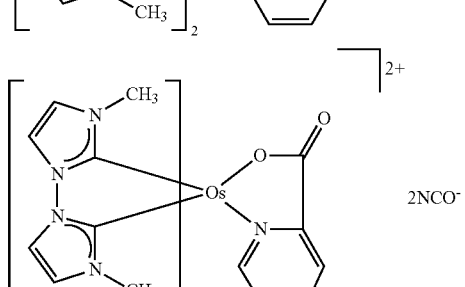
2NCO$^-$
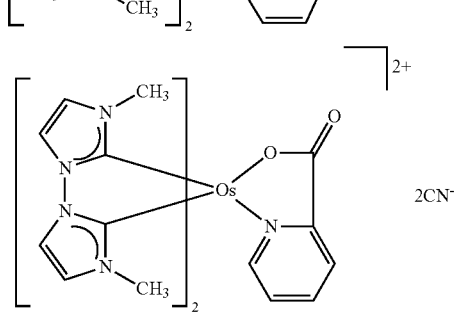
2CN$^-$ 87
-continued
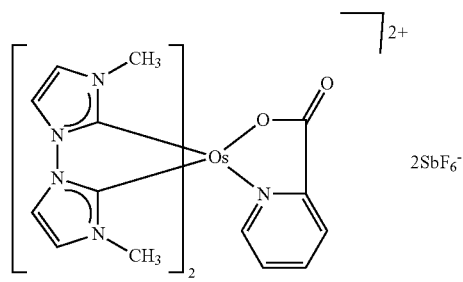
2SbF$_6^-$
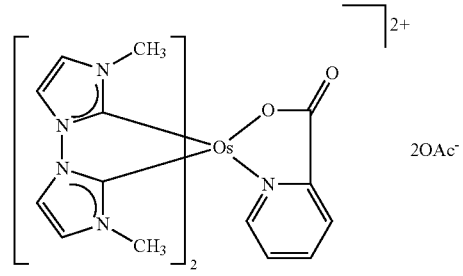
2OAc$^-$
[Chem. 54]
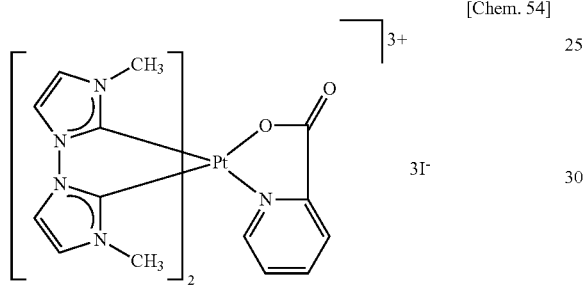
3I$^-$
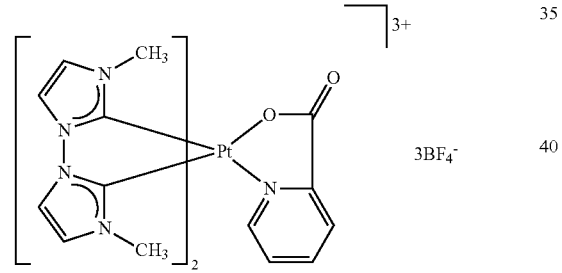
3BF$_4^-$
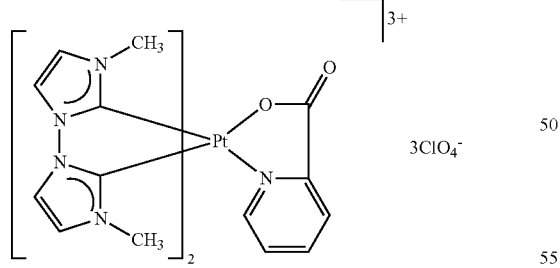
3ClO$_4^-$
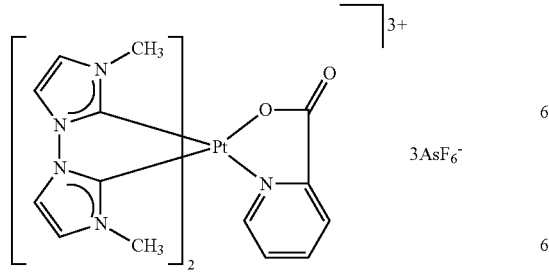
3AsF$_6^-$
88
-continued
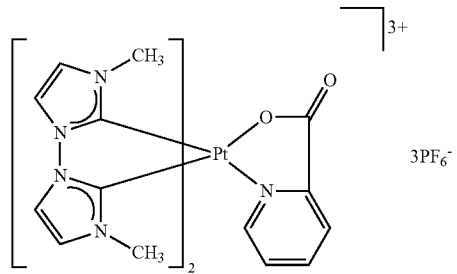
3PF$_6^-$
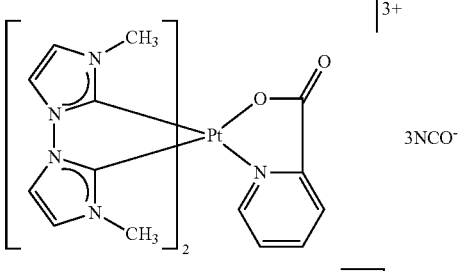
3NCO$^-$
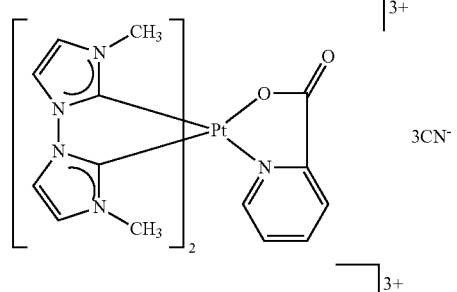
3CN$^-$
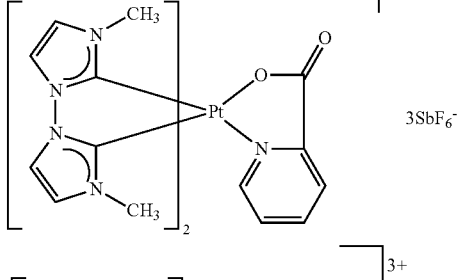
3SbF$_6^-$
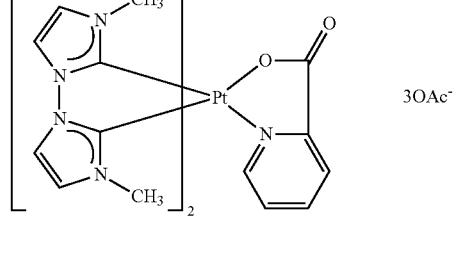
3OAc$^-$
[Chem. 55]
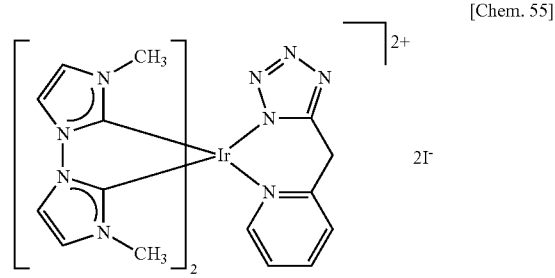
2I$^-$ 89
-continued
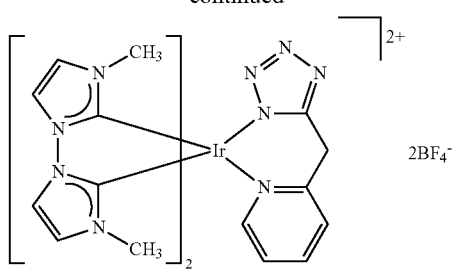  2BF4-
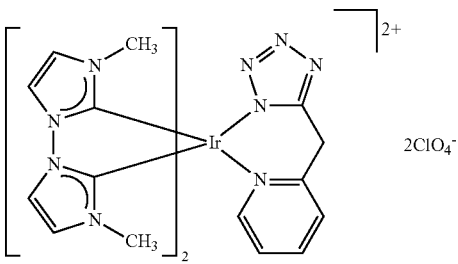  2ClO4-
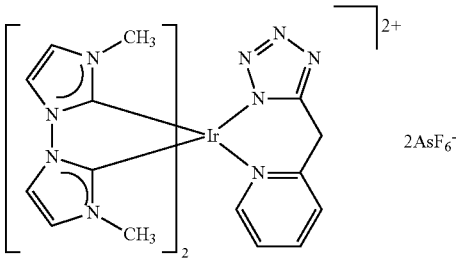  2AsF6-
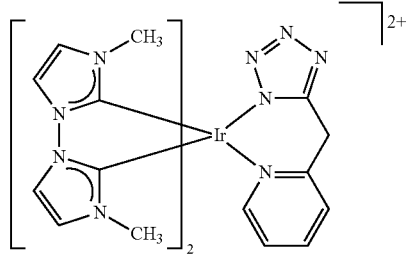  2PF6-
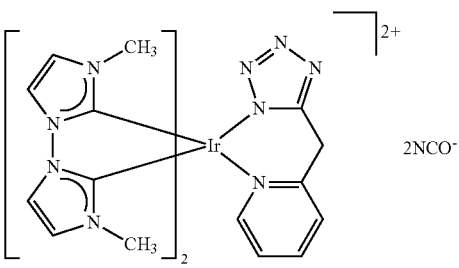  2NCO-
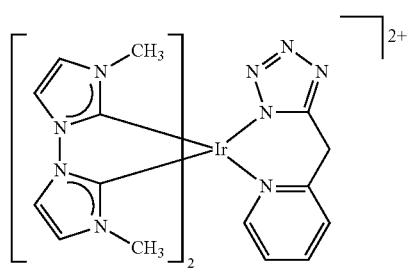  2CN-
90
-continued
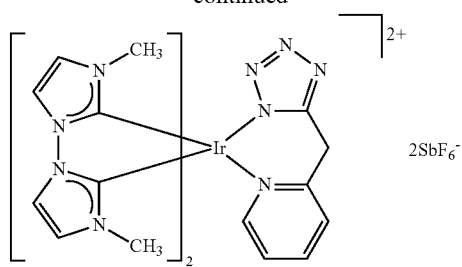  2SbF6-
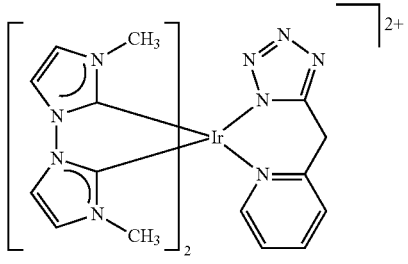  2OAc-
[Chem. 56]
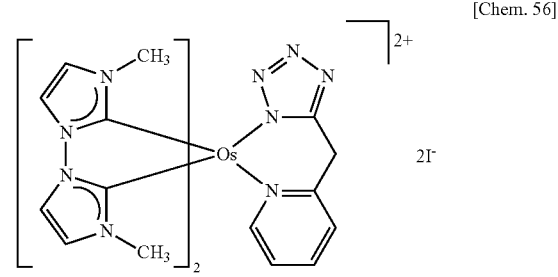  2I-
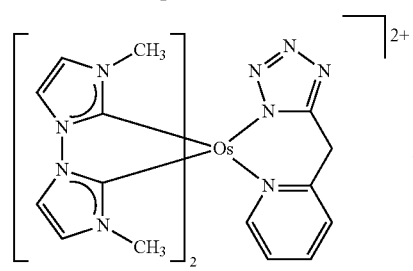  2BF4-
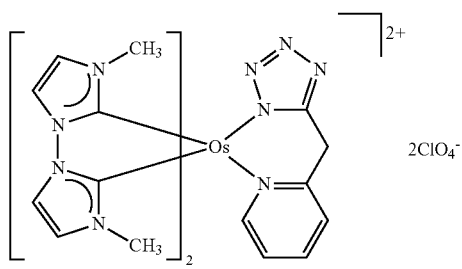  2ClO4-
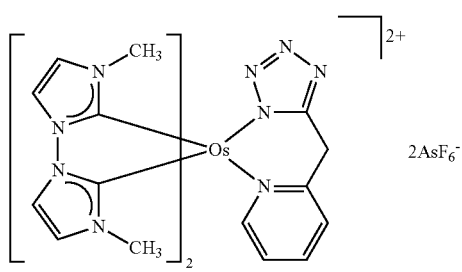  2AsF6-

91
-continued
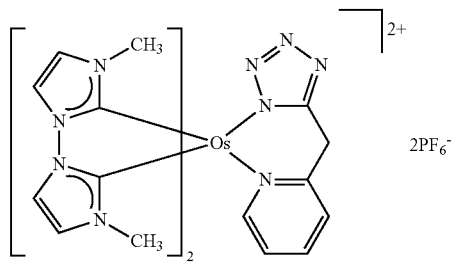 2PF$_6^-$
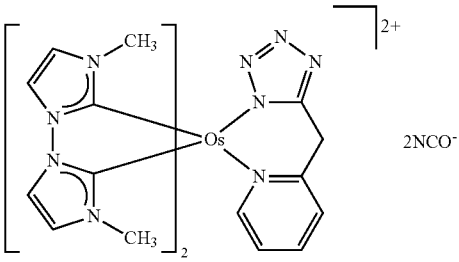 2NCO$^-$
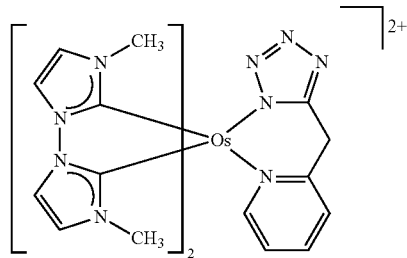 2CN$^-$
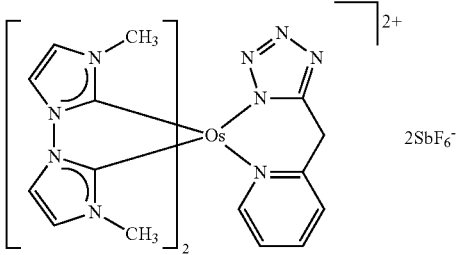 2SbF$_6^-$
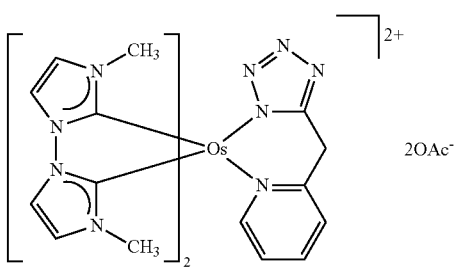 2OAc$^-$
[Chem. 57]
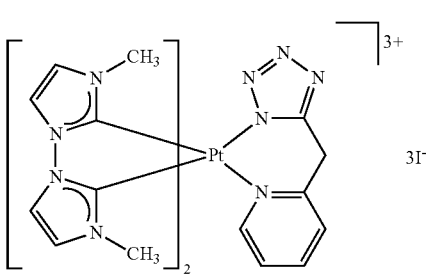 3I$^-$
92
-continued
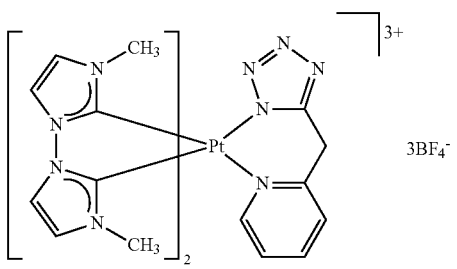 3BF$_4^-$
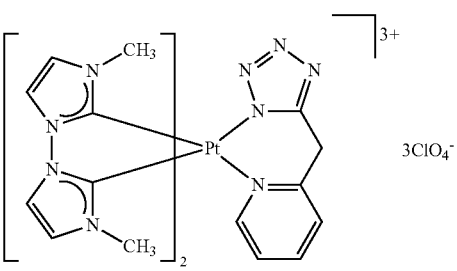 3ClO$_4^-$
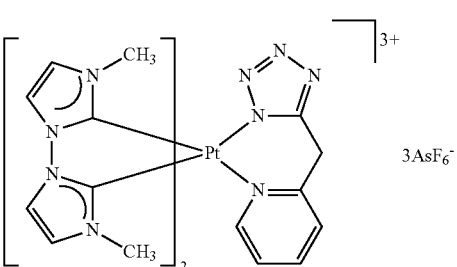 3AsF$_6^-$
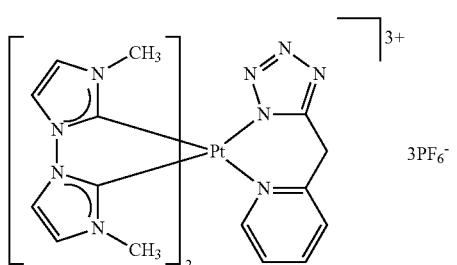 3PF$_6^-$
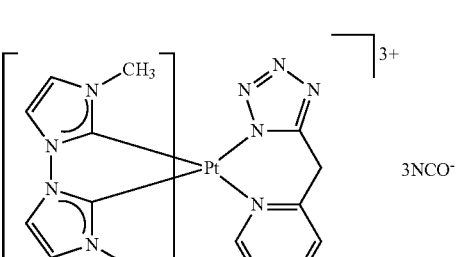 3NCO$^-$
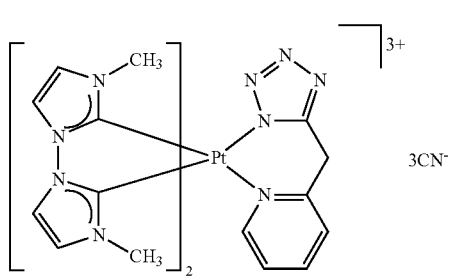 3CN$^-$ 93
-continued
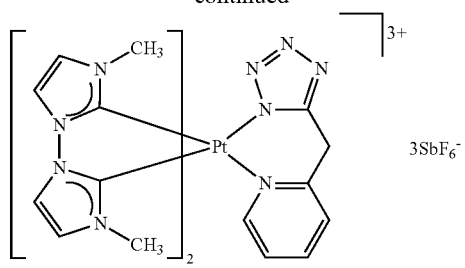
3SbF$_6^-$
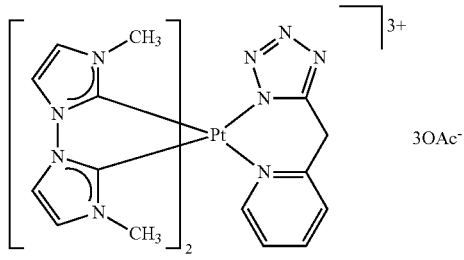
3OAc$^-$
[Chem. 58]
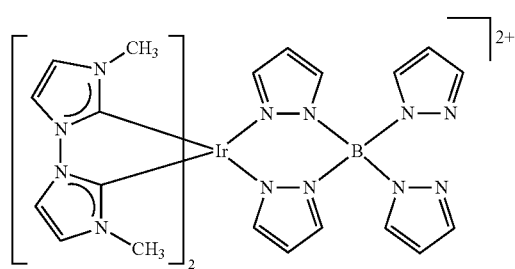
2Cl$^-$
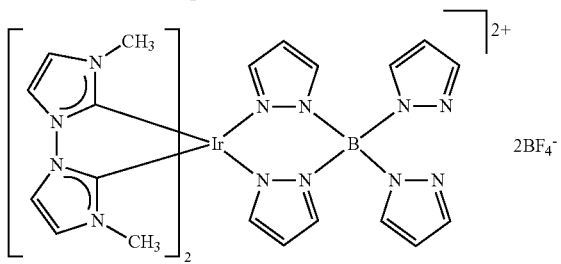
2BF$_4^-$
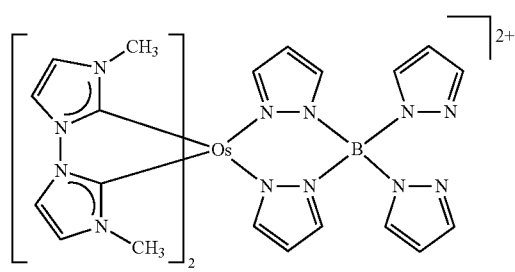
2ClO$_4^-$
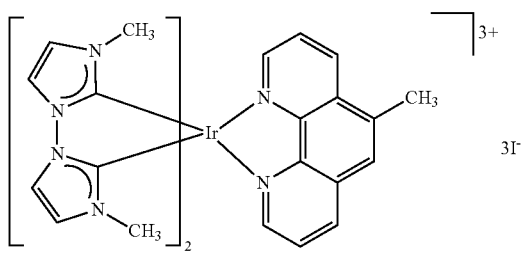
2Cl$^-$
94
-continued
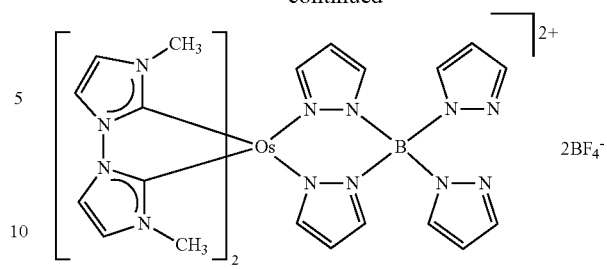
2BF$_4^-$
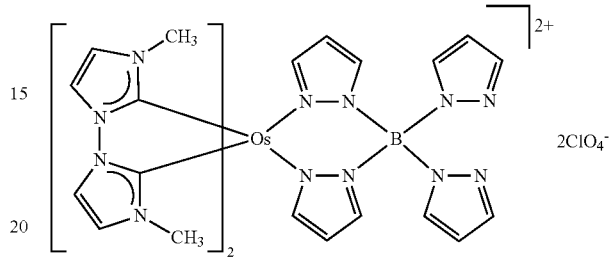
2ClO$_4^-$
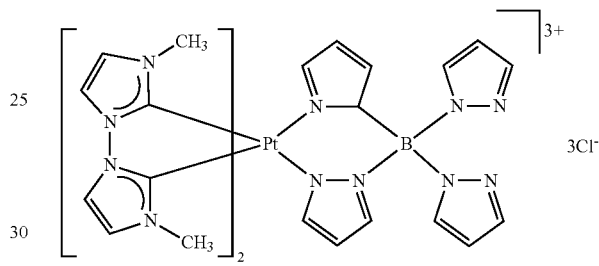
3Cl$^-$
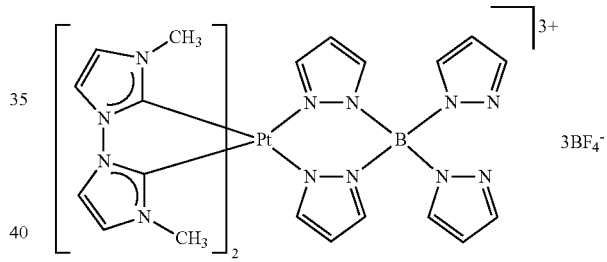
3BF$_4^-$
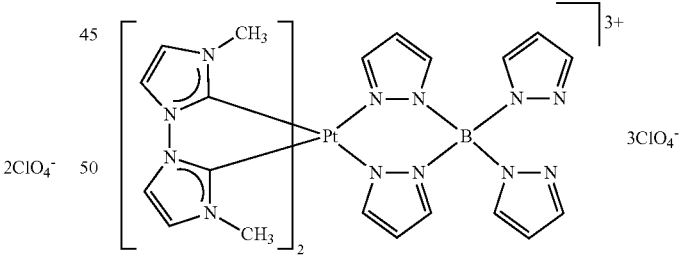
3ClO$_4^-$
[Chem. 59]
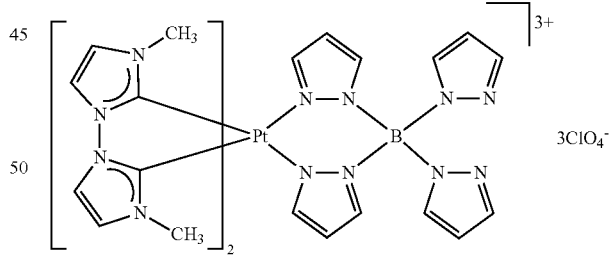
3I$^-$

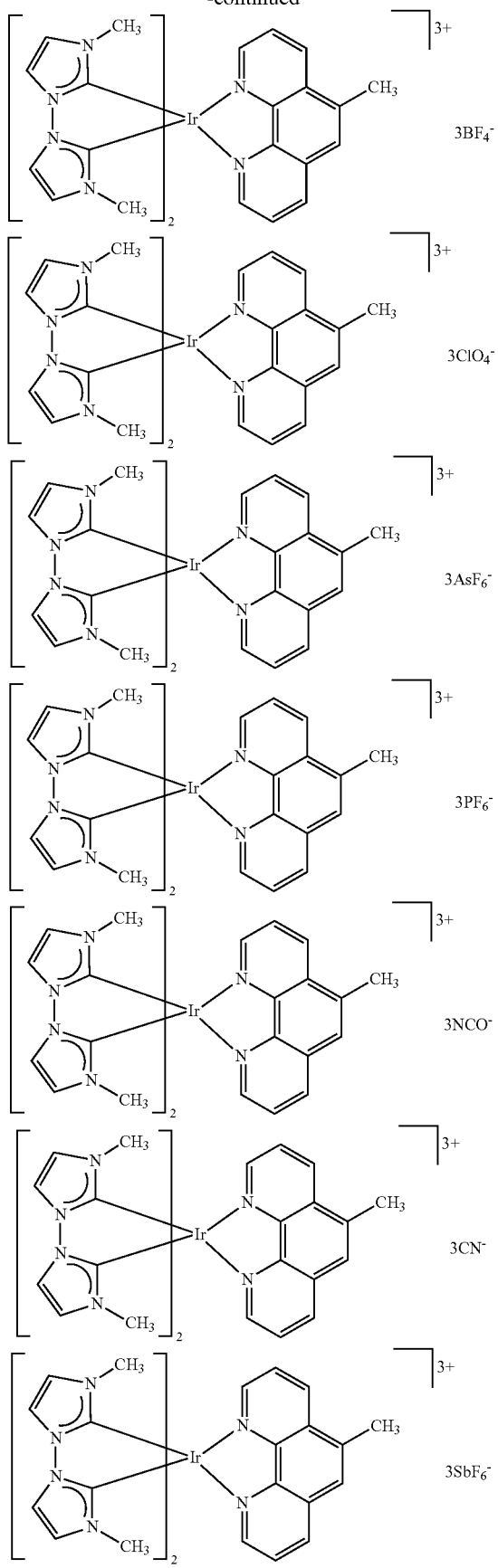
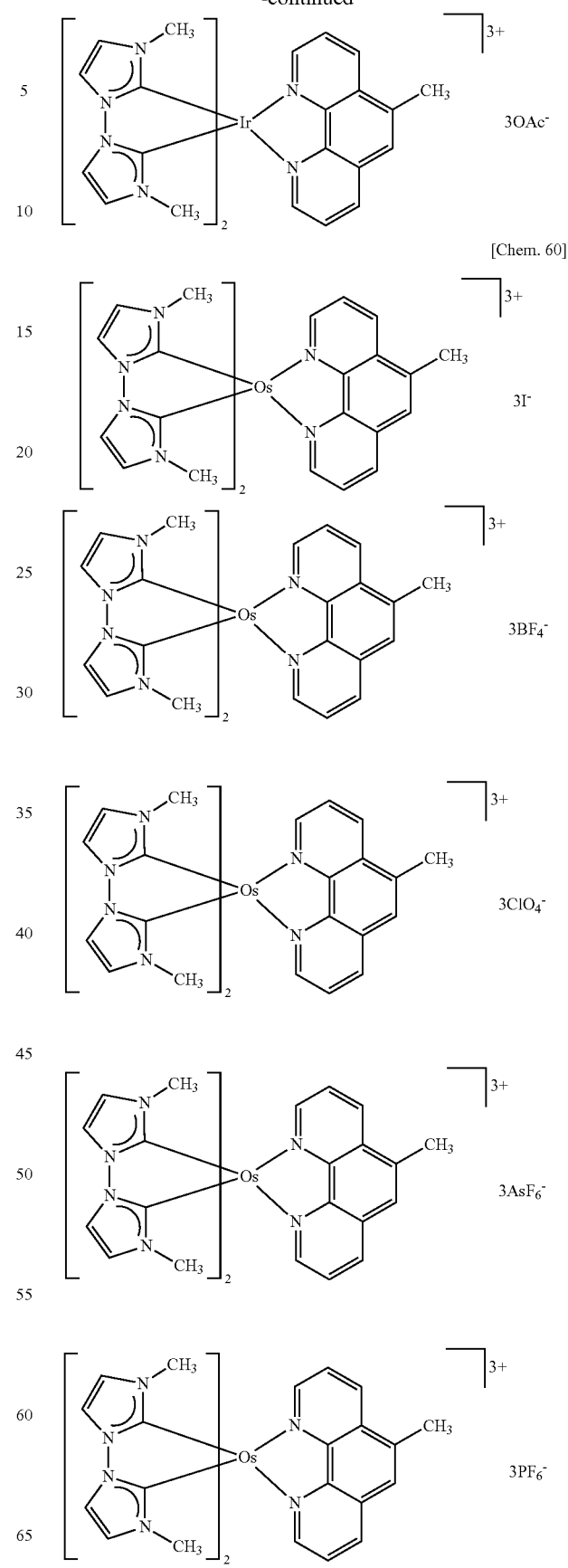

97
-continued
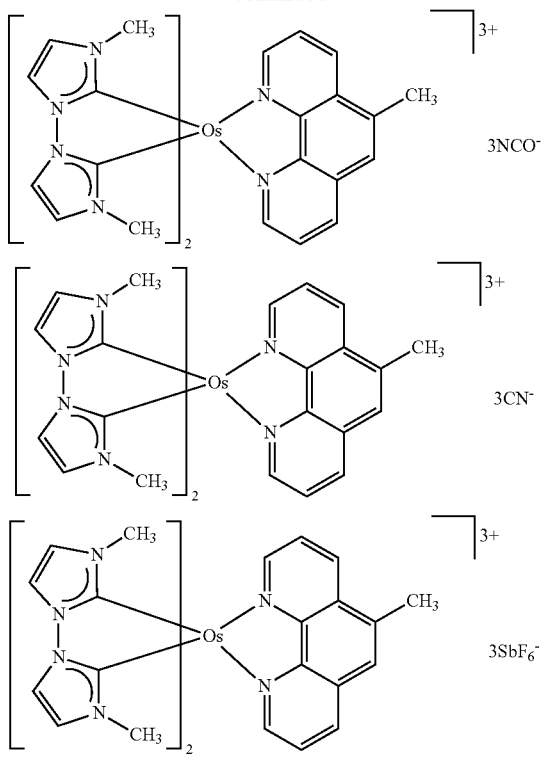
98
-continued
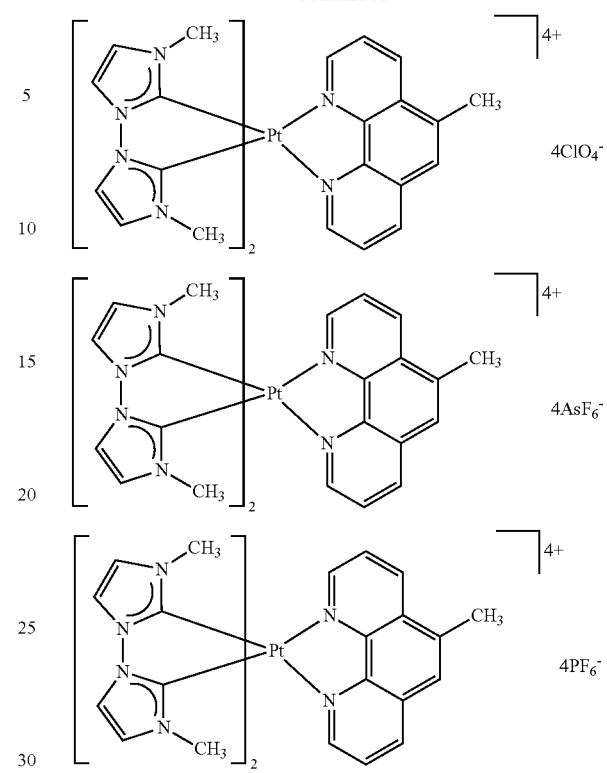
[Chem. 61]
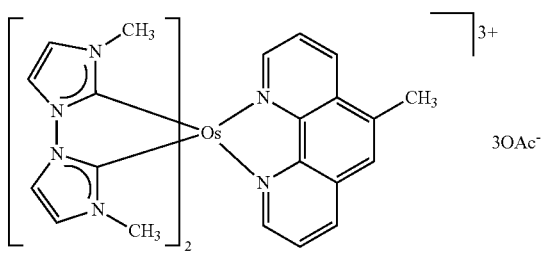
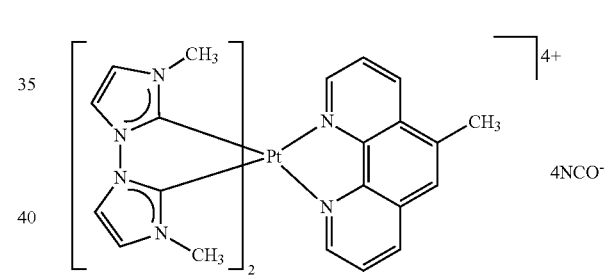
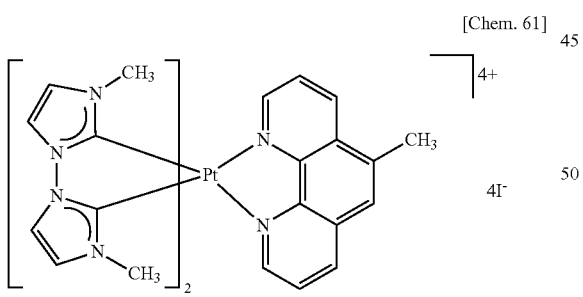
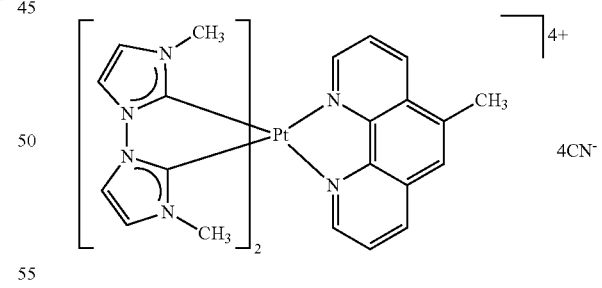
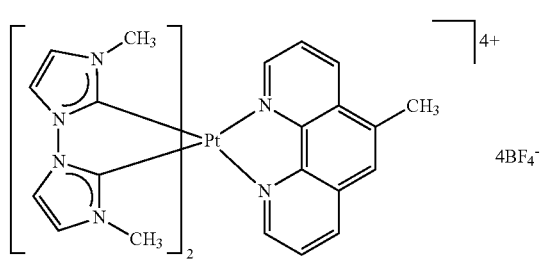
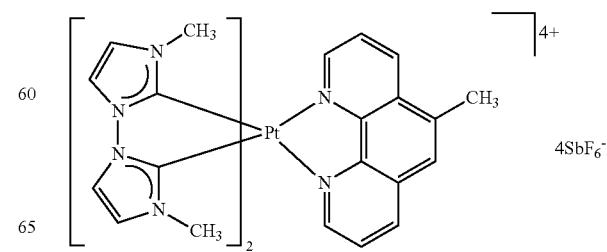

-continued

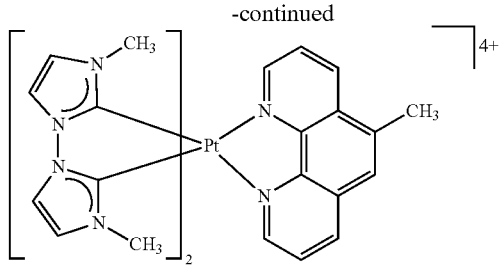

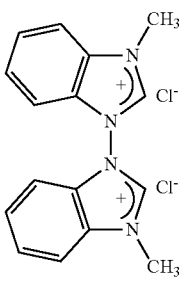

The transition metal complex according to the invention includes a ligand having two or more carbene sites, in which the carbene sites of the ligand are coordinated to a transition metal. Since such two or more carbene sites are directly coordinated to a transition metal, the transition metal complex according to the invention has a high T1 level. Accordingly, the transition metal complex according to the invention can realize pure blue emission to ultraviolet emission and can be used as a luminescent dopant (luminescent material) and as a host material having a high T1 level due to a pure blue luminescent dopant.

Next, a synthesis method of the transition metal complex according to the invention will be described. The transition metal complex having a structure according to any one of the formulae (1) to (7) can be synthesized using a combination of well-known methods of the related art. For example, a ligand can be synthesized while referring to Organometallics, 2008, 27, 2128-2136, Inorganic Chemistry Communications, 2008, 11, 1170-1173, Dalton Trans., 2008, 916; and the transition metal complex can be synthesized while referring to Organometallics, 2008, 27, 2128-2136, Dalton Trans., 2008, 916, Angew. Chem. Int. Ed., 2008, 47, 4542 and Japanese Unexamined Patent Application Publication (Translation of PCT Application) No. 2009-542026.

Hereinafter, an example of a synthesis method of a transition metal complex, which is the transition metal complex according to the embodiment, will be described.

An Ir complex (Compound (a-3)) which is the transition metal complex according to the embodiment can be synthesized according to the following synthesis route. In a synthesis scheme of the following example, Me represents a methyl group, acac represents acetyl acetate, THF represents tetrahydrofuran, and DMSO represents dimethylsulfoxide.

[Chem. 62]

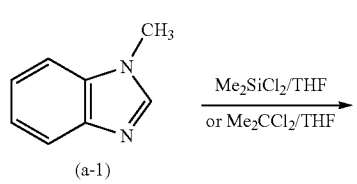

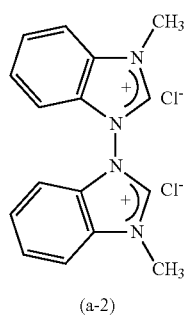

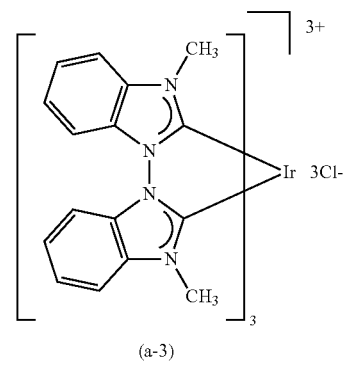

A compound which is a ligand can be synthesized while referring to Inorganic Chemistry Communications, 2008, 11, 1170-1173. First, 1-methyl-1H-benzoimidazol (Compound 1 (a-1)) is dissolved in THF (tetrahydrofuran) to obtain a solution. Dimethyldichlorosilane ($Me_2SiCl_2$) was added to the obtained solution, followed by stirring and reaction at room temperature for 1 hour. An unreacted raw material is removed from the reaction solution using hexane. As a result, Compound (a-2) can be synthesized. In this case, instead of $Me_2SiCl_2$, $Me_2CCl_2$ (wherein Me represents a methyl group) may be used.

Next, Compound (a-3) which is the transition metal complex according to the embodiment can be synthesized while referring to, for example, Japanese Unexamined Patent Application Publication (Translation of PCT Application) No. 2009-542026.

Iridium acetyl acetate ($Ir(acac)_3$) is put into dimethylsulfoxide (DMSO), followed by heating at 100° C. The DMSO solution of Compound (a-2) is added dropwise to the resultant solution, followed by stirring and reaction for 2 hours. Next, the solvent was removed under reduced pressure, the extracted solid material is washed with tetrahydrofuran (THF) twice, followed by drying under reduced pressure. As a result, Compound (a-3) can be synthesized.

In addition, when the transition metal complex according to the embodiment has two or more different kinds of ligands, the transition metal complex can be synthesized while referring to, for example, Angew. Chem. Int. Ed., 2008, 47, 4542-4545. For example, when an Ir complex [Ir(La)$_2$(Lb)] having two bidentate ligands La and one bidentate ligand Lb is synthesized, 1 equivalent of [IrCl(COD)]$_2$ (COD=1.5-cyclooctadiene) and 4 equivalents of the ligands La are heated to reflux in an alcohol solution in the presence of methoxysodium according to a method described in, for example, Dalton Trans., 2008, 916, Angew. Chem. Int. Ed., 2008, 47, 4542, thereby synthesizing a chlorine-bridged dinuclear Ir complex [Ir(μ-Cl)(La)$_2$]$_2$. Then, this chlorine-bridged dinuclear Ir complex is caused to react with the ligand Lb. As a result, an Ir complex

[Ir(La)$_2$(Lb)] can be synthesized. When either the ligand La or the ligand Lb is a carbene ligand, or when both the ligand La and the ligand Lb are a carbene ligand, this synthesis method can be applied.

The synthesized transition metal complex which is a luminescent material can be identified using MS spectrum (FAB-MS), $^1$H-NMR spectrum, LC-MS spectrum, or the like.

Hereinafter, embodiments of an organic light-emitting element, a color-converting light-emitting element, an organic laser diode element, a dye laser, a display device, an illumination device, and electronic equipment according to embodiments of the invention will be described referring to the drawings. In the respective drawings of FIGS. 1 to 16, the reduction scales of the respective members are different from each other so as to make the sizes of the respective members recognizable in the drawings.

<Organic Light-Emitting Element>

An organic light-emitting element (organic EL element) according to an embodiment of the invention includes at least one organic layer that includes a light-emitting layer; and a pair of electrodes between which the organic layer is interposed.

FIG. 1 is a diagram schematically illustrating a first embodiment of the organic light-emitting element according to the embodiment. An organic light-emitting element 10 illustrated in FIG. 1 has a configuration in which a first electrode 12, an organic EL layer (organic layer) 17, and a second electrode 16 are laminated in this order on a substrate (not illustrated). In an example of FIG. 1, the organic EL layer 17 that is interposed between the first electrode 12 and the second electrode 16 has a configuration in which a hole transport layer 13, an organic light-emitting layer 14, and an electron transport layer 15 are laminated in this order.

The first electrode 12 and the second electrode 16 function as an anode or a cathode of the organic light-emitting element 10 as a pair. That is, when the first electrode 12 is an anode, the second electrode 16 is a cathode; and when the first electrode 12 is a cathode, the second electrode 16 is an anode. In FIG. 1 and the following description, a case in which the first electrode 12 is an anode and the second electrode 16 is a cathode will be described as an example. When the first electrode 12 is a cathode and the second electrode 16 is an anode, as described below, the organic EL layer (organic layer) 17 may have a lamination structure in which a hole injection layer and a hole transport layer are disposed on the second electrode 16 side; and an electron injection layer and an electron transport layer are disposed on the first electrode 12 side.

The organic EL layer (organic layer) 17 may have a single-layer structure including the organic light-emitting layer 14; and may have a multilayer structure such as the lamination structure illustrated in FIG. 1 including the hole transport layer 13, the organic light-emitting layer 14, and the electron transport layer 15. Specific configuration examples of the organic EL layer (organic layer) 17 are as follows. However, the embodiment is not limited thereto. In the following configurations, a hole injection layer and the hole transport layer 13 are disposed on the first electrode 12 side which is an anode; and an electron injection layer and the electron transport layer 15 are disposed on the second electrode 16 side which is a cathode.

(1) Organic light-emitting layer 14
(2) Hole transport layer 13/Organic light-emitting layer 14
(3) Organic light-emitting layer 14/Electron transport layer 15
(4) Hole injection layer/Organic light-emitting layer 14
(5) Hole transport layer 13/Organic light-emitting layer 14/Electron transport layer 15
(6) Hole injection layer/Hole transport layer 13/Organic light-emitting layer 14/Electron transport layer 15
(7) Hole injection layer/Hole transport layer 13/Organic light-emitting layer 14/Electron transport layer 15/Electron injection layer
(8) Hole injection layer/Hole transport layer 13/Organic light-emitting layer 14/Hole blocking layer/Electron transport layer 15
(9) Hole injection layer/Hole transport layer 13/Organic light-emitting layer 14/Hole blocking layer/Electron transport layer 15/Electron injection layer
(10) Hole injection layer/Hole transport layer 13/Electron blocking layer/Organic light-emitting layer 14/Hole blocking layer/Electron transport layer 15/Electron injection layer Here, each layer of the organic light-emitting layer 14, the hole injection layer, the hole transport layer 13, the hole blocking layer, the electron blocking layer, the electron transport layer 15, and the electron injection layer may have a single-layer structure or a multilayer structure.

When the organic EL layer 17 includes an exciton blocking layer, the exciton blocking layer can be inserted between the hole transport layer 13 and the organic light-emitting layer 14 and/or between the organic light-emitting layer 14 and the electron transport layer 15. The exciton blocking layer has a function of preventing excitons, produced in the organic light-emitting layer 14, from being deactivated by energy transfer to the hole transport layer 13 and the electron transport layer 15. As a result, the energy of the excitons can be more effectively used for emission and high-efficient emission can be realized. The exciton blocking layer may be formed of a well-known exciton blocking material. However, it is preferable that the transition metal complex according to the embodiment be used as the exciton blocking material.

The organic light-emitting layer 14 may be formed of only the above-described transition metal complex according to the embodiment; may be formed of a combination of the transition metal complex according to the embodiment, which is used as a dopant (luminescent material), and a host material; or may be formed of a combination of the transition metal complex according to the embodiment, which is used as a host material, and a luminescent dopant. In addition, the organic light-emitting layer 14 according to the embodiment optionally further contain a hole transport material, an electron transport material, and an additive (for example, a donor or an acceptor); and may have a configuration in which the above-described materials are dispersed in a polymer material (binder resin) or in an inorganic material. The organic light-emitting layer 14 recombines holes injected from the first electrode 12 with electrons injected from the second electrode 16 and discharges (emits) light using phosphorescent emission of the transition metal complex (luminescent material) according to the embodiment contained in the organic light-emitting layer 14 or using phosphorescent emission of a luminescent dopant.

When the organic light-emitting layer 14 is formed of a combination of the transition metal complex according to the embodiment, which is used as a luminescent dopant (luminescent material), and a host material, a well-known host material for organic EL of the related art can be used as the host material. Examples of such a host material include carbazole derivatives such as 4,4'-bis(carbazole)biphenyl, 9,9-di(4-dicarbazole-benzyl)fluorene (CPF), 3,6-bis(triphenylsilyl)carbazole (mCP), poly(N-octyl-2,7-carbazole-O-9, 9-dioctyl-2,7-fluorene) (PCF), 1,3,5-tris(carbazol-9-yl)benzene (TCP), and 9,9-bis[4-(carbazol-9-yl)phenyl]fluorene (FL-2-CBP); aniline derivatives such as 4-(diphenylphosphoryl)-N,N-diphenylaniline (HM-A1); fluorene derivatives such as 1,3-bis(9-phenyl-9H-fluoren-9-yl)benzene (mD-PFB), and 1,4-bis(9-phenyl-9H-fluoren-9-yl)benzene (pD-PFB); 1,3,5-tris[4-(diphenylamino)phenyl]benzene (TDAPB); 1,4-bis(triphenylsilyl)benzene (UGH-2); 1,3-bis(triphenylsilyl)benzene (UGH-3); and 9-(4-tert-butylphenyl)-3,6-bis(triphenylsilyl)-9H-carbazole (CzSi).

When the organic light-emitting layer 14 is formed of a combination of the transition metal complex according to the embodiment, which is used as a host material, and a luminescent dopant of the related art, a well-known luminescent dopant for organic EL of the related art can be used as the luminescent dopant. Examples of such a luminescent dopant material include phosphorescent luminescent organic metal complexes including Ir complexes such as tris(2-phenylpyridine)iridium (III) (Ir(ppy)$_3$), bis(2-phenylpyridine)(acetylacetonate)iridium (III) (Ir(ppY)$_2$(acac)), tris[2-(p-tolyl)pyridine]iridium (III) (Ir(mppy)$_3$), iridium (III) bis[(4,6-difluorophenyl)-pyridinato-N,C2']picolinate (FIrPic), iridium (III) bis(4',6'-difluorophenylpyridinato)tetrakis(1-pyrazolyl)borate (FIr6), iridium (III) tris(1-phenyl-3-methylbenzimidazolin-2-ylidene-C,C2') (Ir(Pmb)$_3$), Bis(2,4-difluorophenylpyridinato) (5-(pyridin-2-yl)-1H-tetrazolate) iridium (III) (FIrN4), bis(2-benzo[b]thiophen-2-yl-pyridine) (acetylacetonate)iridium (III) (Ir(btp)$_2$(acac)), tris(1-phenylisoquinoline)iridium (III) (Ir(piq)$_3$), tris(1-phenylisoquinoline)(acetylacetonato)iridium(III) (Ir(pig)$_2$(acac)), bis[1-(9,9-dimethyl-9H-fluoren-2-yl)-isoquinoline](acetylacetonate)iridium (III) (Ir(filq)$_2$(acac)), bis[2-(9,9-dimethyl-9H-fluoren-2-yl)-isoquinoline](acetylacetonate) iridium (III) (Ir(flq)$_2$(acac)), tris(2-phenylquinoline)iridium (III) (Ir(2-phq)$_3$), and tris(2-phenylquinoline)(acetylacetonate)iridium (III) (Ir(2-phq)$_2$(acac)); Os complexes such as osmium bis(3-trifluoromethyl-5-(2-pyridyl)-pyrazolate) dimethylphenylphosphine (Os(fppz)$_2$(PPhMe$_2$)$_2$), osmium bis(3-(trifluoromethyl)-5-(4-tert-butylpyridyl)-1,2,4-triazolate)(diphenylmethylphosphine) (Os(bpftz)$_2$(PPh$_2$Me)$_2$); and Pt complexes such as 5,10,15,20-tetraphenyltetrabenzoporphyrin platinum.

The hole injection layer and the hole transport layer 13 are provided between the first electrode 12 and the organic light-emitting layer 14 in order to efficiently perform the injection of holes from the first electrode 12, which is the anode, and the transport (injection) of holes to the organic light-emitting layer 14. The electron injection layer and the electron transport layer 15 are provided between the second electrode 16 and the organic light-emitting layer 14 in order to efficiently perform the injection of electrons from the second electrode 16, which is the cathode, and the transport (injection) of electrons to the organic light-emitting layer 14.

Each of the hole injection layer, the hole transport layer 13, the electron injection layer, and the electron transport layer 15 can be formed of a well-known material of the related art, may be formed of only the following exemplary materials, may further include an additive (for example, a donor or an acceptor), and may have a configuration in which the above-described materials are dispersed in a polymer material (binder resin) or in an inorganic material.

Examples of a material forming the hole transport layer 13 include low-molecular-weight materials including oxides such as vanadium oxide (V$_2$O$_5$) and molybdenum oxide (MoO$_2$), inorganic p-type semiconductor materials, porphyrin compounds, aromatic tertiary amine compounds such as N,N'-bis(3-methylphenyl)-N,N'-bis(phenyl)-benzidine (TPD) and N,N'-di(naphthalene-1-yl)-N,N'-diphenyl-benzidine (NPD), hydrazone compounds, quinacridone compounds, and styrylamine compounds; and polymer materials including polyaniline (PANI), polyaniline-camphorsulfonic acid (PANI-CSA), 3,4-polyethylenedioxithiophene/polystyrenesulfonate (PEDOT/PSS), poly(triphenylamine) derivetives (Poly-TPD), polyvinyl carbazole (PVCz), poly(p-phenylenevinylene) (PPV), and poly(p-naphthalenevinylene) (PNV).

In order to efficiently perform the injection and transport of holes from the first electrode 12 which is an anode, as a material forming the hole injection layer, it is preferable that a material having a smaller energy level of highest occupied molecular orbital (HOMO) than that of a material forming the hole transport layer 13 be used. As the material forming the hole transport layer 13, it is preferable that a material having a higher hole mobility than that of the material forming the hole injection layer be used.

Examples of the material forming the hole injection layer include phthalocyanine derivatives such as copper phthalocyanine; amine compounds such as 4,4',4"-tris(3-methylphenylphenylamino)triphenylamine, 4,4',4"-tris(1-naphthylphenyl'amino)triphenylamine, 4,4',4"-tris(2-naphthylphenylamino)triphenylamine, 4,4',4"-tris[biphenyl-2-yl(phenyl)amino]triphenylamine, 4,4',4"-tris[biphenyl-3-yl(phenyl)amino]triphenylamine, 4,4',4"-tris[biphenyl-4-yl (3-methylphenyl)amino]triphenylamine, and 4,4',4"-tris[9,9-dimethyl-2-fluorenyl(phenyl)amino]triphenylamine; and oxides such as vanadium oxide (V$_2$O$_5$) and molybdenum oxide (MoO$_2$). However, the material forming the hole injection layer is not limited thereto.

In addition, in order to improve hole injecting and transporting properties, it is preferable that the hole injection layer and the hole transport layer 13 be doped with an acceptor. As the adapter, materials which are well-known in the related art as an acceptor material for organic EL can be used.

Examples of the acceptor material include inorganic materials such as Au, Pt, W, Ir, POCl$_3$, AsF$_6$, Cl, Br, I, vanadium oxide (V$_2$O$_5$), and molybdenum oxide (MoO$_2$); compounds having a cyano group such as TCNQ (7,7,8,8-tetracyanoquinodimethan), TCNQF4 (tetrafluorotetracyanoquinodimethane), TCNE (tetracyanoethylene), HCNB (hexacyanobutadiene), and DDQ (dicyclodicyanobenzoquinone); compounds having a nitro group such as TNF (trinitrofluorenone) and DNF (dinitrofluorenone); and organic materials such as fluorenyl, chloranil, and bromanil. Among these, compounds having a cyano group such as TCNQ, TCNQF4, TCNE, HCNB, and DDQ are more preferable from the viewpoint of being able to efficiently increasing the carrier density.

As a material forming the electron blocking layer, the above-described examples of the material forming the hole transport layer 13 and the hole injection layer can be used.

Examples of a material forming the electron transport layer 15 include low-molecular-weight materials such as inorganic materials which are n-type semiconductors, oxadiazole derivatives, triazole derivatives, thiopyrazine dioxide derivatives, benzoquinone derivatives, naphthoquinone derivatives, anthraquinone derivatives, diphenoquinone derivatives, fluorenone derivatives, and benzodifuran derivatives; and polymer materials such as poly(oxadiazole) (Poly-OXZ) and polystyrene derivatives (PSS).

Examples of a material forming the electron injection layer include, particularly, fluorides such as lithium fluoride (LiF) and barium fluoride (BaF$_2$); and oxides such as lithium oxide (Li$_2$O).

From the viewpoints of efficiently performing the injection and transport of electrons from the second electrode 16 which is the cathode, as the material forming the electron injection layer, it is preferable that a material having a higher energy level of lowest unoccupied molecular orbital (LUMO) than that of the material forming the electron transport layer 15 be used; and as the material forming the electron transport layer 15, it is preferable that a material having a higher electron mobility than that of the material forming the electron injection layer be used.

In addition, in order to improve electron injecting and transporting properties, it is preferable that the electron injection layer and the electron transport layer 15 be doped with a donor. As the donor, materials which are well-known in the related art as a donor material for organic EL can be used.

Examples of the donor material include inorganic materials such as alkali metals, alkaline earth metals, rare earth elements, Al, Ag, Cu and In; and organic materials such as anilines, phenylenediamines, benzidines (for example, N,N,N',N'-tetraphenylbenzidine, N,N'-bis-(3-methylphenyl)-N,N'-bis-(phenyl)-benzidine, and N,N'-di(naphthalene-1-yl)-N,N'-diphenyl-benzidine), compounds having an aromatic tertiary amine in a structure thereof such as triphenylamines (for example, triphenylamine, 4,4',4''-tris(N,N-diphenyl-amino)-triphenylamine, 4,4',4''-tris(N-3-methylphenyl-N-phenyl-amino)-triphenylamine, and 4,4',4''-tris(N-(1-naphthyl)-N-phenyl-amino)-triphenylamine), and triphenyldiamines (for example, N,N'-di-(4-methyl-phenyl)-N,N'-diphenyl-1,4-phenylenediamine), condensed polycyclic compounds (which may have a substituent; for example, phenanthrene, pyrene, perylene, anthracene, tetracene, and pentacene), TTF (tetrathiafulvalene), dibenzofuran, phenothiazine, and carbazole. Among these, compounds having an aromatic tertiary amine in a structure thereof, condensed polycyclic compounds, and alkali metals are more preferable from the viewpoint of more efficiently increasing the carrier density.

As a material forming the hole blocking layer, the above-described examples of the material forming the electron transport layer 15 and the electron injection layer can be used.

Examples of a method of forming the organic light-emitting layer 14, the hole transport layer 13, the electron transport layer 15, the hole injection layer, the electron injection layer, the hole blocking layer, the electron blocking layer and the like included in the organic EL layer 17 include methods of forming the layers using an organic EL layer-forming coating solution in which the above-described materials are dissolved and dispersed in a solvent through a well-known wet process including a coating method such as a spin coating method, a dipping method, a doctor blade method, a discharge coating method, and a spray coating method; and a printing method such as an ink jet method, a relief printing method, an intaglio printing method, a screen printing method, or a micro gravure method. Other examples thereof include methods of forming the layers using the above-described materials through a well-known dry process such as a resistance heating deposition method, an electron beam (EB) deposition method, a molecular beam epitaxy (MBE) method, a sputtering method, or an organic vapor-phase deposition (OVPD) method. Alternatively, for example, methods of forming the layers using a laser transfer method can be used. When the organic EL layer 17 is formed through a wet process, the organic EL layer-forming coating solution may contain an additive for adjusting properties of the coating solution such as a leveling agent or a viscosity adjuster.

In general, the thickness of each layer included in the organic EL layer 17 is approximately 1 nm to 1000 nm and more preferably 10 nm to 200 nm. When the thickness of each layer included in the organic EL layer 17 is less than 10 nm, there are concerns that necessary properties (injecting properties, transporting properties, and confinement properties of charge (electron and hole)) may not be obtained and images defects may occur due to foreign materials such as dust. In addition, when the thickness of each layer included in the organic EL layer 17 is greater than 200 nm, the drive voltage is increased and there is a concern that the power consumption may increase.

The first electrode 12 is formed on the substrate (not illustrated), and the second electrode 16 is formed on the organic EL layer (organic layer) 17.

As an electrode material forming the first electrode 12 and the second electrode 16, a well-known electrode material can be used. From the viewpoint of efficiently performing the injection of holes to the organic EL layer 17, examples of the material forming the first electrode 12 which is the anode include metals having a work function of 4.5 eV or higher such as gold (Au), platinum (Pt), and nickel (Ni); oxide (ITO) formed of indium (In) and tin (Sn); oxide (SnO2) of tin (Sn); and oxide (IZO) formed of indium (In) and zinc (Zn). From the viewpoint of efficiently performing the injection of electrons to the organic EL layer 17, examples of the material forming the second electrode 16 which is the cathode include metals having a work function of 4.5 eV or lower such as lithium (Li), calcium (Ca), cerium (Ce), barium (Ba), and aluminum (Al); and alloys containing these metals such as Mg:Ag alloy and Li:Al alloy.

The first electrode 12 and the second electrode 16 can be formed on the substrate using the above-described materials according to a well-known method such as an EB (electron beam) deposition method, a sputtering method, an ion plating method, or a resistance heating deposition method. However, the embodiment is not limited to these formation methods. In addition, optionally, the formed electrode can be patterned using a photolithography method or a laser lift-off method. In this case, by using a shadow mask in combination, the electrode can be directly patterned.

The thicknesses of the first electrode 12 and the second electrode 16 are preferably greater than or equal to 50 nm. When the thicknesses of the first electrode 12 and the second electrode 16 are less than 50 nm, the interconnection resistance is increased, and thus there is a concern that the drive voltage may increase.

The organic light-emitting element 10 illustrated in FIG. 1 includes the organic EL (organic layer) 17 that includes the organic light-emitting layer 14 having the above-described transition metal complex according to the embodiment. Therefore, the organic light-emitting element 10 recombines holes injected from the first electrode 12 with electrons injected from the second electrode 16 and can discharge (emit) blue light with a high efficiency using phosphorescent emission of the transition metal complex according to the embodiment contained in the organic layer 17 (organic light-emitting layer 14) as the luminescent material. In addition, when the organic layer 17 (organic light-emitting layer 14) contains a combination of the transition metal complex according to the embodiment, which is used as a host material, and a blue luminescent dopant of the related art, high-efficiency blue emission can be obtained using the blue luminescent dopant of the related art.

The organic light-emitting element according to the embodiment may have a bottom emission type device configuration in which emitted light is discharged through a substrate. The organic light-emitting element according to the embodiment may have a top emission type device configuration in which emitted light is discharged to the opposite side to a substrate. In addition, a method of driving the organic light-emitting element according to the embodiment is not particularly limited, and an active driving method or a passive driving method may be used. However, it is preferable that the organic light-emitting element be driven using an active driving method. By adopting an active driving method, the light-emitting time of the organic light-emitting element is increased as compared to a passive driving method, a drive voltage required for obtaining a desired luminance can be reduced, and the power consumption can be reduced. Therefore, an active driving method is preferable.

Figure 2:
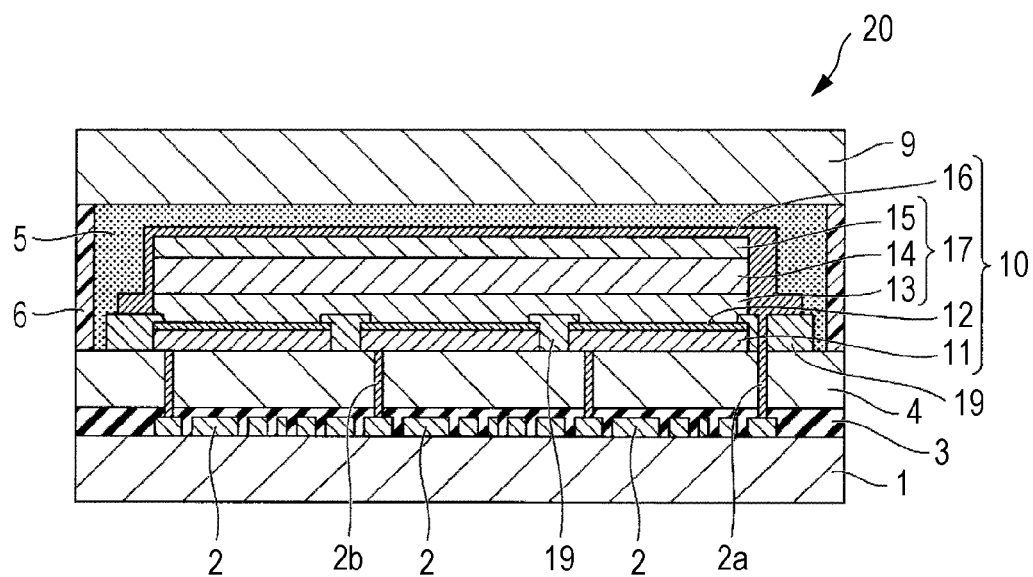
FIG. 2 is a cross-sectional view schematically illustrating a second embodiment of the organic light-emitting element according to the invention.

FIG. 2 is a cross-sectional view schematically illustrating a second embodiment of the organic light-emitting element according to the embodiment. In the organic light-emitting device 20 illustrated in FIG. 2, an organic light-emitting element 10 (hereinafter also referred to as "organic EL element 10") in which an organic EL layer (organic layer) 17 is interposed between a pair of electrodes 12 and 16 is formed on a substrate 1 that includes TFT (thin film transistor) circuits 2. The organic light-emitting device 20 is a top emission type organic light-emitting element that is driven with an active driving method. In FIG. 2, the same components as those of the organic light-emitting element 10 illustrated in FIG. 1 are represented by the same reference numerals, and the description thereof will not be repeated.

Briefly, the organic light-emitting device 20 illustrated in FIG. 2 includes the substrate 1, the organic EL element 10, an inorganic sealing film 5, a sealing substrate 9, and a sealing material 6. The substrate 1 includes the TFT (thin film transistor) circuits 2. The organic EL element 10 is provided on the substrate 1 with an interlayer dielectric 3 and a planarizing film 4 interposed therebetween. The inorganic sealing film 5 covers the organic EL element 10. The sealing substrate 9 is provided on the inorganic sealing film 5. A gap between the substrate 1 and the sealing substrate 9 is filled with the sealing material 6. In the organic EL element 10, the organic EL layer (organic layer) 17, in which the hole transport layer 13, the light-emitting layer 14, and the electron transport layer 15 are laminated as in the case of the first embodiment, is interposed between the first electrode 12 and the second electrode 16. A repeller 11 is formed on a lower surface of the first electrode 12. The repeller 11 and the first electrode 12 are connected to one of the TFT circuits 2 through an interconnection 2b which penetrates the interlayer dielectric 3 and the planarizing film 4. The second electrode 16 is connected to one of the TFT circuits 2 through an interconnection 2a which penetrates the interlayer dielectric 3, the planarizing film 4, and an edge cover 19.

The TFT circuits 2 and various interconnections (not illustrated) are formed on the substrate 1. Furthermore, the interlayer dielectric 3 and the planarizing film 4 are sequentially laminated so as to cover an upper surface of the substrate 1 and the TFT circuits 2.

Examples of the substrate 1 include inorganic material substrates formed of glass, quartz, or the like; plastic substrates formed of polyethylene terephthalate, polycarbazole, polyimide, or the like; insulating substrates such as a ceramic substrate formed of alumina or the like; metal substrates formed of aluminum (Al), iron (Fe), or the like; substrates obtained by coating a surface of the above-described substrates with an organic insulating material such as silicon oxide ($SiO_2$); and substrates obtained by performing an insulation treatment on a surface of a metal substrate formed of Al or the like using a method such as anodic oxidation. However, the embodiment is not limited thereto.

The TFT circuits 2 are formed on the substrate 1 in advance before forming the organic light-emitting element 20 and have a switching function and a driving function. As the TFT circuits 2, well-known TFT circuits 2 of the related art can be used. In addition, in the embodiment, for the switching and driving functions, metal-insulator-metal (MIM) diodes can be used instead of TFTs.

The TFT circuits 2 can be formed using a well-known material, structure, and formation method. Examples of a material of an active layer of the TFT circuits 2 include inorganic semiconductor materials such as amorphous silicon, polycrystalline silicon (polysilicon), microcrystalline silicon, and cadmium selenide; oxide semiconductor materials such as zinc oxide and indium oxide-gallium oxide-zinc oxide; and organic semiconductor materials such as polythiophene derivatives, thiophene oligomers, poly(p-phenylenevinylene) derivatives, naphthacene, and pentacene. In addition, examples of a structure of the TFT circuits 2 include a staggered type, an inverted staggered type, a top-gate type, and a coplanar type.

A gate insulator of the TFT circuits 2 used in the embodiment can be formed of a well-known material. Examples of the material include $SiO_2$ which is formed using a plasma-enhanced chemical vapor deposition (PECVD) method, a low pressure chemical vapor deposition (LPCVD), or the like; and $SiO_2$ obtained by thermally oxidizing a polysilicon film. In addition, a signal electrode line, a scanning electrode line, and a common electrode line of the TFT circuits 2, the first electrode, and the second electrode which are used in the embodiment can be formed of a well-known material, and examples thereof include tantalum (Ta), aluminum (Al), and copper (Cu).

The gate insulator 3 can be formed of a well-known material, and examples thereof include inorganic materials such as silicon oxide ($SiO_2$), silicon nitride (SiN or $Si_2N_4$), tantalum oxide (TaO or $Ta_2O_5$); and organic materials such as acrylic resins and resist materials.

Examples of a method of forming the interlayer dielectric 3 include a dry process such as a chemical vapor deposition (CVD) method and a vacuum deposition method; and a wet process such as a spin coating method. In addition, optionally, patterning can be performed using a photolithography method or the like.

In the organic light-emitting element 20 according to the embodiment, light emitted from the organic EL element 10 is extracted from the sealing substrate 9 side. Therefore, in order to prevent TFT properties of the TFT circuits 2, formed on the substrate 1, from being changed by light incident from outside, it is preferable that the light-shielding interlayer dielectric 3 (light-shielding insulating film) be used. In addition, in the embodiment, the interlayer dielectric 3 and the light-shielding insulating film can be used in combination. Examples of the light-shielding insulating film include polymer resins such as polyimide in which a pigment or a dye such as phthalocyanine or quinacridone is dispersed; color resists; black matrix materials; and inorganic insulating materials such as and $Ni_xZn_yFe_2O_4$.

The planarizing film 4 is provided for preventing defects of the organic EL element 10 (for example, a defect of a pixel electrode, a defect of the organic EL layer, disconnection of a counter electrode, short-circuiting between a pixel electrode and a counter electrode, or reduction in withstand voltage) caused by convex and concave portions on a surface of the TFT circuits 2. The planarizing film 4 may not be provided.

The planarizing film 4 can be formed of a well-known material, and examples thereof include inorganic materials such as silicon oxide, silicon nitride, and tantalum oxide; and organic materials such as polyimide, acrylic resins, and resist materials. Examples of a method of forming the planarizing film 4 include a dry process such as a CV method and a vacuum deposition method; and a wet process such as a spin coating method. However, the embodiment is not limited to these materials and formation methods. In addition the planarizing film 4 may have a single-layer structure or a multilayer structure.

In the organic light-emitting element 20 according to the embodiment, light emitted from the organic light-emitting layer 14 of the organic EL element 10, which is a light source, is extracted from the second electrode 16 side which is the sealing substrate 9 side. Therefore, as the second electrode 16, it is preferable that a semitransparent electrode be used. As a material of the semitransparent electrode, a metal semitransparent electrode may be used alone; or a metal semitransparent electrode and a transparent electrode material may be used in combination. From the viewpoints of reflectance and transparency, silver or silver alloys are preferable.

In the organic light-emitting element 20 according to the embodiment, as the first electrode 12 that is disposed on the opposite side to the side of extract light from the organic light-emitting layer 14, in order to increase the efficiency of extract light from the organic light-emitting layer 14, it is preferable that an electrode (repeller) having high light reflectance be used. Examples of an electrode material used at this time include a reflective metal electrode such as aluminum, silver, gold, aluminum-lithium alloys, aluminum-neodymium alloys, or aluminum-silicon alloys; and electrodes obtained by combining a transparent electrode and the above-described reflective metal electrode (repeller). FIG. 2 illustrates an example in which the first electrode 12, which is the transparent electrode, is formed on the planarizing film 4 with the repeller 11 interposed therebetween.

In addition, in the organic light-emitting element 20 according to the embodiment, plural first electrodes 12 that are arranged on the substrate 1 side (opposite side to the side of extract light from the organic light-emitting layer 14) are provided in parallel so as to correspond to respective pixels; and the edge cover 19 that is formed of an insulating material so as to cover respective edge portions (end portions) of first electrodes 12 and 12 adjacent to each other is formed. This edge cover 19 is provided for preventing leakage between the first electrode 12 and the second electrode 16. The edge cover 19 can be formed of an insulating material with a well-known method such as an EB deposition method, a sputtering method, an ion plating method, or a resistance heating deposition method. In addition, patterning can be performed using a well-known dry or wet photolithography method. However, the embodiment is not limited to these formation methods. In addition, as the insulating material forming the edge cover 19, a well-known material of the related art can be used. The insulating material is not particularly limited in the embodiment, and examples thereof include SiO, SiON, SiN, SiOC, SiC, HfSiON, ZrO, HfO, and LaO.

The thickness of the edge cover 19 is preferably 100 nm to 2000 nm. When the thickness of the edge cover 19 is greater than or equal to 100 nm, sufficient insulating property can be secured. As a result, an increase in power consumption and non-emission, leakage occurs between the first electrode 12 and the second electrode 16, can be prevented. In addition, when the thickness of the edge cover 19 is less than or equal to 2000 nm, deterioration in the productivity of a film-forming process and disconnection of the second electrode 16 in the edge cover 19 can be prevented.

In addition, the repeller 11 and the first electrode 12 are connected to one of the TFT circuits 2 through the interconnection 2b which penetrates the interlayer dielectric 3 and the planarizing film 4. The second electrode 16 is connected to one of the TFT circuits 2 through the interconnection 2a which penetrates the interlayer dielectric 3, the planarizing film 4, and the edge cover 19. The interconnections 2a and 2b are not particularly limited as long as they are formed of a conductive material such as Cr, Mo, Ti, Ta, Al, Al alloys, Cu, or Cu alloys. The interconnections 2a and 2b are formed using a well-known method of the related art such as a sputtering method or CVD method and a mask process.

The inorganic sealing film 5 that is formed of SiO, SiON, SiN, or the like is formed so as to cover the upper surface and side surface of the organic EL element 10 formed on the planarizing film 4. The inorganic sealing film 5 can be formed by forming an inorganic film of SiO, SiON, SiN, or the like with a plasma CVD method, an ion plating method, an ion beam method, a sputtering method, or the like. In order to extract light having a wavelength which is converted by a wavelength-converting layer 18, it is necessary that the inorganic sealing film 5 be light-transmissive.

The sealing substrate 9 is provided on the inorganic sealing film 5, and the organic light-emitting element 10, formed between the substrate 1 and the sealing substrate 9, is sealed in a sealing region surrounded by the sealing material 6.

By providing the inorganic sealing film 5 and the sealing material 6, oxygen or water can be prevented from being mixed into the organic EL layer 17 from outside. As a result, the lifetime of the organic light-emitting element 20 can be improved.

As a material forming the sealing substrate 9, the same materials as those of the above-described substrate 1 can be used. However, since the organic light-emitting element 20 according to the embodiment extracts light from the sealing substrate 9 side (when the observer observes emission from the outside of the sealing substrate 9), it is necessary that the sealing substrate 9 be light-transmissive. In addition, in order to improve color purity, a color filter may be formed on the sealing substrate 9.

As the sealing material 6, a well-known sealing material of the related art can be used. In addition, as a method of forming the sealing material 6, a well-known sealing method of the related art can be used.

As the sealing material 6, for example, a resin (curing resin) can be used. In this case, the upper surface and/or side surface of the inorganic sealing film 5 of the substrate 1 on which the organic EL element 10 and the inorganic sealing film 5 are formed; or the sealing substrate 9 is coated with a curing resin (photocurable resin, thermosetting resin) using a spin coating method or a laminate method. Then, the substrate 1 and the sealing substrate 9 are bonded to each other through the resin layer to perform photo-curing or thermal curing. As a result, the sealing material 6 can be formed. It is necessary that the sealing material 6 be light-transmissive.

In addition, as the sealing material 6, inactive gas such as nitrogen gas or argon gas may be used. For example, a method of sealing inactive gas such as nitrogen gas or argon gas with the sealing substrate 9 such as a glass substrate may be used.

In this case, in order to efficiently reduce deterioration of the organic EL portion caused by water, it is preferable that a moisture absorbent such as barium oxide or the like be mixed into inorganic gas to be sealed.

As in the case of the organic light-emitting element 10 according to the first embodiment, the organic EL layer (organic layer) 17 of the organic light-emitting device 20 according to the embodiment also contains the transition metal complex according to the embodiment. Therefore, the organic light-emitting element 20 recombines holes injected from the first electrode 12 with electrons injected from the second electrode 16 and can discharge (emit) blue light with a high efficiency using phosphorescent emission of the transition metal complex according to the embodiment contained in the organic layer 17 (organic light-emitting layer 14) as the luminescent material. In addition, when the organic layer 17 (organic light-emitting layer 14) contains a combination of the transition metal complex according to the embodiment, which is used as a host material, and a blue luminescent dopant of the related art, high-efficiency blue emission can be obtained using the blue luminescent dopant of the related art.

<Color-Converting Light-Emitting Element>

A color-converting light-emitting element according to an embodiment of the invention includes a light-emitting element; and a phosphor layer that is disposed on a side of extract light from the light-emitting element, absorbs light emitted from the light-emitting element, and emits light having a different color from that of the absorbed light.

Figure 3:
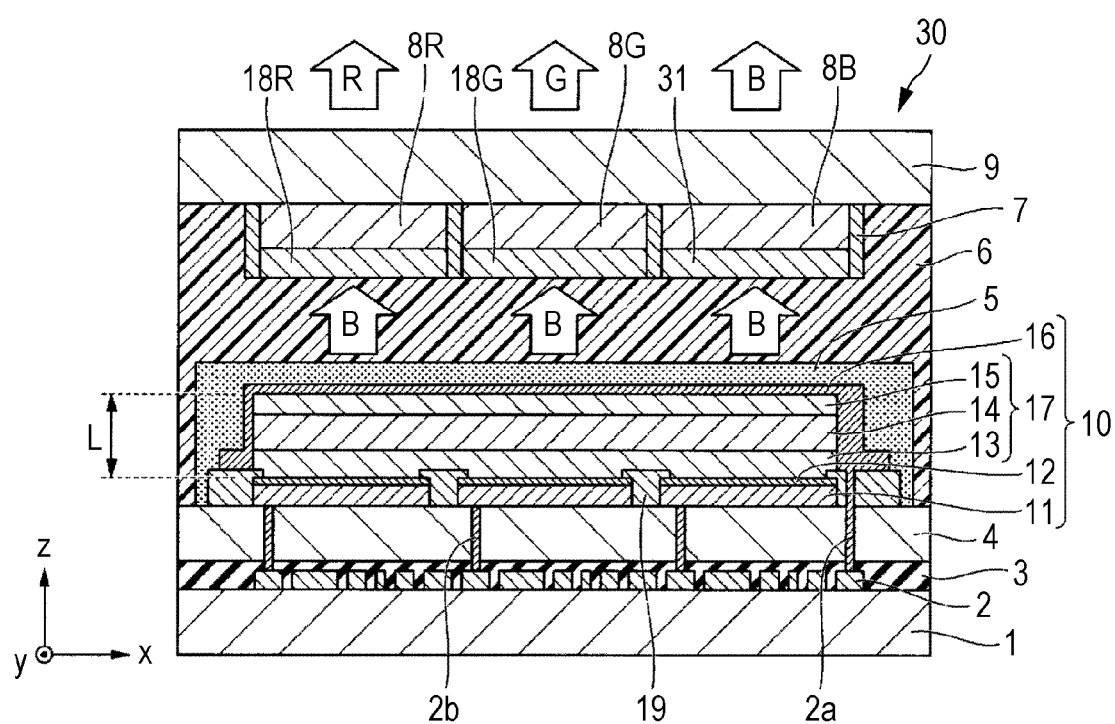
FIG. 3 is a cross-sectional view illustrating an embodiment of a color-converting light-emitting element according to the invention.
Figure 4:
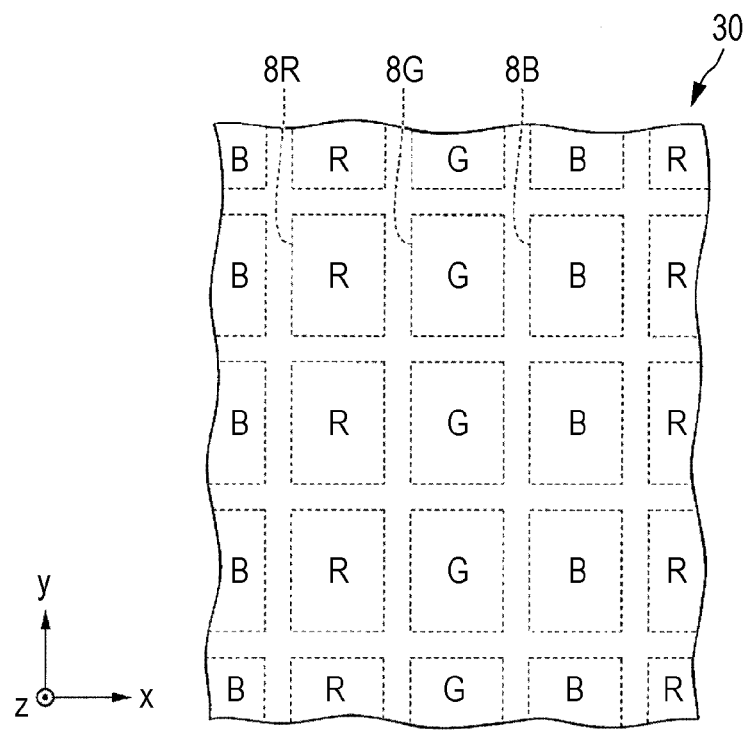
FIG. 4 is a top view illustrating the color-converting light-emitting element of FIG. 3.

FIG. 3 is a cross-sectional view illustrating a first embodiment of the color-converting light-emitting element according to the embodiment, and FIG. 4 is a top view illustrating the organic light-emitting element of FIG. 3. A color-converting light-emitting element 30 illustrated in FIG. 3 includes a red phosphor layer 18R that absorbs blue light emitted from the above-described organic light-emitting element according to the embodiment and converts the blue light into red light; and a green phosphor layer 18G that absorbs blue light and converts the blue light into green light. Hereinafter, the red phosphor layer 18R and the green phosphor layer 18G are also collective referred to as "phosphor layers". In the color-converting light-emitting element 30 illustrated in FIG. 3, the same components as those of the organic light-emitting element 10 and the organic light-emitting device 20 are represented by the same reference numerals and the description thereof will not be repeated.

Briefly, the color-converting light-emitting element 30 illustrated in FIG. 3 includes a substrate 1, an organic light-emitting element (light source) 10, a sealing substrate 9, a red color filter 8R, a green color filter 8G, a blue color filter 8B, the red phosphor layer 18R, the green phosphor layer 18G, and a scattering layer 31. The substrate 1 includes TFT (thin film transistor) circuits 2. The organic light-emitting element (light source) 10 is formed on the substrate 1 with an interlayer dielectric 3 and a planarizing film 4 interposed therebetween. The red color filter 8R, the green color filter 8G, and the blue color filter 8B are partitioned by a black matrix 7 and disposed in parallel on one surface of the sealing substrate 9. The red phosphor layer 18R is aligned and formed on the red color filter 8R formed on one surface of the sealing substrate 9. The green phosphor layer 18G is aligned and formed on the green color filter 8G formed on one surface of the sealing substrate 9. The scattering layer 31 is aligned and formed on the blue color filter 8B formed on the sealing substrate 9. The substrate 1 and the sealing substrate 9 are disposed such that the organic light-emitting element 10 is disposed opposite the respective phosphor layers 18R and 18G and the scattering layer 31 with a sealing material interposed therebetween. The red phosphor layer 18R and the green phosphor layer 18G and the scattering layer 31 are partitioned by the black matrix 7.

The organic light-emitting element (organic EL light-emitting portion) 10 is covered with the inorganic sealing film 5. In the organic EL light-emitting portion 10, the organic EL layer (organic layer) 17 in which a hole transport layer 13, a light-emitting layer 14, and an electron transport layer 15 are laminated is interposed between a first electrode 12 and a second electrode 16. A repeller 11 is formed on a lower surface of the first electrode 12. The repeller 11 and the first electrode 12 are connected to one of the TFT circuits 2 through an interconnection 2b which penetrates the interlayer dielectric 3 and the planarizing film 4. The second electrode 16 is connected to one of the TFT circuits 2 through an interconnection 2a which penetrates the interlayer dielectric 3, the planarizing film 4, and an edge cover 19.

In the color-converting light-emitting element 30 according to the embodiment, light emitted from the organic light-emitting element 10, which is a light source, is incident to the respective phosphor layers 18R and 18G and the scattering layer 31; this incident layer transmits through the scattering layer 31 without any change; the respective phosphor layers 18R and 18G converts the incident light into light beams of three colors including red, green, and blue; and the converted three light beams are emitted to the sealing substrate 9 side (observer side).

In FIG. 3, in order to make the drawing more recognizable, an example of the color-converting light-emitting element 30 according to the embodiment is illustrated in which the red phosphor layer 18R and the red color filter 8R, the green phosphor layer 18G and the green color filter 8G, and the scattering layer 31 and the blue color filter 8B are disposed in parallel, respectively. However, as illustrated in FIG. 4, the respective color filters 8R, 8G, and 8B surrounded by broken lines have a two-dimensional stripe arrangement in which the respective color filters 8R, 8G, and 8B extend in a stripe shape along the y-axis and are sequentially arranged along the x-axis.

In an example of FIG. 4, the respective RGB pixels (respective color filters 8R, 8G, and 8B) are arranged in a stripe shape, but the embodiment is not limited thereto. The arrangement of the respective RGB pixels can be a well-known RGB pixel arrangement such as a mosaic arrangement or a delta arrangement.

The red phosphor layer 18R absorbs light in a blue wavelength range emitted from the organic light-emitting element 10, which is a light source; converts the light in a blue wavelength range into light in a red wavelength range; and emits the light in a red wavelength range to the sealing substrate 9 side.

The green phosphor layer 18G absorbs light in a blue wavelength range emitted from the organic light-emitting element 10, which is a light source; converts the light in a blue wavelength range into light in a green wavelength range; and emits the light in a green wavelength range to the sealing substrate 9 side.

The scattering layer 31 is provided for improving the viewing angle characteristic and extraction efficiency of light in a blue wavelength range emitted from the organic light-emitting element 10 which is a light source; and emits the light in a blue wavelength range to the sealing substrate 9 side. The scattering layer 31 may not be provided.

In this way, by providing the red phosphor layer 18R and the green phosphor layer 18G (and the scattering layer 31), light emitted from the organic light-emitting element 10 is converted into light beams of three colors including red, green, and blue; and the converted light beams are emitted to the sealing substrate 9 side, thereby making full-color display possible.

The color filters 8R, 8G, and 8B that are disposed between the sealing substrate 9 on the light extraction side (observer side) and the phosphor layers 18R and 18G and the scattering layer 31 are provided for improving the color purity of red, green, and blue light beams emitted from the color-converting light-emitting element 30; and for enlarging the color reproduction range of the color-converting light-emitting element 30. In addition, the red color filter 8R that is formed on the red phosphor layer 18R and the green color filter 8G that is formed on the green phosphor layer 18G absorb blue components and ultraviolet components of outside light. Therefore, the emission of the respective phosphor layers 8R and 8G caused by outside light can be reduced and prevented; and deterioration in contrast can be reduced and prevented.

The color filters 8R, 8G, and 8B are not particularly limited, and well-known color filters of the related art can be used. In addition, likewise, as a method of forming the color filters 8R, 8G, and 8B, a well-known method of the related art can be used. The thickness thereof can also be appropriately adjusted.

The scattering layer 31 has a configuration in which transparent particles are dispersed in a binder resin. The thickness of the scattering layer 31 is normally 10 μm to 100 μm and preferably 20 μn to 50 μm.

As the binder resin used for the scattering layer 31, a well-known resin of the related art can be used. The binder resin is not particularly limited, but a light-transmissive resin is preferable. The transparent particles are not particularly limited as long as light emitted from the organic light-emitting element 10 are scattered by and pass through the transparent particles. For example, polystyrene particles having an average particle size of 25 μm and a standard deviation of particle size distribution of 1 μm can be used. In addition, the content of the transparent particles in the scattering layer 31 can be appropriately changed and is not particularly limited.

The scattering layer 31 can be formed using a well-known method of the related art, and the formation method is not particularly limited. Examples of the formation method include methods of forming the layer using a coating solution in which a binder resin and transparent particles are dissolved and dispersed in a solvent through a well-known wet process including a coating method such as a spin coating method, a dipping method, a doctor blade method, a discharge coating method, and a spray coating method; and a printing method such as an ink jet method, a relief printing method, an intaglio printing method, a screen printing method, or a micro gravure method.

The red phosphor layer 18R contains a phosphor material capable of absorbing light in a blue wavelength range emitted from the organic light-emitting element 10 to be excited; and emitting fluorescence in a red wavelength range.

The green phosphor layer 18G contains a phosphor material capable of absorbing light in a blue wavelength range emitted from the organic light-emitting element 10 to be excited; and emitting fluorescence in a green wavelength range.

The red phosphor layer 18R and the green phosphor layer 18G may be formed of the following exemplary phosphor materials alone; may further contain an additive or the like as necessary; and may have a configuration in which these materials are dispersed in a polymer material (binder resin) or in an inorganic material.

As the phosphor material forming the red phosphor layer 18R and the green phosphor layer 18G, well-known phosphor materials of the related art can be used. Such phosphor materials are divided into organic phosphor materials and inorganic phosphor materials. Specific exemplary compounds of these phosphor materials are described below, but the embodiment is not limited to these materials.

First, examples of the organic phosphor materials will be described. As a phosphor material used for the red phosphor layer 18R, a fluorescent dye which converts ultraviolet or blue excitation light into red light to be emitted is used, and examples thereof include cyanine-based dyes such as 4-dicyanomethylene-2-methyl-6-(p-dimethylaminostyryl)-4H-pyran; pyridine-based dyes such as 1-ethyl-2-[4-(p-dimethylamino phenyl)-1,3-butadienyl]-pyridinium-perchlorate; and rhodamine-based dyes such as rhodamine B, rhodamine 6G, rhodamine 3B, rhodamine 101, rhodamine 110, basic violet 11, and sulforhodamine 101. In addition, as a phosphor material used for the green phosphor layer 18G, a fluorescent dye which converts ultraviolet or blue excitation light into green light to be emitted is used, and examples thereof include coumarin-based dyes such as 2,3,5,6-1H,4H-tetrahydro-8-trifluomethyl quinolizine(9,9a,1-gh)coumarin (coumarin 153), 3-(2'-benzothiazolyl)-7-diethylamino coumarin (coumarin 6), 3-(2'-benzoimidazolyl)-7-N,N-diethylamino coumarin (coumarin 7); and naphthalimide-based dyes such as basic yellow 51, solvent yellow 11, and solvent yellow 116.

Next, examples of the inorganic phosphor materials will be described. As a phosphor material used for the red phosphor layer 18R, a phosphor which converts ultraviolet or blue excitation light into green light to be emitted is used, and examples thereof include $(BaMg)Al_{16}O_{27}:Eu^{2+}, Mn^{2+}$, $Sr_4Al_{14}O_{25}: Eu^{2+}$, $(SrBa) Al_{12}Si_2O_8: Eu^{2+}$, $(BaMg)_2SiO_4: Eu^{2+}$, $Y_2SiO_5:Ce_{3+}$, $Tb^{3+}$, $Sr_2P_2O_7\text{—}Sr_2B_2O_5:Eu^{2+}$, $(BaCaMg)_5 (PO_4)_3Cl:EU^{2+}$, $Sr_2Si_3O_8\text{-}2SrCl_2:Eu^{2+}$, $Zr_2SiO_4$, $MgAl_{11}O_{19}:Ce^{3+}$, $Tb^{3+}$, $Ba_2SiO_4:Eu^{2+}$, $Sr_2SiO_4:Eu^{2+}$, and $(BaSr)SiO_4:Eu^{2+}$. As a phosphor material used for the green phosphor layer 18G, a phosphor which converts ultraviolet or blue excitation light into red light to be emitted is used, and examples thereof include $Y_2O_2S:Eu^{3+}$, $YAlO_3:EU^{3+}$, $Ca_2Y_2 (SiO_4)_6:EU^{3+}$, $LiY_9 (SiO_4)_6O_2:EU^{3+}$, $YVO_4:EU^{3+}$, $CaS:Eu^{3+}$, $Gd_2O_3:Eu^{3+}$, $Gd_2O_2S:Eu^{3+}$, $Y(P,V)O_4:Eu^{3+}$, $Mg_4GeO_{5.5}F:Mn^{4+}$, $Mg_4GeO_6:Mn^{4+}$, $K_5Eu_{2.5}(WO_4)_{6.25}$, $Na_5Eu_{2.5}(WO_4)_{6.25}$, $K_5Eu_{2.5}(MoO_4)_{6.25}$, and $Na_5Eu_{2.5}(MoO_4)_{6.25}$.

In the color-converting light-emitting element 30 according to the embodiment, instead of the scattering layer 31, a blue phosphor layer may be provided that absorbs light in an ultraviolet wavelength range emitted from the organic light-emitting element 10, which is a light source; converts the light in an ultraviolet wavelength range into light in a blue wavelength range; and emits the light in a blue wavelength range to the sealing substrate 9 side.

In this case, as an organic phosphor material used for the blue phosphor layer, a fluorescent dye which converts ultraviolet excitation light into blue light to be emitted is used, and examples thereof include stilbenzene dyes such as 1,4-bis(2-methylstyryl)benzene and trans-4,4'-diphenylstilbenzene; and coumarin dyes such as 7-hydroxy-4-methylcoumarin. In addition, as an inorganic phosphor material, a phosphor which converts ultraviolet excitation light into blue light to be emitted is used, and examples thereof include $Sr_2P_2O_7:Sn^{4+}$, $Sr_4Al_{14}O^{25}:Eu^{2+}$, $BaMgAl_{10}O_{17}:Eu^{2+}$, $SrGa_2S_4:Ce^{3+}$, $CaGa_2S_4:Ce^{3+}$, (Ba, Sr) (Mg, Mn)$Al_{10}O_{17}:Eu^{2+}$, (Sr, Ca, Ba$_2$, Mg)$_{10}(PO_4)_6Cl_2:Eu^{2+}$, $BaAl_2SiO_8:Eu^{2+}$, $Sr_2P_2O_7:Eu^{2+}$, $Sr_5(PO_4)_3Cl:Eu^{2+}$, (Sr,Ca,Ba)$_5(PO_4)_3Cl$: $EU^{2+}$, $BaMg_2Al_{16}O_{27}$: $Eu^{2+}$, $(Ba,Ca)_5(PO_4)_3Cl:Eu^{2+}$, $Ba_3MgSi_2O_8:Eu^{2+}$, and $Sr_3MgSi_2O_8:Eu^{2+}$.

Optionally, it is preferable that the above-described inorganic phosphor materials be subjected to a surface reforming treatment. Examples of a method of the surface reforming treatment include a chemical treatment using a silane coupling agent and the like; a physical treatment of adding submicron-order particles and the like; and a combination of the above-described methods. When deterioration caused by excitation light and deterioration caused by emission are taken into consideration, it is preferable that the inorganic phosphor materials be used from the viewpoint of stability. In addition, when the inorganic phosphor materials are used, it is preferable that the average particle size (d50) of the materials be 0.5 µm to 50 µm.

In addition, when the red phosphor layer 18R and the green phosphor layer 18G have a configuration in which the above-described phosphor materials are dispersed in a polymer material (binder resin), patterning can be performed with a photolithography method by using a photosensitive resin as the polymer material. Here, as the photosensitive layer, one kind or a mixture of plural kinds selected from photosensitive resins (photocurable resist materials) having a reactive vinyl group such as acrylic acid-based resins, methacrylic acid-based resins, polyvinyl cinnamate-based resins, and vulcanite-based resins can be used.

In addition, the red phosphor layer 18R and the green phosphor layer 18G can be formed according to a well-known wet process, dry process, or laser transfer method using a phosphor layer-forming coating solution in which the above-described phosphor materials (pigments) and binder resin are dissolved and dispersed in a solvent. Here, examples of the well-known wet process include a coating method such as a spin coating method, a dipping method, a doctor blade method, a discharge coating method, and a spray coating method; and a printing method such as an ink jet method, a relief printing method, an intaglio printing method, a screen printing method, or a micro gravure method. In addition, examples of the well-known dry process include a resistance heating deposition method, an electron beam (EB) deposition method, a molecular beam epitaxy (MBE) method, a sputtering method, or an organic vapor-phase deposition (OVPD) method.

The thicknesses of the red phosphor layer 18R and the green phosphor layer 18G are normally 100 nm to 100 µm and preferably 1 µm to 100 µm. When the thickness of each of the red phosphor layer 18R and the green phosphor layer 18G is less than 100 nm, it is difficult to sufficiently absorb blue light emitted from the organic light-emitting element 10. Therefore, there are cases in which the luminous efficiency of the light-converting light-emitting element 30 may deteriorate or blue transmitted light may be mixed into light converted by the respective phosphor layers 18R and 18G; and, as a result, the color purity may deteriorate. In addition, in order to improve the absorption of blue light emitted from the organic light-emitting element 10 and to reduce blue transmitted light to a degree that does not have adverse effects on color purity, it is preferable that the thickness of each of the phosphor layers 18R and 18G be greater than or equal to 1 µm. Even if the thickness of each of the red phosphor layer 18R and the green phosphor layer 18G is greater than 100 µm, the luminous efficiency of the light-converting light-emitting element 30 is not increased because blue light emitted from the organic light-emitting element 10 is already sufficiently absorbed. Therefore, since an increase in material cost can be suppressed, it is preferable that the thickness of each of the red phosphor layer 18R and the green phosphor layer 18G be less than or equal to 100 µm.

The inorganic sealing film 5 is formed so as to cover the upper surface and side surface of the organic EL element 10. Further, the red phosphor layer 18R, the green phosphor layer 18G, the scattering layer 31, and the respective color filters 8R, 8G, and 8B are partitioned by the black matrix 7 and disposed in parallel on one surface of the sealing substrate 9, and the sealing substrate 9 is disposed on the inorganic sealing film 5 such that the respective phosphor layers 18R and 18G and the scattering layer 31 are disposed opposite the organic light-emitting element. A gap between the inorganic sealing film 5 and the sealing substrate 9 is filled with a sealing material 6. That is, each of the respective phosphor layers 18R and 18G and the scattering layer 31 that are disposed opposite the organic light-emitting element 10 is partitioned by being surrounded by the black matrix 7; and is sealed in a sealing region surrounded by the sealing material 6.

When a resin (curing resin) is used as the sealing material 6, the inorganic sealing film 5 of the substrate 1 on which the organic light-emitting element 10 and the inorganic sealing film 5 are formed; or the respective phosphor layers 18R and 18G and the scattering layer 31 of the sealing substrate 9 on which the respective phosphor layers 18R and 18G, the scattering layer 31, and the respective color filters 8R, 8G, and 8B are formed, are coated with a curing resin (photocurable resin, thermosetting resin) using a spin coating method or a laminate method. Then, the substrate 1 and the sealing substrate 9 are bonded to each other through the resin layer to perform photo-curing or thermal curing. As a result, the sealing material 6 can be formed.

It is preferable that opposite surfaces of the respective phosphor layers 18R and 18G and the scattering layer 31 to the sealing substrate 9 be planarized by the planarizing film (not illustrated) and the like. As a result, when the organic light-emitting element 10 is disposed opposite and comes into close contact with the respective phosphor layers 18R and 18G and the scattering layer 31 with the sealing material 6 interposed therebetween, a gap between the organic light-emitting element 10 and the respective phosphor layers 18R and 18G and the scattering layer 31 can be prevented. Further, the adhesion between the substrate 1, on which the organic light-emitting element 10 is formed, and the sealing substrate 9 on which the respective phosphor layers 18R and 18G, the scattering layer 31, and the color filters 8R, 8G, and 8B are formed can be improved. As the planarizing film, for example, the same film as the above-described planarizing film 4 can be used.

A material and a formation method of the black matrix 7 are not particularly limited, and a well-known material and formation method of the related art can be used. Among these, it is preferable that the black matrix 7 be formed of a material which further reflects light, which is incident to and scattered by the respective phosphor layers 18R and 18G, to the respective phosphor layers 18R and 18G, for example, a light-reflecting metal.

It is preferable that the organic light-emitting element 10 have a top emission type such that a large amount of light can reach the respective phosphor layers 18R and 18B and the scattering layer 31. At this time, it is preferable that repellers be used as the first electrode 12 and the second electrode 16; and the optical distance L between these electrode 12 and 16 be adjusted to form a microresonator structure (microcavity structure). In this case, it is preferable that a repeller be used as the first electrode 12; and a semitransparent electrode be used as the second electrode 16.

As a material of the semitransparent electrode, a semitransparent metal electrode may be used alone; or a combination of a semitransparent metal electrode and a transparent electrode material may be used. In particular, as the material of the semitransparent material, silver or silver alloys are preferable from the viewpoints of reflectance and transparency.

It is preferable that the thickness of the second electrode 16 which is the semitransparent electrode be 5 nm to 30 nm. When the thickness of the semitransparent electrode is less than 5 nm, light is not sufficiently reflected and thus there is a possibility that an interference effect may be insufficiently obtained. In addition, when the thickness of the semitransparent electrode is greater than 30 nm, the light transmittance rapidly deteriorates and thus there is a concern that luminance and efficiency may deteriorate.

In addition, it is preferable that an electrode having high light reflectance be used as the first electrode 12 which is the repeller. Examples of the repeller include a reflective metal electrode such as aluminum, silver, gold, aluminum-lithium alloys, aluminum-neodymium alloys, or aluminum-silicon alloys. As the repeller, a transparent electrode and the above-described reflective metal electrode may be used in combination. In FIG. 3, an example in which the first electrode 12 which is the transparent electrode is formed on the planarizing film 4 with the repeller 11 interposed therebetween is illustrated.

When the microresonator structure (microcavity) structure is formed by the first electrode 12 and the second electrode 16, light emitted from the organic EL layer 17 is collected in the front direction (light extraction direction: sealing substrate 9 side) due to an interference effect between the first electrode 12 and the second electrode 16. That is, since directivity can be given to light emitted from the organic EL layer 17, light loss escaping to the vicinity can be reduced, and thus the luminous efficiency can be improved. As a result, the light emission energy emitted from the organic light-emitting element 10 can be propagated to the respective phosphor layers 18R and 18B with a higher efficiency; and the luminance on the front side of the color-converting light-emitting element 30 can be increased.

In addition, due to the above-described microresonator structure, the emission spectrum of the organic EL layer 17 can be adjusted; and a desired emission peak wavelength and full width at half maximum can be obtained. Therefore, the emission spectrum of the organic EL layer 17 can be adjusted to the spectrum capable of effectively exciting phosphors in the phosphor layers 18R and 18B.

By using a semitransparent electrode as the second electrode 16, light, emitted to the opposite direction to the light extraction direction of the respective phosphor layers 18R and 18B and the scattering layer 31, can be reused.

In the respective phosphor layer 18R and 18G, the optical distance from an emission position of converted light to a light extraction surface is set to vary depending on each color of the light-emitting element. In the light-converting light-emitting element 30 according to the embodiment, the above-described "emission position" is set to a surface of the respective phosphor layers 18R and 18G opposite the organic light-emitting element 10 side.

Here, in the respective phosphor layer 18R and 18G, the optical distance from an emission position of converted light to a light extraction surface can be adjusted by the thickness of the respective phosphor layers 18R and 18G. The thickness of the respective phosphor layers 18R and 18G can be adjusted by changing printing conditions in a screen printing method (attack pressure of squeegee, attack angle of squeegee, squeegee speed, or clearance width), the specification of a screen printing plate (selection of screen printing gauze, thickness of emulsion, tension, or strength of frame), and the specification of a phosphor layer-forming coating solution (viscosity, fluidity, or mixing ratios of resin, pigment, and solvent).

In the light-converting light-emitting element 30 according to the embodiment, light emitted from the organic light-emitting element 10 can be amplified by the microresonator structure (microcavity structure); and the light extraction efficiency of light converted by the respective phosphor layers 18R and 18B can be improved by adjusting the above-described optical distance (by adjusting the thickness of the respective phosphor layers 18R and 18B). As a result, the luminous efficiency of the light-converting light-emitting element 30 can be further improved.

The light-converting light-emitting element 30 according to the embodiment has a configuration in which light, emitted from the organic light-emitting element 10 containing the above-described transition metal complex according to the embodiment, is converted by the phosphor layers 18R and 18B. Therefore, light can be emitted with a high efficiency.

Hereinabove, the light-converting light-emitting element according to the embodiment has been described. However, the light-converting light-emitting element according to the embodiment is not limited thereto. For example, in the light-converting light-emitting element 30, it is preferable that a polarizer be provided on the light extraction surface (upper surface of the sealing substrate 9). As the polarizer, a well-known linear polarizer and a well-known λ/4 polarizer of the related art can be used in combination. Here, by providing the polarizer, outside light reflection from the first electrode 12 and the second electrode 16; or outside light reflection from a surface of the substrate 1 or the sealing substrate 9 can be prevented; and the contrast of the light-converting light-emitting element 30 can be improved.

In addition, in the above-described embodiment, the organic light-emitting element 10 containing the above-described transition metal complex according to the embodiment is used as a light source (light-emitting element). However, the embodiment is not limited thereto. Another configuration can be adopted in which a light source such as an organic EL, an inorganic EL, or an LED (light-emitting diode) containing another luminescent material is used as a light-emitting element; and a layer containing the transition metal complex according to the embodiment is provided as a phosphor layer which absorbs light emitted from the light-emitting element (light source) and emits blue light. At this time, it is desirable that the light-emitting element which is the light source emit light (ultraviolet light) having a shorter wavelength than that of the blue light.

In the light-converting light-emitting element 30 according to the embodiment, an example of emitting light beams of three colors including red, green, blue has been described. However, the light-converting light-emitting element according to the embodiment is not limited thereto. The light-converting light-emitting element may be a single-color light-emitting element containing only one kind of phosphor layer; or can include multi-color light-emitting elements of white, yellow, magenta, cyan and the like in addition to light-emitting elements of red, green, and blue. In this case, a phosphor layer corresponding to each color may be used. As a result, power consumption can be reduced and color reproduction range can be enlarged. In addition, multi-color phosphor layers can be easily formed by using a photolithography method using a resist, a printing method, or a wet formation method rather than a shadow mask method.

<Light-Converting Light-Emitting Element>

A light-converting light-emitting element according to an embodiment of the invention includes at least one organic layer that includes a light-emitting layer containing the above-described transition metal complex, a layer for multiplying a current, and a pair of electrodes between which the organic layer and the layer for multiplying a current are interposed.

Figure 5:
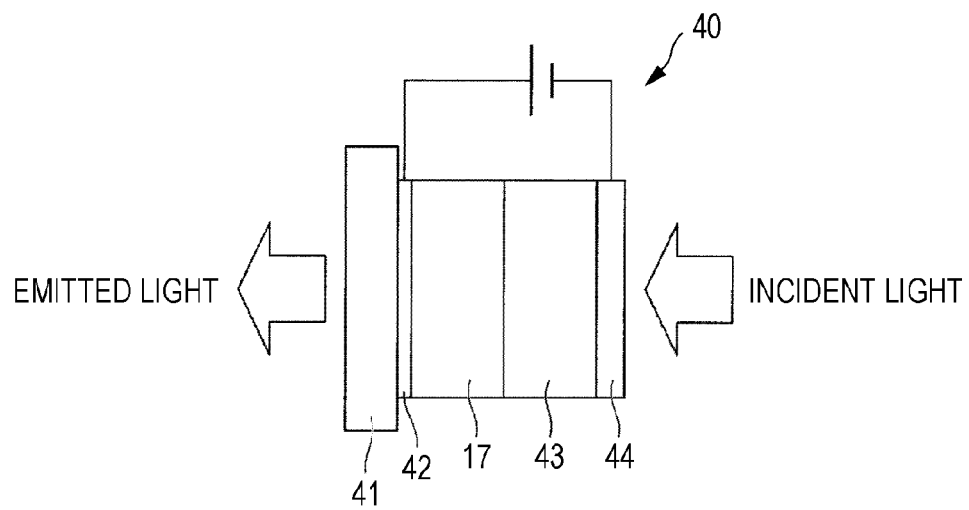
FIG. 5 is a diagram schematically illustrating an embodiment of a light-converting light-emitting element according to the invention.

FIG. 5 is a diagram schematically illustrating an embodiment of the light-converting light-emitting element according to the embodiment. A light-converting light-emitting element 40 illustrated in FIG. 5 converts electrons, obtained using photoelectric conversion due to the photocurrent multiplication effect, into light again according to the principle of EL emission.

In the light-converting light-emitting element 40 illustrated in FIG. 5, a bottom electrode 42 such as an ITO electrode is formed on one surface of an electrode substrate 41 which is formed of a transparent glass substrate. On this bottom electrode 42, an organic EL layer 17, an organic photoelectric material layer 43, and an Au electrode 44 are sequentially laminated. A positive terminal of a drive power supply is connected to the bottom electrode 42, and a negative terminal of the drive power supply is connected to the Au electrode 44.

The organic EL layer 17 can adopt the same configuration as that of the above-described organic EL layer 17 in the organic light-emitting element according to the embodiment.

The organic photoelectric material layer 43 exhibits a photoelectric effect of multiplying a current, and may include only one NTCDA (naphthalene tetracarboxylic dianhydride) layer; or may include plural layers capable of selecting a sensitivity wavelength range. For example, the organic photoelectric material layer 43 may include two layers including a Me-PTC (perylene pigment) layer and a NTCDA layer. The thickness of the organic photoelectric material layer 43 is not particularly limited and is, for example, approximately 10 nm to 100 nm. The organic photoelectric material layer 43 is formed using a vacuum deposition method.

The light-converting light-emitting element 40 according to the embodiment applies a predetermined voltage between the bottom electrode 42 and the Au electrode 44. When the Au electrode 44 is irradiated with light from outside, holes generated by the irradiation of light are trapped and accumulate in the vicinity of the Au electrode 44, which is the negative terminal. As a result, an electric field is concentrated on the interface between the organic photoelectric material layer 43 and the Au electrode 44, electrons are injected from the Au electrode 44, and the current multiplication phenomenon occurs. The organic EL layer 17 emits light based on the current multiplied in this way. Therefore, superior luminescence property can be obtained.

Since the light-converting light-emitting element 40 according to the embodiment includes the organic EL layer 17 containing the above-described transition metal complex, the luminous efficiency can be further improved.

<Organic Laser Diode Light-Emitting Element>

An organic laser diode light-emitting element according to an embodiment of the invention includes a continuous-wave excitation light source; and a resonator structure that is irradiated with light emitted from the continuous-wave excitation light source. In the resonator structure, at least one organic layer that includes a laser-active layer is interposed between a pair of electrodes.

Figure 6:
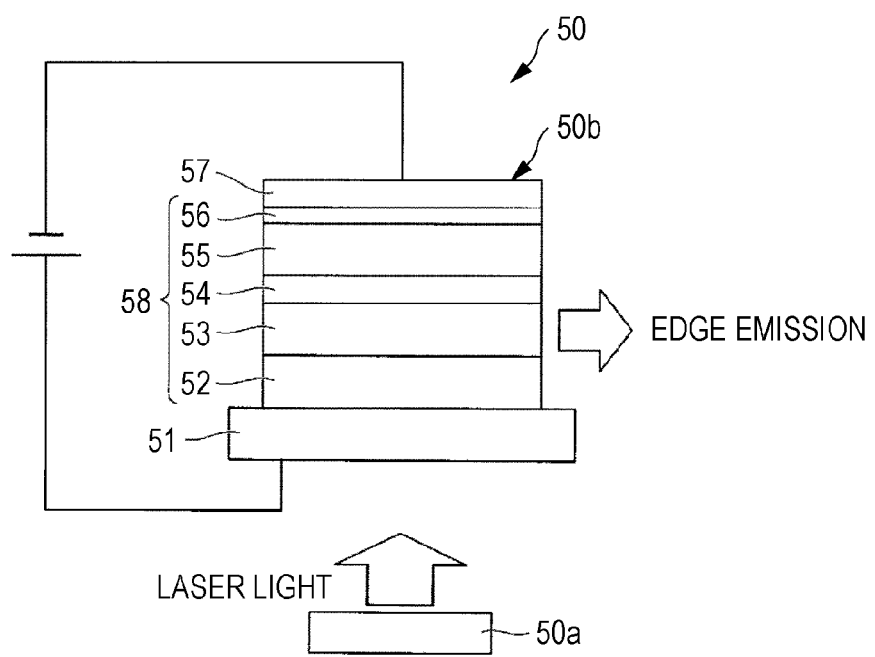
FIG. 6 is a diagram schematically illustrating an embodiment of an organic laser diode light-emitting element according to the invention.

FIG. 6 is a diagram schematically illustrating the organic laser diode light-emitting element according to the embodiment. An organic laser diode light-emitting element 50 illustrated in FIG. 6 includes a continuous-wave excitation light source 50a that emits laser light; and a resonator structure 50b. In the resonator structure 50b, a hole transport layer 52, a laser-active layer 53, a hole blocking layer 54, an electron transport layer 55, an electron injection layer 56, and an electrode 57 are sequentially laminated on an ITO substrate 51. The ITO electrode formed on the ITO substrate 51 is connected to a positive terminal of a drive power supply, and the electrode 57 is connected to a negative terminal of the drive power supply.

The hole transport layer 52, the hole blocking layer, the electron transport layer 55, and the electron injection layer 56 have the same configurations as those of the above-described hole transport layer 13, the hole blocking layer, the electron transport layer 15, and the electron injection layer in the organic light-emitting element according to the aspect of the invention, respectively. The laser-active layer 53 can adopt the same configuration as that of the above-described organic light-emitting layer 14 in the organic light-emitting element according to the aspect of the invention. It is preferable that a host material of the related art be doped with the transition metal complex according to the aspect of the invention as a luminescent material. Alternatively, it is also preferable that the transition metal complex according to the aspect of the invention, which is used as a host material, be doped with a luminescent dopant material of the related art. In FIG. 6, the organic EL layer 58 in which the hole transport layer 52, the laser-active layer 53, the hole blocking layer 54, the electron transport layer 55, and the electron injection layer 56 are sequentially laminated is illustrated. However, the organic laser diode light-emitting element 50 according to the embodiment is not limited thereto and can adopt the same configuration as that of the above-described organic light-emitting layer 14 in the organic light-emitting element according to the aspect of the invention.

In the organic laser diode light-emitting element 50 according to the embodiment, laser light is emitted by the continuous-wave excitation light source 50a from the ITO substrate 51 side which is the anode. As a result, ASE (edge emission) in which the peak luminance is increased corresponding to the excitation intensity of laser light can be produced from a side surface of the resonator structure 50b.

<Dye Laser>

Figure 7:
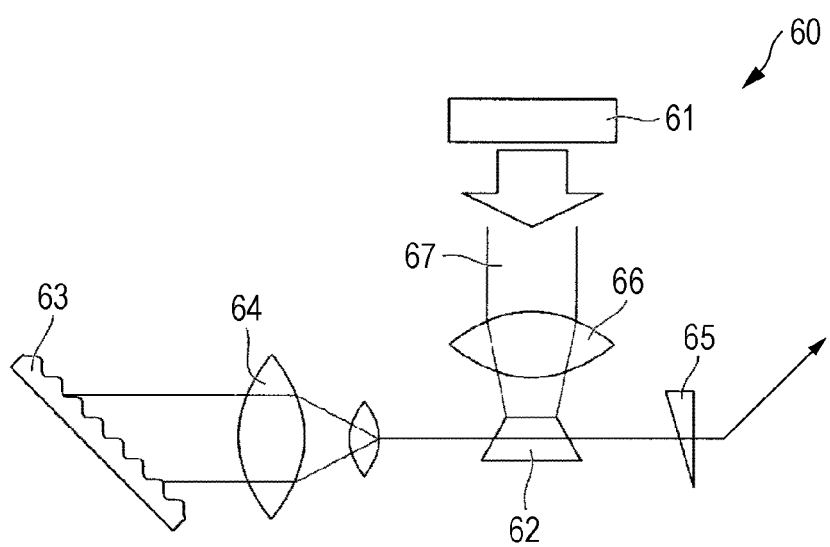
FIG. 7 is a diagram schematically illustrating an embodiment of a dye laser according to the invention.

FIG. 7 is a diagram schematically illustrating an embodiment of a dye laser according to an embodiment of the invention. Briefly, a dye laser 60 illustrated in FIG. 7 includes an excitation light source 61, a lens 66, a partially reflecting mirror 65, a diffraction grating 63, and a beam expander 64. The excitation light source 61 emits pump light 67. The lens 66 collects the pump light 67 to a dye cell 62. The partially reflecting mirror 65 is disposed opposite the beam expander 64 with the dye cell 62 interposed therebetween. The beam expander 64 is disposed between the diffraction grating 63 and the dye cell 62 and collects light from the diffraction grating 63. The dye cell 62 is formed of quartz glass or the like. The dye cell 62 is filled with a laser medium which is a solution containing the transition metal complex according to the aspect of the invention.

In the dye laser 60 according to the embodiment, when the excitation light source 61 emits the pump light 67, the pump light 67 is collected to the dye cell 62 by the lens 66 and excites the transition metal complex according to the aspect of the invention contained in the laser medium of the dye cell 62 to emit light. The light emitted from the luminescent material is discharged outside the dye cell 62 and is reflected and amplified between the partially reflecting mirror 62 and the diffraction grating 63.

The amplified light passes through the partially reflecting mirror 65 and is emitted outside. In this way, the transition metal complex according to the aspect of the invention can also be applied to the dye laser.

The above-described organic light-emitting element, color-converting light-emitting element, and light-converting light-emitting element according to the aspects of the invention can be applied to a display device, an illumination device, and the like.

<Display Device>

A display device according to an embodiment of the invention includes an image signal output portion, a driver, and a light-emitting portion. The image signal output portion outputs an image signal. The driver applies a current or a voltage based on the signal output from the image signal output portion. The light-emitting portion emits light based on the current or the voltage applied from the driver. In the display device according to the embodiment, the light-emitting portion is configured as any one of the above-described organic light-emitting element, color-converting light-emitting element, and light-converting light-emitting element according to the aspects of the invention. In the following description, a case in which the light-emitting porting is the organic light-emitting element according to the aspect of the invention will be described as an example. However, the embodiment is not limited thereto. In the display device according to the embodiment, the light-emitting portion can be configured as the color-converting light-emitting element or the light-converting light-emitting element.

Figure 8:
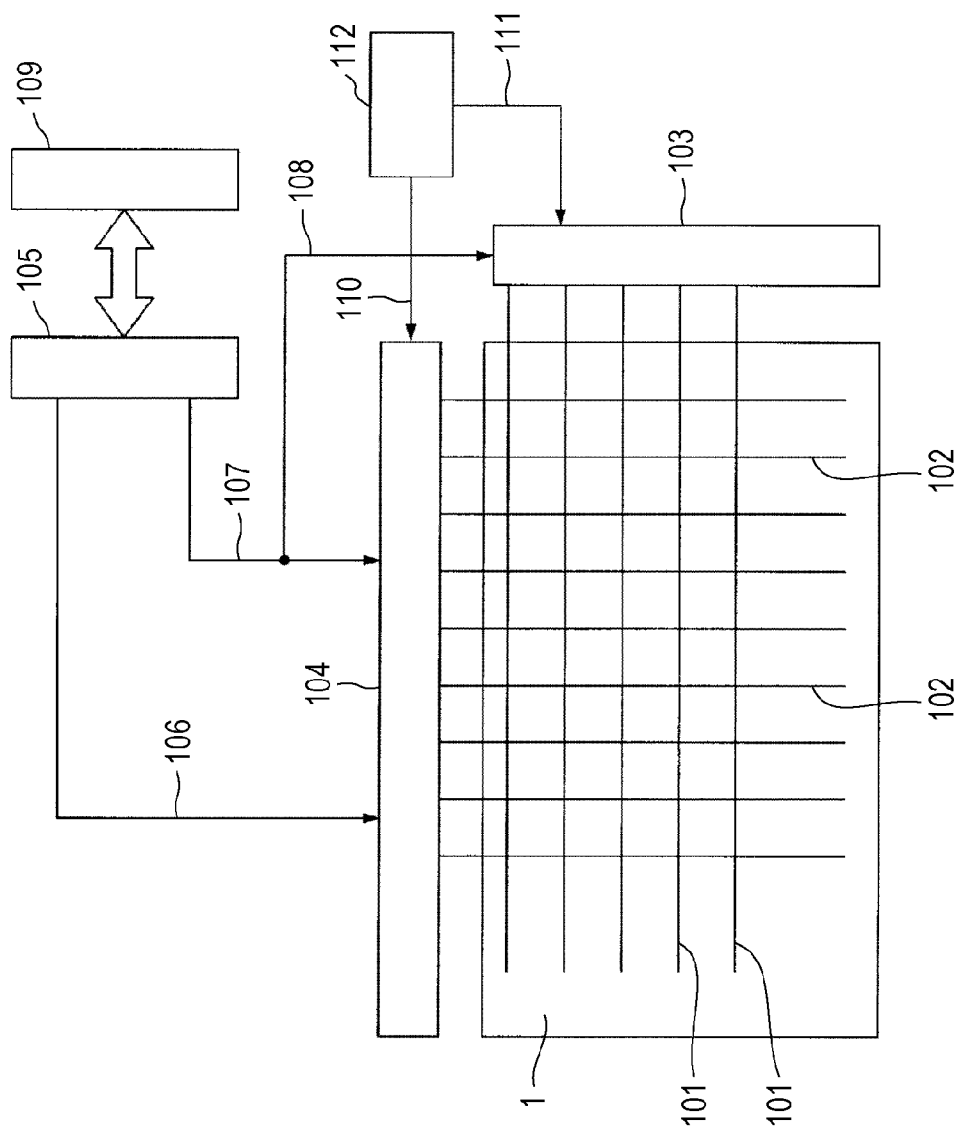
FIG. 8 is a diagram illustrating a configuration example of the connection between an interconnection structure and a drive circuit in a display device according to the invention.
Figure 9:
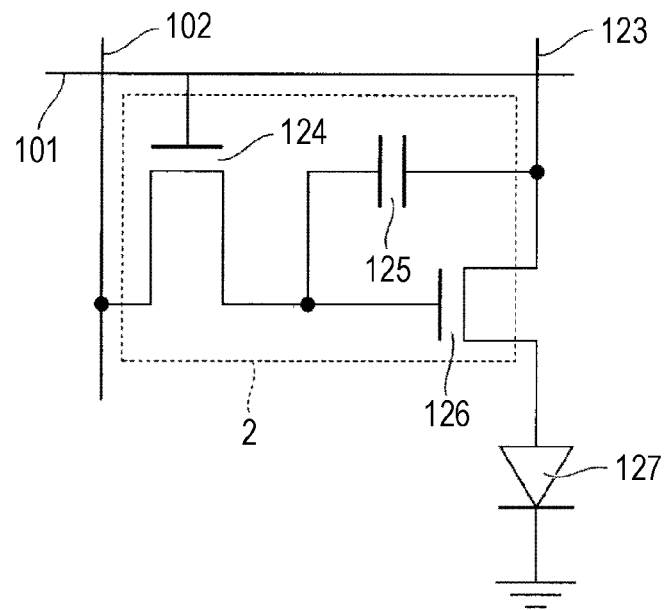
FIG. 9 is a diagram illustrating a circuit constituting one pixel which is arranged in a display device including an organic light-emitting element according to the invention.

FIG. 8 is a diagram illustrating a configuration example of the connection between an interconnection structure and a drive circuit in a display device which includes the above-described organic light-emitting device 20 and a driver. FIG. 9 is a diagram illustrating a circuit constituting one pixel which is arranged in a display device including the organic light-emitting element according to the aspect of the invention.

As illustrated in FIG. 8, in a display device according to the embodiment, scanning lines 101 and signal lines 102 are arranged on the substrate 1 of the organic light-emitting device 20 in a matrix shape when seen in a plan view. The respective scanning lines 101 are connected to a scanning circuit 103 which is provided at one edge of the substrate 1. The respective signal lines 102 are connected to an image signal drive circuit 104 which is provided at another edge of the substrate 1. More specifically, drive elements (TFT circuits 2) such as the thin film transistors of the organic light-emitting device 20 illustrated in FIG. 2 are provided in the vicinity of the respective intersections between the scanning lines 101 and the signal lines 102. The respective drive elements are connected to pixel electrodes. These pixel electrodes correspond to the repellers 11 of the organic light-emitting device 20 having the structure illustrated in FIG. 2, and these repellers 11 correspond to the first electrodes 12.

The scanning circuit 103 and the image signal drive circuit 104 are electrically connected to a controller 105 through control lines 106, 107, and 108. The operation of the controller 105 is controlled by a central processing unit 109. In addition, the scanning circuit 103 and the image signal drive circuit 104 are separately connected to a power circuit 112 through power distribution lines 110 and 111. The image signal output portion includes the CPU 109 and the controller 105.

The driver that drives the organic EL light-emitting portion 10 of the organic light-emitting device 20 includes the scanning circuit 103, the image signal drive circuit 104, and the organic EL power circuit 112. The respective regions which are partitioned by the scanning lines 101 and the signal lines 102 form the TFT circuits 2 of the organic light-emitting device 20 illustrated in FIG. 2.

FIG. 9 is a diagram illustrating a circuit constituting one pixel of the organic light-emitting device 20 which is arranged in one of the regions which are partitioned by the scanning lines 101 and the signal lines 102. In the pixel circuit illustrated in FIG. 9, when a scanning signal is applied to the scanning line 101, this signal is applied to a gate electrode of a switching TFT 124 configured by a thin film transistor and thus the switching TFT 124 is switched on. Next, when an image signal is applied to the signal line 102, this signal is applied to a source electrode of the switching TFT 124 and thus a storage capacitor 125, connected to a drain electrode of the switching TFT 124, is charged through the switching TFT 124 which has been switched on. The storage capacitor 125 is connected between a source electrode and a gate electrode of a driving TFT 126. Accordingly, as a gate voltage of the driving TFT 126 a value is stored which is determined by a voltage of the storage capacitor 125 until the switching TFT 124 is subsequently scanned and selected. A power line 123 is connected to the power circuit (FIG. 8). A current supplied from the power line 123 flows to the organic light-emitting element (organic EL element) 127 through the driving TFT 126 to cause the organic light-emitting element 127 to continuously emit light.

Using the image signal output portion and the driver having such configurations, when a voltage is applied to the organic EL layer (organic layer) 17 which is interposed between the first electrode 12 and the second electrode 16 of a desired pixel, the organic light-emitting element 20 corresponding to the pixel emits light; light in a visible wavelength range can be emitted from the corresponding pixel; and as a result, a desired color or image can be displayed.

In the display device according to the embodiment, the example in which the above-described organic light-emitting element 20 is included as the light-emitting portion has been described. However, the embodiment is not limited thereto. The display device according to the embodiment can suitably include, as the light-emitting portion, any one of the above-described organic light-emitting element, color-converting light-emitting element, and light-converting light-emitting element according to the embodiments.

When the display device according to the embodiment includes, as the light-emitting portion, any one of the above-described organic light-emitting element, color-converting light-emitting element, and light-converting light-emitting element using the transition metal complex according to the embodiment, high luminous efficiency can be obtained.

<Illumination Device>

Figure 10:
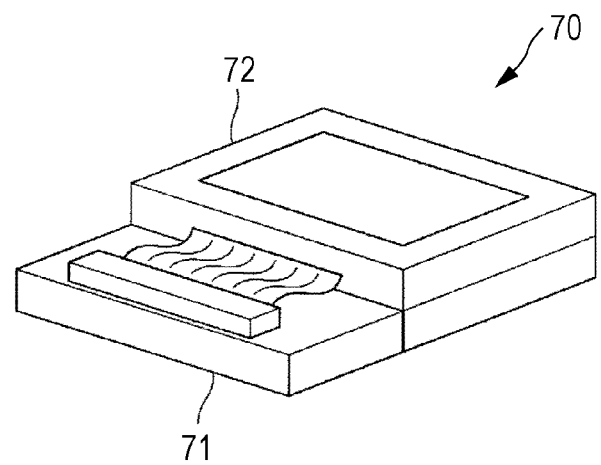
FIG. 10 is a perspective view schematically illustrating a first embodiment of an illumination device according to the invention.

FIG. 10 is a perspective view schematically illustrating an illumination device according to an embodiment of the invention. An illumination device 70 illustrated in FIG. 10 includes a driver 71 that applies a current or a voltage; and a light-emitting portion 72 that emits light based on the current or the voltage applied from the driver 71. In the illumination device according to the embodiment, the light-emitting portion 72 is configured as any one of the above-described organic light-emitting element, color-converting light-emitting element, and light-converting light-emitting element according to the aspects of the invention. In the following description, a case in which the light-emitting portion is the organic light-emitting element 10 according to the aspect of the invention will be described as an example. However, the embodiment is not limited thereto. In the illumination device according to the embodiment, the light-emitting portion can also be configured as the color-converting light-emitting element or the light-converting light-emitting element.

In the illumination device 70 illustrated in FIG. 10, when the driver applies a voltage to the organic EL layer (organic layer) 17 which is interposed between the first electrode 12 and the second electrode 16, the organic light-emitting element 10 corresponding to the pixel emits light and thus blue light can be emitted.

When the organic light-emitting element according to the aspect of the invention is used as the light-emitting portion 72 of the illumination device 70, the organic light-emitting layer of the organic light-emitting element may further contain a well-known organic EL material of the related art in addition to the transition metal complex according to the aspect of the invention.

In the illumination device according to the embodiment, the example in which the above-described organic light-emitting element 10 according to the embodiment is included as the light-emitting portion has been described. However, the embodiment is not limited thereto. The illumination device according to the embodiment can suitably include, as the light-emitting portion, any one of the above-described organic light-emitting element, color-converting light-emitting element, and light-converting light-emitting element according to the embodiments.

When the illumination device according to the embodiment includes, as the light-emitting portion, any one of the above-described organic light-emitting element, color-converting light-emitting element, and light-converting light-emitting element using the transition metal complex according to the aspect of the invention, high luminous efficiency can be obtained.

Figure 11:
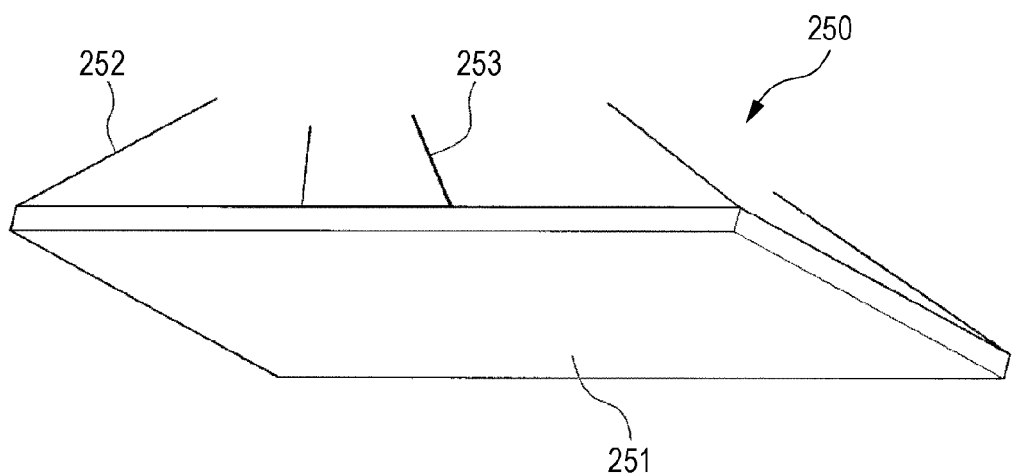
FIG. 11 is a perspective view schematically illustrating another embodiment of the illumination device according to the invention.

The organic light-emitting element, color-converting light-emitting element, and light-converting light-emitting element according to the embodiments can also be applied to, for example, a ceiling light (illumination device) illustrated in FIG. 11.

The ceiling light 250 illustrated in FIG. 11 includes a light-emitting portion 251, a pendent line 252, and a power cord 253. Any one of the organic light-emitting element, color-converting light-emitting element, and light-converting light-emitting element according to the embodiments can be applied to the light-emitting portion 251.

When the illumination device according to the embodiment includes, as the light-emitting portion, any one of the above-described organic light-emitting element, color-converting light-emitting element, and light-converting light-emitting element using the transition metal complex according to the embodiment, high luminous efficiency can be obtained.

Figure 12:
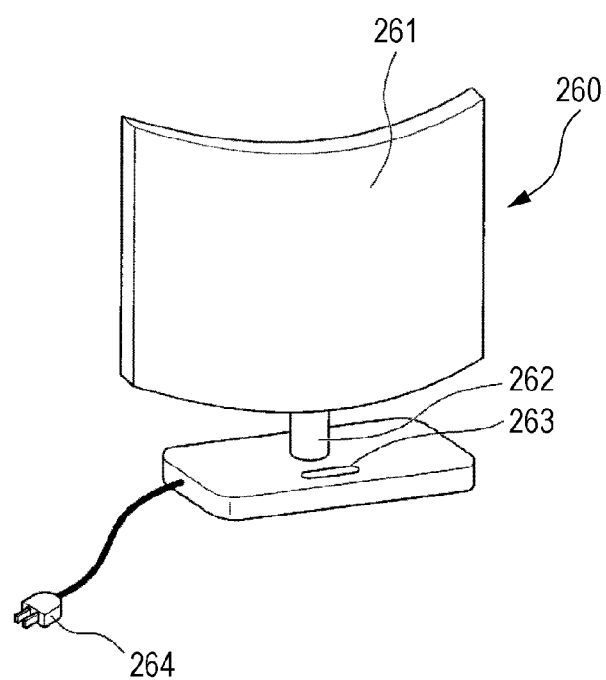
FIG. 12 is a perspective view schematically illustrating another embodiment of the illumination device according to the invention.

Likewise, the organic light-emitting element, color-converting light-emitting element, and light-converting light-emitting element according to the aspects of the invention can be applied to, for example, an illumination stand (illumination device) illustrated in FIG. 12.

The illumination stand 260 illustrated in FIG. 12 includes a light-emitting portion 261, a stand 262, a main switch 263, and a power cord 264. Any one of the organic light-emitting element, color-converting light-emitting element, and light-converting light-emitting element according to the aspects of the invention can be suitably applied to the light-emitting portion 261.

When the illumination device according to the embodiment includes, as the light-emitting portion, any one of the above-described organic light-emitting element, color-converting light-emitting element, and light-converting light-emitting element using the transition metal complex according to the aspect of the invention, high luminous efficiency can be obtained.

<Electronic Equipment>

The above-described display device according to the aspect of the invention can be incorporated into various kinds of electronic equipment.

Hereinafter, electronic equipment including the display device according to the embodiment will be described referring to FIGS. 13 to 16.

Figure 13:
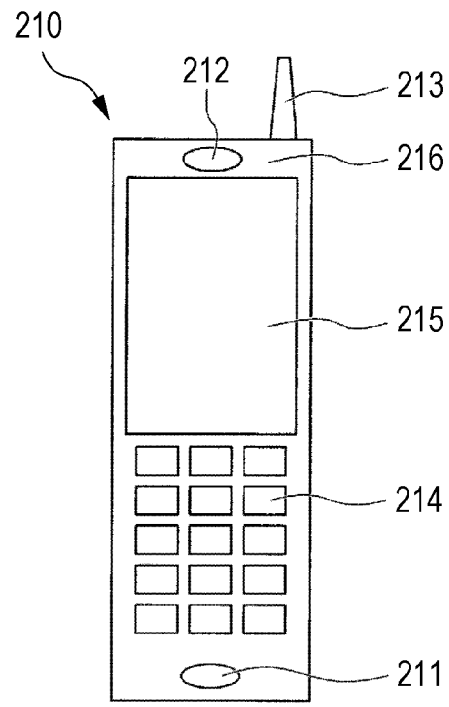
FIG. 13 is a perspective view schematically illustrating an embodiment of electronic equipment according to the invention.

The above-described display device according to the aspect of the invention can be applied to, for example, a mobile phone illustrated in FIG. 13. The mobile phone 210 illustrated in FIG. 13 includes a voice receiver 211, a speaker 212, an antenna 213, a manipulation switch 214, a display 215, and a case 216. The display device according to the aspect of the invention can be suitably applied to the display 215.

When the display device according to the aspect of the invention is applied to the display 215 of the mobile phone 210, an image can be displayed with a higher luminous efficiency.

Figure 14:
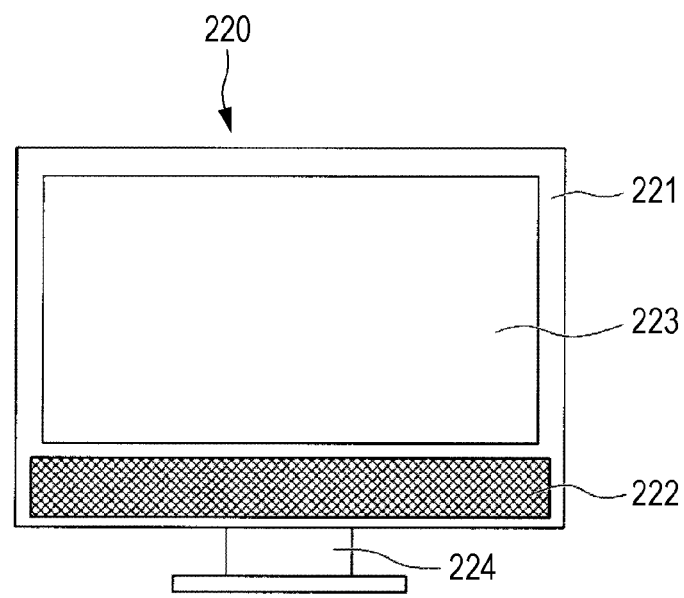
FIG. 14 is a perspective view schematically illustrating an embodiment of electronic equipment according to the invention.

In addition, the above-described display device according to the aspect of the invention can be applied to, for example, a thin-screen TV illustrated in FIG. 14. The thin-screen TV 220 illustrated in FIG. 14 includes a display 221, a speaker 222, a cabinet 223, and a stand 224. The display device according to the aspect of the invention can be suitably applied to the display 221. When the display device according to the aspect of the invention is applied to the display 221 of the thin-screen TV 220, an image can be displayed with a higher luminous efficiency.

Figure 15:
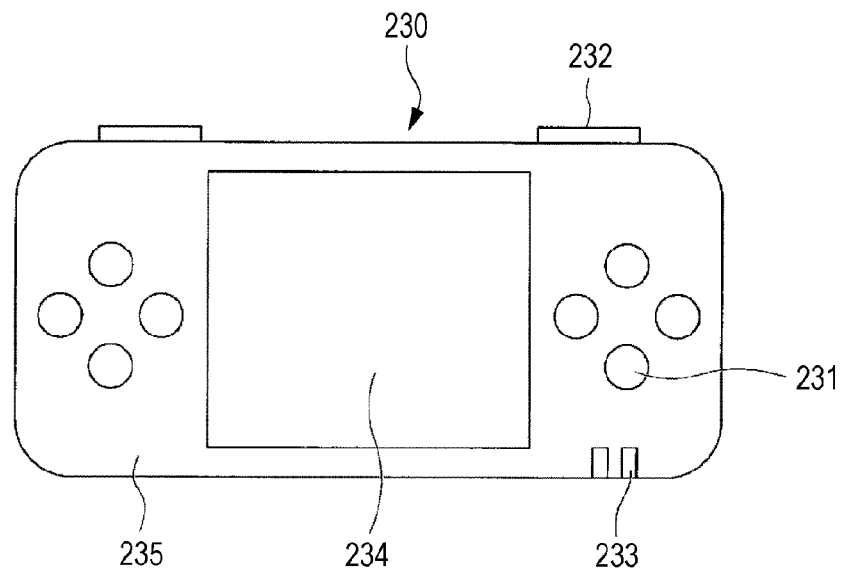
FIG. 15 is a perspective view schematically illustrating an embodiment of electronic equipment according to the invention.

Furthermore, the above-described display device according to the aspect of the invention can be applied to, for example, a portable game machine illustrated in FIG. 15. The portable game machine 230 illustrated in FIG. 15 includes manipulation buttons 231 and 232, an external connection terminal 233, a display 234, and a case 235. The display device according to the aspect of the invention can be suitably applied to the display 234. When the display device according to the aspect of the invention is applied to the display 234 of the portable game machine 230, an image can be displayed with a higher luminous efficiency.

Figure 16:
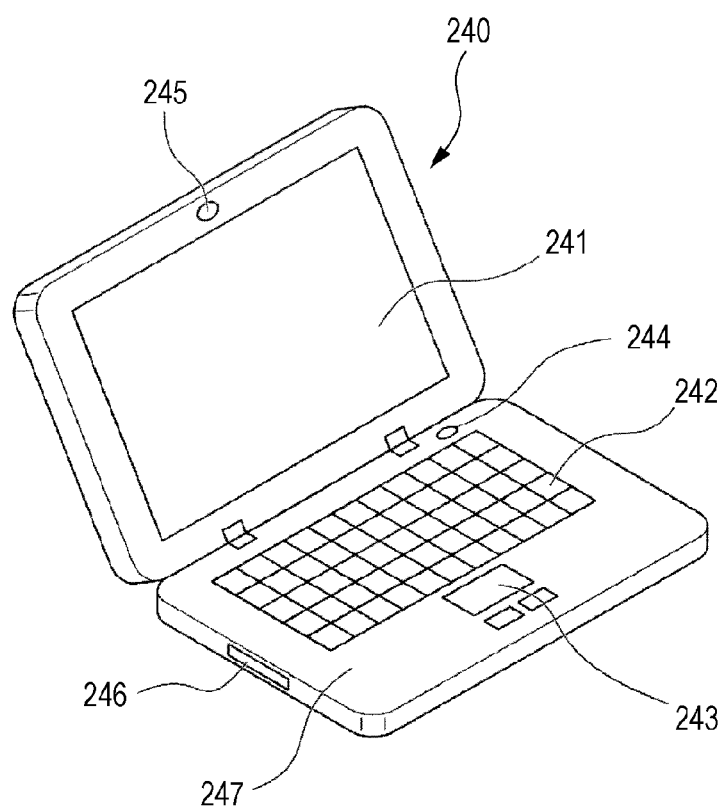
FIG. 16 is a perspective view schematically illustrating an embodiment of electronic equipment according to the invention.

In addition, the above-described display device according to the aspect of the invention can be applied to a laptop computer illustrated in FIG. 16. The laptop computer 240 illustrated in FIG. 16 include a display 241, a keyboard 242, a touch pad 243, a main switch 244, a camera 245, a recording medium slot 246, and a case 247. The display device according to the aspect of the invention can be suitably applied to the display 241 of the laptop computer 240. When the display device according to the aspect of the invention is applied to the display 241 of the laptop computer 240, an image can be displayed with a higher luminous efficiency.

Hereinabove, preferable examples according to the aspects of the invention have been described referring to the accompanying drawings, but it is needless to say that the aspects of the invention are not limited to the examples. The shapes and combinations of the respective components illustrated in the above-described examples are merely examples and can be modified in various ways within a range not departing from the scope of the invention based on the design requirements.

For example, in the display device described in the embodiment, it is preferable that a polarizer be provided on a light extraction surface. As the polarizer, a well-known linear polarizer and a well-known λ/4 polarizer of the related art can be used in combination. Here, by providing such a polarizer, outside light reflection from the electrodes of the display device; or outside light reflection from a surface of the substrate or the sealing substrate can be prevented; and the contrast of the display device can be improved. In addition, the specific description relating to the shapes, numbers, arrangements, materials, formation methods, and the like of the respective components of the phosphor substrate, the display device, and the illumination device are not limited to the above-described embodiments and can be appropriately modified.

EXAMPLES

Hereinafter, the aspects of the invention will be described in detail based on examples but is not limited to these examples.

Compounds used in the examples are as follows.

[Chem. 63]

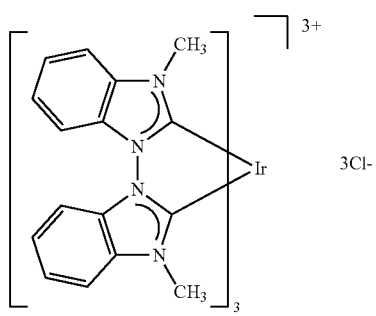

Compound 1

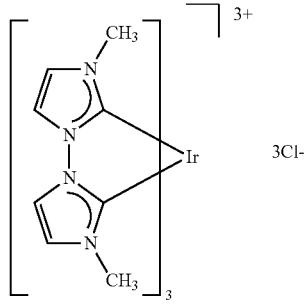

Compound 2

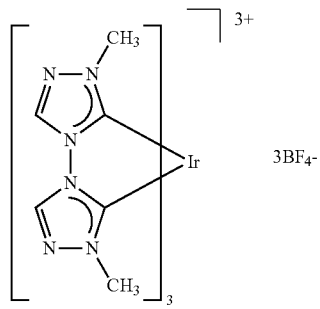

Compound 3

[Synthesis of Transition Metal Complex]

In the following synthesis examples, compounds in the respective steps and a final compound (transition metal complex) were identified using MS spectrum (FAB-MS).

Synthesis Example 1

Synthesis of Compound 1

Compound 1 was synthesized according to the following route.

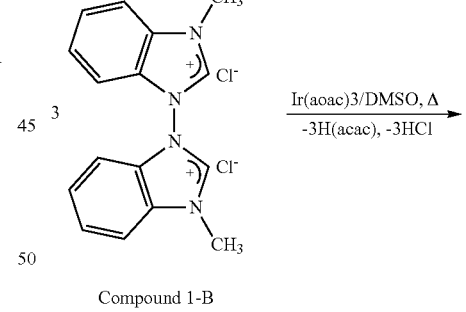

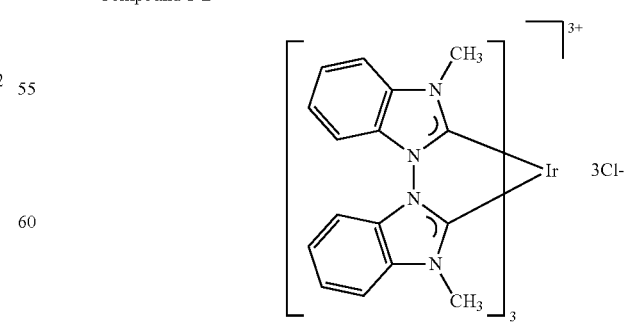

Synthesis of Compound 1-B

1-Methyl-imidazole (Compound 1-A; 0.156 mol) was dissolved in 20 ml of THF (tetrahydrofuran) to obtain a solution. Dimethyldichlorosilane (Me$_2$SiCl$_2$) was added to the solution, followed by stirring at room temperature for 1 hour. Then, the solvent was removed from the reaction solution under reduced pressure. The residue was washed with 30 mL of hexane and the solid material was separated by filtration in a liquid separating treatment, followed by drying. As a result, Compound 1-B was obtained. Yield: 86%

Synthesis of Compound 1

Iridium (III) acetyl acetate (Ir(acac)$_3$; 0.5 mmol) was put into dimethylsulfoxide (DMSO; 3 mL), followed by heating at 100° C. The DMSO solution (20 mL) of Compound 1-B (2.0 mmol) was added dropwise to the resultant solution over 12 hours. Then, the solution was stirred at 100° C. for 2 hours, and the solvent was removed from the reaction solution under reduced pressure at 70° C. The extracted solid material was washed with tetrahydrofuran (THF) twice, followed by drying under reduced pressure. As a result, Compound 1 was obtained. Yield: 25%, FAB-MS (+): m/z 1071.2[M-Cl]$^+$, 1036.3[M-2Cl]$^+$, 1001.3[M-3Cl]$^+$, 500.6 [M-3Cl]$^{2+}$.

Synthesis Example 2

Synthesis of Compound 2

Compound 2 was synthesized according to the following route.

[Chem. 65]

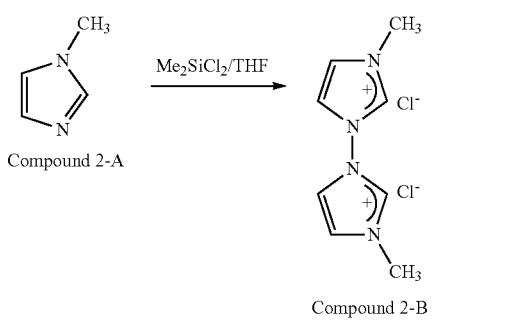

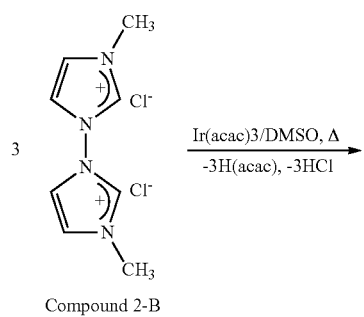

Compound 2-B

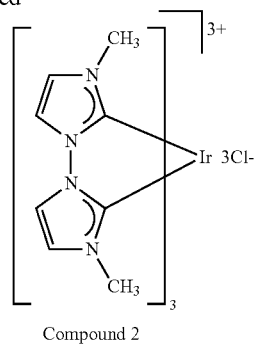

Compound 2

Synthesis of Compound 2-B

1-Methyl-imidazole (Compound 2-A; 0.156 mol) was dissolved in 20 ml of THF (tetrahydrofuran) to obtain a solution. Dimethyldichlorosilane (Me$_2$SiCl$_2$) was added to the solution, followed by stirring at room temperature for 1 hour. Then, the solvent was removed from the reaction solution under reduced pressure. The residue was washed with 30 mL of hexane and the solid material was separated by filtration in a liquid separating treatment, followed by drying. As a result, Compound 1-B was obtained. Yield: 86%

Synthesis of Compound 2

Iridium (III) acetyl acetate (Ir(acac)$_3$; 0.5 mmol) was put into dimethylsulfoxide (DMSO; 3 mL), followed by heating at 100° C. The DMSO solution (20 mL) of Compound 1-B (2.0 mmol) was added dropwise to the resultant solution over 12 hours. Then, the solution was stirred at 100° C. for 2 hours, and the solvent was removed from the reaction solution under reduced pressure at 70° C. The extracted solid material was washed with tetrahydrofuran (THF) twice, followed by drying under reduced pressure. As a result, Compound 2 was obtained. Yield: 35%, FAB-MS (+): m/z 749.2[M-Cl]%, 714.2[M-2Cl]%, 679.2[M-3Cl]%, 339.6[M-3Cl]$^{2+}$.

Synthesis Example 3

Synthesis of Compound 3

Compound 3 was synthesized according to the following route.

[Chem. 66]

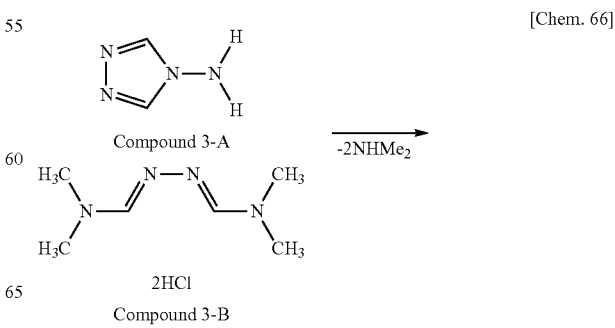

-continued

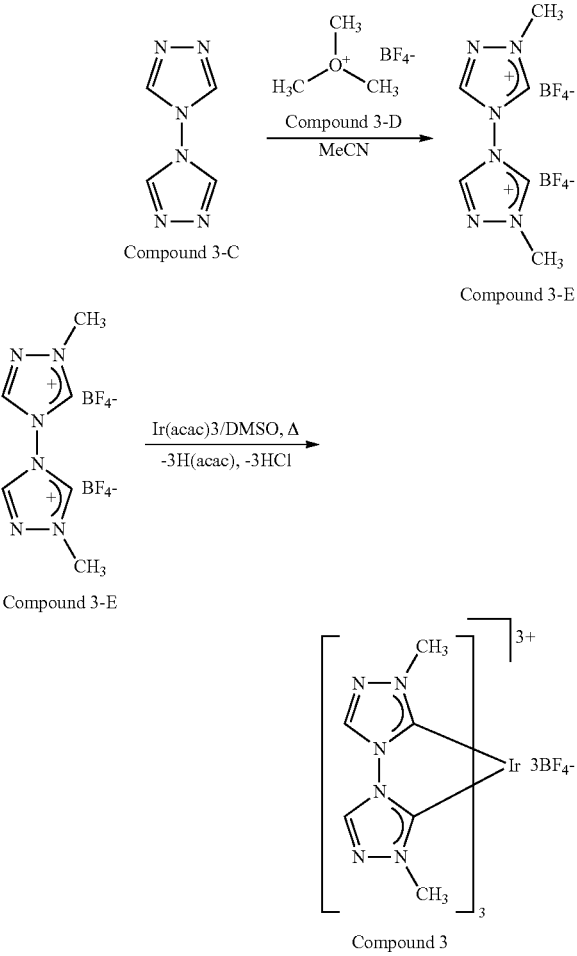

Synthesis of Compound 3-C 4-amino-1,2,4-triazole (Compound 3-A; 0.1 mol), N,N'-Bis(dimethylaminomethylene)hydrazine dihydrochloride (Compound 3-B; 0.1 mol), and p-toluenesulfonic acid (0.8 g) was heated to reflux in toluene (50 ml) for 80 hours. Next, after adding dimethylamine (0.086 mol) to the reaction solution, the reaction solution was filtered. The obtained solid material was washed with ethanol, followed by drying in a vacuum. As a result, Compound 3-C was obtained.

Synthesis of Compound 3-E 4,4'-bi-1,2,4-triazole (Compound 3-C, 2.2 mol) and trimethyloxonium tetrafluoroborate (4.85 mol) were added to 10 mL of acetonitrile (MeCN) to obtain a mixed solution. After heating this mixed solution to reflux for 12 hours, the reactant was filtered. The resultant was washed with dichloromethane ($CH_2Cl_2$), followed by drying in a vacuum. As a result, Compound 3-E was obtained.
Yield: 85%

Synthesis of Compound 3

Compound 3 was synthesized using the same equivalent relationships and reaction temperature as those of Compound 1. Yield: 45%, FAB-MS (+): m/z 859.2[M-$BF_4$]$^+$, 772.2[M-2$BF_4$]$^+$, 685.2[M-3$BF_4$]$^+$, 342.6[M-3$BF_4$]$^{2+}$.

[Energy Measurement of T1 Level]

Regarding Compound 1 to 3, an emission spectrum was measured using a fluorescence spectrophotometer (QE-1100, manufactured by Otsuka Electronics Co., Ltd.). The T1 level energy was measured from a peak wavelength in a short wavelength range of the measured emission spectrum. The measurement results are shown in Table 1. In addition, regarding a luminescent material, iridium (III) tris(1-phenyl-3-methylbenzimidazolin-2-ylidene-C,C2') which is a well-known material of the related art and (Ir(Pmb)$_3$); and 4 4'-N,N'-bis(carbazole)biphenyl (CBP) which is a host material, the T1 level energy was measured, and the results thereof are also shown in Table 1.

TABLE 1

|  | T1 Level Energy |
| --- | --- |
| Compound 1 | 3.2 eV |
| Compound 2 | 3.7 eV |
| Compound 3 | 4.2 eV |
| Ir(Pmb)$_3$ (Luminescent Material) | 3.2 eV |
| CBP (Host Material) | 2.6 eV |

As shown in Table 1, Compound 1 to 3 which were the transition metal complexes according to the aspect of the invention had a T1 level higher than or equal to that of the luminescent material of the related art. In addition, it was confirmed that Compound 1 to 3 had a T1 level higher than or equal to that of the host material of the related art.

[Preparation of Organic Light-Emitting Element and Evaluation of Organic EL Characteristics]

Example 1

Indium tin oxide (ITO) was formed as an anode on a glass substrate. A single layer of polyimide-based resin was patterned so as to surround the ITO electrode. Then, a substrate on which the ITO electrode was formed was washed with ultrasonic waves, followed by baking at 200° C. under reduced pressure for 3 hours.

Next, an aqueous solution of poly(3,4-ethylenedioxythiophene):poly(styrenesulfonate) (PEDOT:PSS) was coated on the anode using a spin coating method. As a result, a hole injection layer having a thickness of 45 nm was formed on the anode. Next, the resultant was dried using a hot plate at 200° C. for 30 minutes.

Next, CFL (4,4'-bis(N-carbazolyl)-9,9'-spirobifluorene; T1 level: 3.4 eV) and Compound 1 (T1 level: 3.2 eV) were dissolved in dichloroethane to obtain a solution. This solution was coated on the hole injection layer using a spin coating method. As a result, an organic light-emitting layer was formed. At this time, CFL which was the host material was doped with Compound 1 such that the content of Compound 1 in CFL was approximately 7.5%. Next, a UGH2 (1,4-bis(triphenylsilyl)benzene) film having a thickness of 5 nm was formed on the organic light-emitting layer as a hole blocking layer. Further, 1,3,5-tris(N-phenylbenzimidazol-2-yl)benzene (TPBI) was deposited on the hole blocking layer using a vacuum deposition method. As a result, an electron transport layer having a thickness of 30 nm was formed on the hole blocking layer.

Next, lithium fluoride (LiF) was deposited on the electron transport layer using a vacuum deposition method at a deposition rate of 1 angstrom/sec. As a result, a LiF film having a thickness of 0.5 nm was formed. Then, an aluminum (Al) film having a thickness of 100 nm was formed on the LiF film. In this way, a laminated film of LiF and Al was formed as a cathode. As a result, an organic EL element (organic light-emitting element) was prepared.

The current efficiency (luminous efficiency) and emission wavelength of the obtained organic EL element at 1000 cd/m² were measured. The results are also shown in Table 2. Ultraviolet emission was realized with a satisfactory efficiency.

Comparative Example 1

An organic EL element (organic light-emitting element) was prepared using the same preparation method as that of Example 1, except that the dopant (luminescent material) with which the organic light-emitting layer was doped was changed to a material (Ir(dpbic)$_3$; T1 level: 3.2 eV) of the related art; and the host material was changed to CBP (T1 level: 2.6 eV). The current efficiency (luminous efficiency) and emission wavelength of the obtained organic EL element at 1000 cd/m² were measured. The results are also shown in Table 2.

Comparative Example 2

An organic EL element (organic light-emitting element) was prepared using the same preparation method as that of Example 1, except that the dopant (luminescent material) with which the organic light-emitting layer was doped was changed to a material (Ir(dpbic)$_3$; T1 level: 3.2 eV) of the related art. The current efficiency (luminous efficiency) and emission wavelength of the obtained organic EL element at 1000 cd/m² were measured. The results are also shown in Table 2.

Example 2

An organic EL element (organic light-emitting element) was prepared using the same preparation method as that of Example 1, except that the dopant (luminescent material) with which the organic light-emitting layer was doped was changed to a material tris(1-phenyl-3-methylbenzimidazolin-2-ylidene iridium (III) (Ir(dpbic)$_3$)) of the related art; and Compound 2 (T1 level: 3.7 eV) was used instead of CBP as the host material. The current efficiency (luminous efficiency) and emission wavelength of the obtained organic EL element at 1000 cd/m² were measured. The results are also shown in Table 2.

Example 3

An organic EL element (organic light-emitting element) was prepared using the same preparation method as that of Example 1, except that the dopant (luminescent material) with which the organic light-emitting layer was doped was changed to a material (Ir(dpbic)$_3$) of the related art; and Compound 3 (T1 level: 4.2 eV) was used instead of CBP as the host material. The emission wavelength of the obtained organic EL element at 1000 cd/m² were measured. The results are also shown in Table 2.

Example 4

An organic EL element (organic light-emitting element) was prepared using the same preparation method as that of Example 2, except that an exciton blocking layer is formed between the hole injection layer and the organic light-emitting layer by coating a solution in which Compound 3 (T1 level: 4.2 eV) was dissolved in dichloromethane thereon using a spin coating method. The emission wavelengths of the obtained organic EL elements at 1000 cd/m² were measured. The results are also shown in Table 2.

TABLE 2

| | Host | Dopant (Luminescent Material) | Luminescent Efficiency (cd/A) | Maximum Emission Position (nm) |
|---|---|---|---|---|
| Example 1 | CFL | Compound 1 | 2.2 | 385 |
| Example 2 | Compound 2 | Ir(dpbic)$_3$ | 2.8 | 389 |
| Example 3 | Compound 3 | Ir(dpbic)$_3$ | 3.5 | 389 |
| Example 4 | Compound 2 | Ir(dpbic)$_3$ | 4.0 | 389 |
| Comparative Example 1 | CBP | Ir(dpbic)$_3$ | No Emission | |
| Comparative Example 2 | CFL | Ir(dpbic)$_3$ | 1.2 | 390 |

It can be seen from the results of Table 2 that the organic EL element of Example 1 in which Compound 1, which was the transition metal complex according to the aspect of the invention, was used as a dopant (luminescent material) showed more satisfactory deep blue emission than that of the organic EL element of Comparative Example 2 in which the related-art compound (Ir(dpbic)$_3$) was used as a luminescent material. In addition, the organic EL elements of Examples 2 and 3 in which Compounds 2 and 3, which were the transition metal complexes according to the aspect of the invention, were used as a host material showed more satisfactory blue emission than that of the organic EL element of Comparative Example 1 in which the related-art compound CBP was used as a host material. Further, in Example 4 in which, in addition to the element configuration of Example 2, the exciton blocking layer was formed between the hole injection layer and the organic light-emitting layer by using Compound 3 as an exciton blocking material, the luminous efficiency is higher than that of the element of Example 2.

[Preparation of Color-Converting Light-Emitting Element]

Example 5

In this example, using the organic ultraviolet to blue light-emitting elements (organic EL elements) containing the transition metal complexes according to the aspect of the invention, a color-converting light-emitting element which converted light emitted from the organic light-emitting element into red light and a color-converting light-emitting element which converted light emitted from the organic light-emitting element into green light were prepared, respectively.

(Formation of Organic EL Substrate)

A silver film having a thickness of 100 nm was formed on a glass substrate having a thickness of 0.7 mm using a sputtering method to form a repeller. An indium-tin oxide (ITO) film having a thickness of 20 nm was formed on the silver film using a sputtering method to form a repeller (anode) as a first electrode. Then, the first electrode was patterned using a well-known photolithography method so as to have 90 stripe patterns having a width of 2 mm.

Next, a SiO$_2$ layer having a thickness of 200 nm was laminated on the first electrode (repeller) using a sputtering method and then was patterned using a well-known photolithography method so as to cover edge portions of the first electrode (repeller). As a result, an edge cover was formed. The edge cover had a structure in which short sides of the repeller were covered with SiO$_2$ by 10 μm from the edges. The resultant was washed with water, followed by washing with pure water and ultrasonic waves for 10 minutes, washing with acetone and ultrasonic waves for 10 minutes, washing with isopropyl alcohol steam for 5 minutes, and drying at 100° C. for 1 hour.

Next, an aqueous solution of poly(3,4-ethylenedioxythiophene):poly(styrenesulfonate) (PEDOT:PSS) was coated on the first electrode using a spin coating method. As a result, a hole injection layer having a thickness of 45 nm was formed on the first electrode. Next, the resultant was dried using a hot plate at 200° C. for 30 minutes.

Next, CFL (4,4'-bis(N-carbazolyl)-9,9'-spirobifluorene; T1 level: 3.4 eV) and Compound 1 (T1 level: 3.2 eV) were dissolved in dichloroethane to obtain a solution. This solution was coated on the hole injection layer using a spin coating method. As a result, a blue light-emitting layer was formed. At this time, CFL which was the host material was doped with Compound 1 such that the content of Compound 1 in CFL was approximately 7.5%.

Next, the dried substrate was fixed to a substrate holder in an inline type resistance heating deposition device. The pressure was reduced to a vacuum of $1\times10^{-4}$ Pa or lower, and respective organic layers of the organic EL layer were formed. CFL (4,4'-bis(N-carbazolyl)-9,9'-spirobifluorene; T1 level: 3.4 eV) and Compound 1 (T1 level: 3.2 eV) were dissolved in dichloroethane to obtain a solution. This solution was coated on the hole injection layer using a spin coating method. As a result, an organic light-emitting layer was formed. At this time, CFL which was the host material was doped with Compound 1 such that the content of Compound 1 in CFL was approximately 7.5%.

Next, a hole blocking layer (thickness: 10 nm) was formed on the organic light-emitting layer using 2,9-dimethyl-4,7-diphenyl-1,10-phenanthroline (BCP)

Next, an electron transport layer (thickness: 30 nm) was formed on the hole blocking layer using tris(8-hydroxyquinoline)aluminum (Alq3).

Next, an electron injection layer (thickness: 0.5 nm) was formed on the electron transport layer using lithium fluoride (LiF).

Through the above-described processes, the respective organic layers of the organic EL layer were formed.

Next, a semitransparent electrode was formed on the electron injection layer as a second electrode. In order to form the second electrode, first, the substrate on which the electron injection layer was formed in the above-described process was fixed to a metal deposition chamber. Then, a shadow mask for forming the semitransparent electrode (second electrode) and the substrate were aligned. As the shadow mask, a mask having openings is used so as to form the semitransparent electrodes (second electrodes) in a stripe shape having a width of 2 mm in a direction opposite the repellers (first electrodes) in a stripe shape. Next, magnesium and silver were codeposited on a surface of the electron injection layer of the organic EL layer using a vacuum deposition method at deposition rates of 0.1 angstrom/sec and 0.9 angstrom/sec to form desired patterns of magnesium and silver (thickness: 1 nm). Furthermore, a desired pattern of silver (thickness: 19 nm) was formed thereon at a deposition rate of 1 angstrom/sec in order to enhance the interference effect and to prevent voltage drop due to interconnection resistance in the second electrode. Through the above-described processes, the semitransparent electrode (second electrode) was formed. Here, the microcavity effect (interference effect) was exhibited between the repeller (first electrode) and the semitransparent electrode (second electrode), which can improve the luminance on the front side.

Through the above-described processes, the organic EL substrate on which the organic EL portion is formed is prepared.

(Formation of Phosphor Substrate)

Next, a red phosphor layer was formed on a glass substrate equipped with a red color filter having a thickness of 0.7 mm, and a green phosphor layer was formed on a glass substrate equipped with a green color filter having a thickness of 0.7 mm.

The red phosphor layer was formed according to the following order. First, 15 g of ethanol and 0.22 g of γ-glycidoxypropyl triethoxysilane were added to 0.16 g of aerosol having an average particle size of 5 nm, followed by stirring for 1 hour at room temperature in open system. This mixture and 20 g of red phosphor material (pigment) $K_5Eu_{2.5}(WO_4)_{6.25}$ were put into a mortar and pounded, followed by heating with an oven at 70° C. for 2 hours and heating with an oven at 120° C. for 2 hours. As a result, a surface-reformed $K_5Eu_{2.5}(WO_4)_{6.25}$ was obtained. Next, 30 g of polyvinyl alcohol in which a mixed solution (300 g; water/dimethylsulfoxide=1/1) was dissolved was added to 10 g of the surface-reformed $K_5Eu_{2.5}(WO_4)_{6.25}$, followed by stirring with a disperser. As a result, a red phosphor layer-forming coating solution was prepared. The red phosphor layer-forming coating solution was coated at a red pixel position on a CF-equipped glass substrate using a screen printing method so as to have a width of 3 mm. Next, the resultant was heated and dried with a vacuum oven (under conditions of 200° C. and 10 mmHg) for 4 hours. As a result, a red phosphor layer having a thickness of 90 μm was formed.

The green phosphor layer was formed according to the following order. First, 15 g of ethanol and 0.22 g of γ-glycidoxypropyl triethoxysilane were added to 0.16 g of aerosol having an average particle size of 5 nm, followed by stirring for 1 hour at room temperature in open system. This mixture and 20 g of green phosphor material (pigment) $Ba_2SiO_4:Eu^{2+}$ were put into a mortar and pounded, followed by heating with an oven at 70° C. for 2 hours and heating with an oven at 120° C. for 2 hours. As a result, a surface-reformed $Ba_2SiO_4:Eu^{2+}$ was obtained. Next, 30 g of polyvinyl alcohol (resin) in which a mixed solution (300 g, solvent; water/dimethylsulfoxide=1/1) was dissolved was added to 10 g of the surface-reformed $Ba_2SiO_4:Eu^{2+}$, followed by stirring with a disperser. As a result, a green phosphor layer-forming coating solution was prepared. The green phosphor layer-forming coating solution was coated at a green pixel position on a CF-equipped glass substrate using a screen printing method so as to have a width of 3 mm.

Next, the resultant was heated and dried with a vacuum oven (under conditions of 200° C. and 10 mmHg) for 4 hours. As a result, a green phosphor layer having a thickness of 60 μm was formed.

Through the above-described processes, a phosphor substrate on which the red phosphor layer was formed and a phosphor substrate on which the green phosphor layer was formed were prepared, respectively.

(Assembly of Color-Converting Light-Emitting Elements)

Regarding the color-converting red light-emitting element and the color-converting green light-emitting element, the organic EL substrate and each of the phosphor substrates prepared as described above were aligned according to alignment markers which were formed outside a pixel arrangement position. Each of the phosphor substrates were coated with a thermosetting resin before the alignment.

After the alignment, both substrates were bonded to each other through the thermosetting resin, followed heating at 90° C. for 2 hours to perform curing. The bonding process of both substrates were performed in a dry air environment (water content: −80° C.) in order to prevent the organic EL layer from deteriorating due to water.

A peripheral terminal of each of the obtained color-converting light-emitting elements was connected to an external power supply. As a result, superior green light emission and red light emission were obtained.

[Preparation of Display Device]

Example 6

A silicon semiconductor film was formed on a glass substrate with a plasma chemical vapor deposition (plasma CVD) method, followed by crystallization. As a result, a polycrystalline semiconductor film (polycrystalline silicon thin film) was formed. Next, the polycrystalline silicon thin film was etched to form plural island-shaped patterns. Next, silicon nitride (SiN) was formed on each island structure of the polycrystalline silicon thin film as a gate insulating film. Next, a laminated film of titanium (Ti)-aluminum (Al)-titanium (Ti) was sequentially formed as a gate electrode, followed by etching and patterning. A source electrode and a drain electrode were formed on the gate electrode using Ti—Al—Ti to prepare plural thin film transistors (TFT).

Next, an interlayer dielectric having a through-hole was formed on each of the formed thin film transistors, followed by planarizing. Then, indium tin oxide (ITO) was formed as an anode through the through-hole. A single layer of polyimide-based resin was patterned so as to surround the ITO electrode. Then, a substrate on which the ITO electrode was formed was washed with ultrasonic waves, followed by baking at 200° C. under reduced pressure for 3 hours.

Next, an aqueous solution of poly(3,4-ethylenedioxythiophene):poly(styrenesulfonate) (PEDOT:PSS) was coated on the anode using a spin coating method. As a result, a hole injection layer having a thickness of 45 nm was formed on the anode. Next, the resultant was dried using a hot plate at 200° C. for 30 minutes.

Next, CFL (4,4'-bis(N-carbazolyl)-9,9'-spirobifluorene; T1 level: 3.4 eV) and Compound 1 (T1 level: 3.2 eV) were dissolved in dichloroethane to obtain a solution. This solution was coated on the hole injection layer using a spin coating method. As a result, an organic light-emitting layer was formed. At this time, CFL which was the host material was doped with Compound 1 such that the content of Compound 1 in CFL was approximately 7.5%. Next, a UGH2 (1,4-bis(triphenylsilyl)benzene) film having a thickness of 5 nm was formed on the organic light-emitting layer as a hole blocking layer. Further, 1,3,5-tris(N-phenylbenzimidazol-2-yl)benzene (TPBI) was deposited on the hole blocking layer using a vacuum deposition method. As a result, an electron transport layer having a thickness of 30 nm was formed on the hole blocking layer.

Next, lithium fluoride (LiF) was deposited on the electron transport layer using a vacuum deposition method at a deposition rate of 1 angstrom/sec. As a result, a LiF film having a thickness of 0.5 nm was formed. Then, an aluminum (Al) film having a thickness of 100 nm was formed on the LiF film. In this way, a laminated film of LiF and Al was formed as a cathode. As a result, an organic EL element (organic light-emitting element) was prepared.

Display devices in which the above-described organic light-emitting elements (organic EL elements) were respectively arranged in a 100×100 matrix shape were prepared, and a moving image was displayed thereon. Each of the display devices includes an image signal output portion that outputs an image signal; a driver that includes a scanning electrode drive circuit and a signal drive circuit which output the image signal from the image signal output portion; and a light-emitting portion that includes organic light-emitting elements (organic EL element) which are arranged in a 100×100 matrix shape. In all the display devices, an image having a high color purity was obtained. In addition, even when plural display devices were prepared, there were no variations between the devices and the in-plane uniformity was superior.

[Preparation of Illumination Device]

Example 7

An illumination device including a driver that applies a current; and a light emitting portion that emits light based on the current applied from the driver was prepared. In this example, organic light-emitting elements (organic EL elements) were respectively prepared with the same preparation methods as those of Examples 1 to 3, except that the organic light-emitting elements (organic EL elements) were formed on a film substrate. Each of the organic light-emitting elements was used as the light-emitting portion. When a voltage is applied to this organic light-emitting device for lighting, a surface-emitting illumination device having a uniform lighting surface was obtained without using indirect illumination resulting in luminance loss. In addition, the prepared illumination device can be used as a backlight of a liquid crystal display panel.

[Preparation of Light-Converting Light-Emitting Element]

Example 8

The light-converting light-emitting element illustrated in FIG. 5 was prepared.

The light-converting light-emitting element was prepared according to the following order. First, the same processes as those of Example 1 were performed until the electron transport layer formation. Then, a NTCDA (naphthalene tetracarboxylic dianhydride) layer having a thickness of 500 nm was obtained on the electron transport layer as a photoelectric material layer. Next, an Au thin film having a thickness of 20 nm was formed on the NTCDA layer to form an Au electrode. Here, a part of the Au electrode was led out to an end of the element substrate through a desired pattern interconnection, which was integrally formed of the same material, to be connected to a negative terminal of a drive power supply. Likewise, a part of the ITO electrode was led out to an end of the element substrate through a desired pattern interconnection, which was integrally formed of the same material, to be connected to a positive terminal of the drive power supply. In addition, both electrodes (ITO electrode and Au electrode) of the pair were configured such that a predetermined voltage was applied therebetween.

A voltage was applied to the light-converting light-emitting element prepared through the above-described processes using the ITO electrode as the anode. When the Au electrode was irradiated with monochromatic light having a wavelength of 335 nm, the photoelectric current at room temperature and the illuminance (wavelength: 442 nm) of light emitted from Compound 1 were measured with respect to the applied voltage, respectively. When the measurement was performed with respect to the applied voltage, the photocurrent multiplication effect was observed at 20 V.

[Preparation of Dye Laser]

Example 9

The dye laser illustrated in FIG. 7 was prepared.

The dye laser having a configuration in which Compound 1 (in a deaerated acetonitrile solution; concentration $1 \times 10^{-4}$ M) was used as a laser dye in a XeCl excimer (excitation wavelength: 308 nm) was prepared. The emission wavelength was 430 nm to 450 nm, and a phenomenon in which the intensity was increased in the vicinity of 440 nm was observed.

[Preparation of Organic Laser Diode Light-Emitting Element]

Example 10

Referring to H. Yamamoto et al., Appl. Phys. Lett., 2004, 84, 1401, an organic laser diode light-emitting element having the configuration illustrated in FIG. 6 was prepared.

The organic laser diode light-emitting element was prepared according to the following order. First, the same processes as those of Example 1 were performed until the formation of the anode.

Next, 4,4'-bis[N-(1-naphthyl)-N-phenyl-amino]biphenyl (α-NPD) was deposited on the anode using a vacuum deposition method at a deposition rate of 1 angstrom/sec. Then, a hole injection layer having a thickness of 20 nm was formed on the anode.

Next, Compound 1 and FIrPic (iridium (III) bis[(4,6-difluorophenyl)-pyridinato-N,C2']picolinate) were codeposited on the hole injection layer using a vacuum deposition method to form an organic light-emitting layer. At this time, FIrPic which was the host material was doped with Compound 2 such that the content of Compound 2 in CFL was approximately 5.0%. Next, an exciton blocking layer having a thickness of 5 nm was formed on the organic light-emitting layer using Compound 1. Further, 1,3,5-tris(N-phenylbenzimidazol-2-yl)benzene (TPBI) was deposited on the exciton blocking layer using a vacuum deposition method. As a result, an electron transport layer having a thickness of 30 nm was formed on the hole blocking layer.

Next, MgAg (9:1, thickness: 2.5 nm) was deposited on the electron transport layer using a vacuum deposition method. Then, an ITO layer having a thickness of 20 nm was formed using a sputtering method. As a result, an organic laser diode light-emitting element was prepared.

The prepared organic laser diode light-emitting element was irradiated with laser beams (Nd:YAG laser SHG, 532 nm, 10 Hz, 0.5 ns) from the anode side to investigate ASE oscillation characteristics. When the laser beam irradiation is performed while changing the excitation intensity, the oscillation starts at 1.0 μJ/cm² and ASE in which the peak intensity is increased in proportion to the excitation intensity was observed.

INDUSTRIAL APPLICABILITY

The transition metal complex according to the aspect of the invention can be used as a luminescent material, a host material, a charge transport material, and an exciton blocking material in an organic EL (electroluminescence) element. In addition, the transition metal complex according to the aspect of the invention can be used for, for example, an organic electroluminescence element (organic EL element), a color-converting light-emitting element, a light-converting light-emitting element, a laser dye, and an organic laser diode element. Further, the transition metal complex according to the aspect of the invention can be used for a display device and an illumination device using each light-emitting element. Furthermore, the transition metal complex according to the aspect of the invention can be used for electronic equipment using each display device.

REFERENCE SIGNS LIST

1 SUBSTRATE
2 TFT CIRCUIT
2A, 2B INTERCONNECTION
3 INTERLAYER DIELECTRIC
4 PLANARIZING FILM
5 INORGANIC SEALING FILM
6 SEALING MATERIAL
7 BLACK MATRIX
8R RED COLOR FILTER
8G GREEN COLOR FILTER
8B BLUE COLOR FILTER
9 SEALING SUBSTRATE
8B BLUE FLUORESCENCE-CONVERTING LAYER
10, 20 ORGANIC LIGHT-EMITTING ELEMENT (ORGANIC EL ELEMENT, LIGHT SOURCE)
11 REPELLER
12 FIRST ELECTRODE (REPELLER)
13 HOLE TRANSPORT LAYER
14 ORGANIC LIGHT-EMITTING LAYER
15 ELECTRON TRANSPORT LAYER
16 SECOND ELECTRODE (REPELLER)
17 ORGANIC EL LAYER(ORGANIC LAYER)
18R RED PHOSPHOR LAYER
18G GREEN PHOSPHOR LAYER
19 EDGE COVER
30 COLOR-CONVERTING LIGHT-EMITTING ELEMENT
31 SCATTERING LAYER
40 LIGHT-CONVERTING LIGHT-EMITTING ELEMENT
50 ORGANIC LASER DIODE ELEMENT
60 DYE LASER
70 ILLUMINATION DEVICE
210 MOBILE PHONE (ELECTRONIC EQUIPMENT)
220 THIN-SCREEN TV (ELECTRONIC EQUIPMENT)
230 PORTABLE GAME MACHINE (ELECTRONIC EQUIPMENT)
240 LAPTOP COMPUTER (ELECTRONIC EQUIPMENT)
250 CEILING LIGHT (ILLUMINATION DEVICE)
260 ILLUMINATION STAND (ILLUMINATION DEVICE)

The invention claimed is:

1. A dicarbene transition metal complex of formula (1):

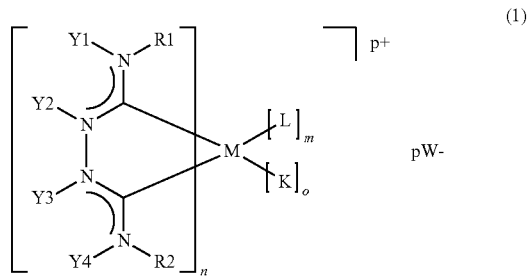

wherein:

M represents a transition metal element selected from the group consisting of Group 8 to Group 12 transition metal elements in the periodic table, wherein the transition metal element represented by M is in any oxidation state;

K represents an uncharged monodentate or bidentate ligand;

L represents a monodentate or bidentate monoanionic or dianionic ligand;

m represents an integer from 0 to 5;

o represents an integer from 0 to 5;

n represents an integer from 1 to 3;

p represents the number of charges in the complex which is represented by an integer from 0 to 4;

W— represents a monoanionic counterion;

wherein: m, o, n, and p are dependent on the oxidation state and coordination number of the transition metal element represented by M or on the charge on ligands and the charge on the entire complex;

Y1, Y2, Y3, and Y4 each independently represent a hydrogen atom, an alkyl group, a cycloalkyl group, a heterocycloalkyl group, an aryl group, a heteroaryl group, an aralkyl group, an alkenyl group, an alkynyl group, or an alkoxy group, wherein each group is optionally substituted or unsubstituted; and wherein Y1 and Y2, Y2 and Y3, and Y3 and Y4, independently of one another, are optionally bonded and integrated to form a saturated or unsaturated ring structure having at least two atoms between nitrogen atoms, wherein one or more atoms of the ring structure are optionally substituted with an alkyl group or an aryl group, and a substituent thereof is optionally further substituted or unsubstituted, and the ring structure optionally forms one or more further ring structures; and R1 and R2 each independently represent a hydrogen atom, an alkyl group, a cycloalkyl group, a heterocycloalkyl group, an aryl group, an aralkyl group, a heteroaryl group, an alkenyl group, an alkynyl group, or an alkoxy group, where each group is optionally substituted or unsubstituted.

2. The transition metal complex according to claim 1, wherein the transition metal complex of formula (1) is a transition metal complex of formula (2), (3), (4) or (5):

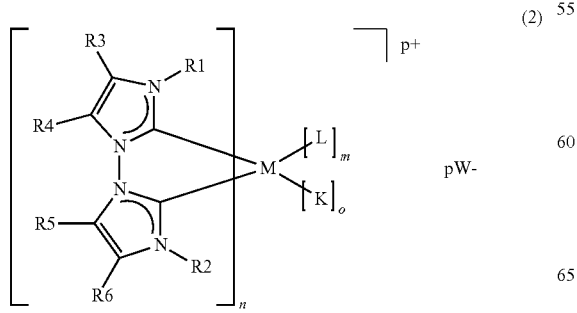
(2)

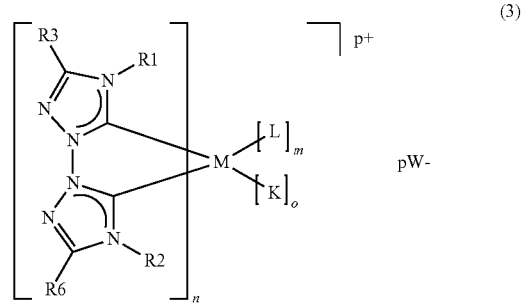
(3)

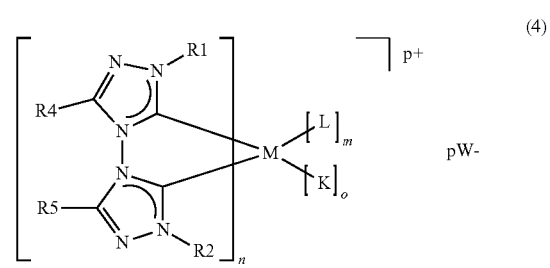
(4)

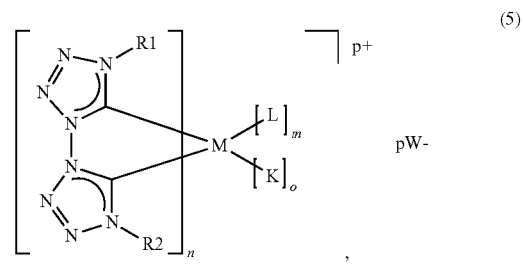
(5)

wherein:

R1 to R6 each independently represent a hydrogen atom, an alkyl group, a cycloalkyl group, a heterocycloalkyl group, an aryl group, a heteroaryl group, an aralkyl group, an alkenyl group, an alkynyl group, or an alkoxy group, wherein each group is optionally substituted or unsubstituted; and wherein R1 and R3, R3 and R4, R5 and R6, and R6 and R2, independently of one another, are optionally bonded and integrated to form a saturated or unsaturated ring structure, wherein one or more atoms of the ring structure are optionally substituted with an alkyl group or an aryl group, and wherein a substituent thereof is optionally further substituted or unsubstituted, and the ring structure optionally forms one or more further ring structures.

3. The transition metal complex according to claim 1, wherein the transition metal complex of formula (1) is a transition metal complex of formula (6) or (7):

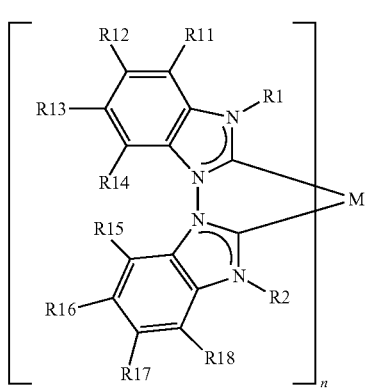

(6)

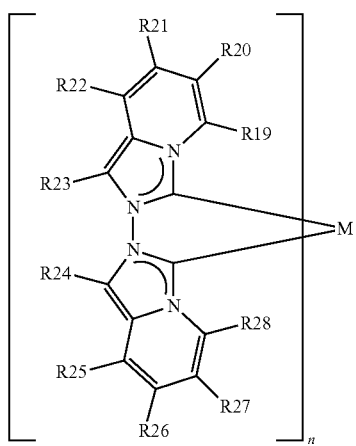

(7)

wherein:
R11 to R28 each independently represent a hydrogen atom, an alkyl group, a cycloalkyl group, a heterocycloalkyl group, an aryl group, a heteroaryl group, an aralkyl group, an alkenyl group, an alkynyl group, or an alkoxy group, wherein each group is optionally substituted or unsubstituted; and wherein R1 and and one of R11 to R14, and R2 and and one of R15 to R18, R19 to R23, and R24 to R28, independently of one another, are optionally bonded and integrated to form a saturated or unsaturated ring structure, wherein one or more atoms of the ring structure are optionally substituted with an alkyl group or an aryl group and wherein a substituent thereof is optionally further substituted or unsubstituted, and the ring structure optionally forms one or more further ring structures.

4. The transition metal complex according to claim 3, wherein R1, R2, and R11 to R18 in the formula (6) or R19 to R28 in the formula (7) each independently represent a hydrogen atom, a methyl group, or a phenyl group.

5. The transition metal complex according to any one of claim 3,
wherein the K represents a phosphine, a phosphonate, and a derivative thereof; an arsenate and a derivative thereof; a phosphite; CO; a pyridine; or a nitrile.

6. The transition metal complex according to claim 1, wherein the L represents a ligand having a structure represented by any one of the following formula (12) to (16):

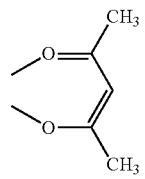

(12)

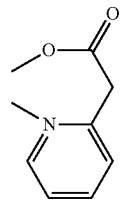

(13)

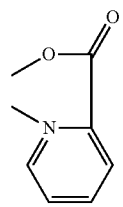

(14)

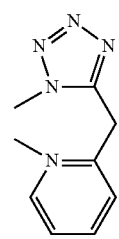

(15)

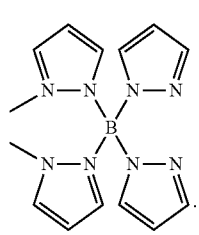

(16)

7. An organic light-emitting element comprising:
at least one organic layer that includes a light-emitting layer; and
a pair of electrodes between which the organic layer is interposed,
wherein at least a part of the organic layer contains the transition metal complex according to claim 1.

8. The organic light-emitting element according to claim 7, wherein the transition metal complex is a luminescent material.

9. The organic light-emitting element according to claim 7, wherein the transition metal complex is a host material.

10. The organic light-emitting element according to claim 7, wherein the transition metal complex is an exciton blocking material.

11. A color-converting light-emitting element comprising:
the organic light-emitting element according to claim 7; and
a phosphor layer that is disposed on a light-emitting side of the organic light-emitting element, wherein the phosphor layer is configured to absorb light emitted from the organic light-emitting element, and the phosphor layer is configured to emit light having a different wavelength from that of the absorbed light.

12. A display device comprising:
an image signal output portion configured to output an image signal;
a driver configured to apply a current or a voltage based on the signal output from the image signal output portion; and
a light-emitting portion configured to emit light based on the current or the voltage applied from the driver,
wherein the light-emitting portion is the organic light-emitting element according to claim 7.

13. The display device according to claim 12, wherein an anode and a cathode of the light-emitting portion are arranged in a matrix shape.

14. The display device according to claim 13, wherein the light-emitting portion is driven by a thin film transistor.

15. Electronic equipment comprising the display device according to claim 12.

16. An illumination device comprising:
a driver configured to apply a current or a voltage; and
a light-emitting portion configured to emit light based on the current or the voltage applied from the driver,
wherein the light-emitting portion is the organic light-emitting element according to claim 7.

17. The organic light-emitting element according to claim 7,
wherein the organic light-emitting element is configured to emit light in an ultraviolet wavelength range.

18. A color-converting light-emitting element comprising:
a light-emitting element; and
a phosphor layer that is disposed on a light-emitting side of the light-emitting element, wherein the phosphor layer is configured to absorb light emitted from the light-emitting element, and the phosphor layer is configured to emit light having a different wavelength from that of the absorbed light,
wherein the phosphor layer contains the transition metal complex according to claim 1.

19. A light-converting light-emitting element comprising:
at least one organic layer that includes a light-emitting layer;
a photoelectric layer configured to multiply a current; and
a pair of electrodes between which the organic layer and the photoelectric layer are interposed,
wherein the light-emitting layer contains the transition metal complex according to claim 1.

20. An organic light-emitting element comprising:
a continuous-wave excitation light source; and
a resonator structure that is irradiated with light emitted from the continuous-wave excitation light source,
wherein the resonator structure includes at least one organic layer that includes an active layer, and a pair of electrodes between which the organic layer is interposed, and
the active layer includes a host material doped with the transition metal complex according to claim 1.

21. A dye comprising:
a medium that contains the transition metal complex according to claim 1; and
an excitation light source with which oscillation is achieved by stimulated emission of phosphorescent light from the transition metal complex contained in the medium.

22. The transition metal complex according to claim 1, wherein each Y1 and Y2, and Y3 and Y4 are independently bonded and integrated to form a saturated or unsaturated ring structure having at least two atoms between nitrogen atoms, wherein one or more atoms of the ring structure are optionally substituted with an alkyl group or an aryl group, and a substituent thereof is optionally further substituted or unsubstituted.

23. The transition metal complex accordingly to claim 22, wherein each Y1 and Y2, and Y3 and Y4 are independently bonded and integrated to form a saturated or unsaturated ring structure having at least two atoms between nitrogen atoms, wherein one or more atoms of the ring structure are unsubstituted.

24. An organic light-emitting layer comprising:
a luminescent material having a triplet excitation level; and
a host material having a triplet excitation level higher than the luminescent material, wherein the luminescent material or the host material comprises the transition metal complex according to claim 1.

* * * * *